(12) United States Patent
Olaru et al.

(10) Patent No.: US 9,752,194 B2
(45) Date of Patent: Sep. 5, 2017

(54) METHODS AND COMPOSITIONS USEFUL FOR DIAGNOSING INFLAMMATORY BOWEL DISEASE-ASSOCIATED NEOPLASIA

(71) Applicant: THE JOHNS HOPKINS UNIVERSITY, Baltimore, MD (US)

(72) Inventors: Alexandru V. Olaru, Towson, MD (US); Stephen J. Meltzer, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/398,535

(22) PCT Filed: May 3, 2013

(86) PCT No.: PCT/US2013/039428
§ 371 (c)(1),
(2) Date: Nov. 3, 2014

(87) PCT Pub. No.: WO2013/166363
PCT Pub. Date: Nov. 7, 2013

(65) Prior Publication Data
US 2015/0133330 A1    May 14, 2015

Related U.S. Application Data

(60) Provisional application No. 61/642,054, filed on May 3, 2012.

(51) Int. Cl.
*C12Q 1/68* (2006.01)
*G01N 33/574* (2006.01)
*C12N 15/11* (2006.01)

(52) U.S. Cl.
CPC .......... *C12Q 1/6883* (2013.01); *C12N 15/111* (2013.01); *C12Q 1/6886* (2013.01); *G01N 33/57419* (2013.01); *C12N 2310/141* (2013.01); *C12N 2320/10* (2013.01); *C12Q 2600/16* (2013.01); *C12Q 2600/178* (2013.01); *G01N 2800/065* (2013.01)

(58) Field of Classification Search
CPC .................................................... C12C 1/6883
See application file for complete search history.

(56) References Cited

FOREIGN PATENT DOCUMENTS

WO    WO2012174293 A2 * 12/2012

OTHER PUBLICATIONS

Dalal et al. Gastroenterology & Hepatology 6:2010, 714-722.*
Olaru et al. Dynamic changes in the expression of microrna-31 during inflammatory bowel disease associated with neoplastic transformation. Gastroenterology, Elsevier, Philadelphia, PA vol. 138, No. 5, May 1, 2010, pp. S-46, AGA Abstracts 253.*
Olaru, A., et al., "Dynamic changes in the expression of microRNA-31 during inflammatory bowel disease-associated neoplastic transformation", Inflamm Bowel Dis, Jan. 2011, vol. 17, No. 1, pp. 221-231.

* cited by examiner

*Primary Examiner* — Brian Whiteman
(74) *Attorney, Agent, or Firm* — Johns Hopkins Technology Ventures

(57) ABSTRACT

The present invention relates to the field of biomarkers. More specifically, the present invention relates to the use of microRNAs to diagnose and monitor various diseases such as cancer. In particular embodiments, microRNA expression levels can serve as diagnostic biomarkers in inflammatory bowel disease-associated neoplasia (IBDN). More specifically, in certain embodiments, the present invention can be used to differentiate or distinguish IBDN from sporadic colorectal cancer (S-CRC), IBD-Dysplasia, IBD and/or normal.

6 Claims, 46 Drawing Sheets

Fig. 1b
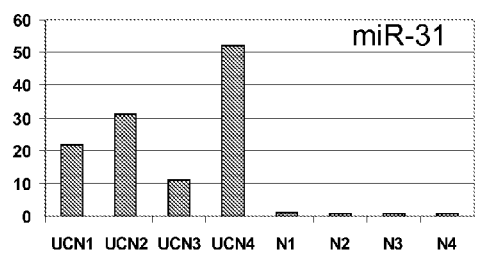
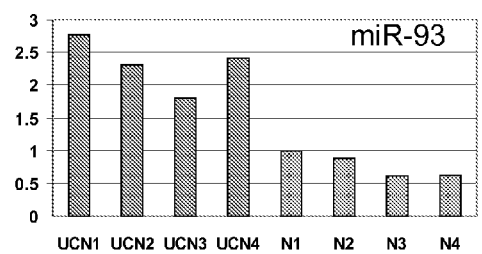
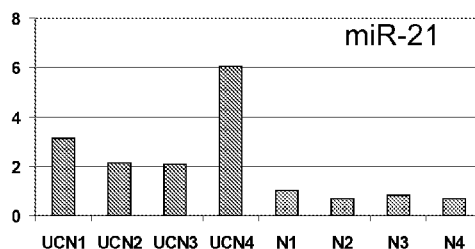
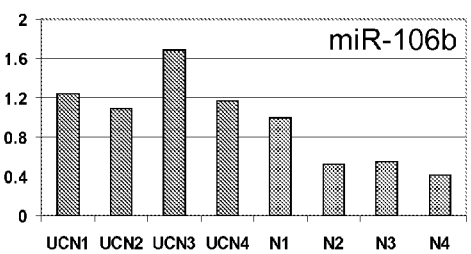
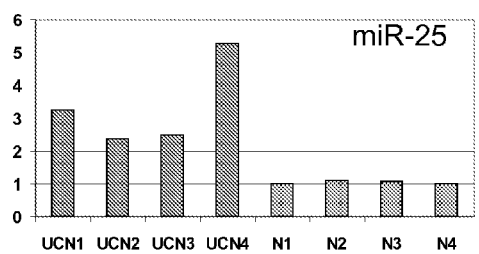
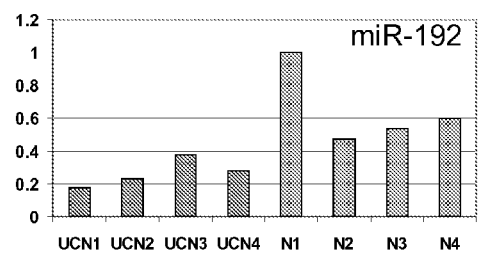
FIG. 17B

US 9,752,194 B2

METHODS AND COMPOSITIONS USEFUL FOR DIAGNOSING INFLAMMATORY BOWEL DISEASE-ASSOCIATED NEOPLASIA

CROSS-REFERENCE TO RELATED APPLICATIONS

This application is a 35 U.S.C. §371 U.S. national entry of International Application PCT/US2013/039428, having an international filing date of May 3, 2013, which claims the benefit of U.S. Provisional Application No. 61/642,054, filed May 3, 2012, the content of each of the aforementioned applications is herein incorporated by reference in their entirety.

STATEMENT OF GOVERNMENTAL INTEREST

This invention was made with government support under grant no. CA133012 awarded by the National Institutes of Health. The government has certain rights in the invention.

FIELD OF THE INVENTION

The present invention relates to the field of biomarkers. More specifically, the present invention relates to the use of microRNAs to diagnose and monitor various diseases such as cancer.

INCORPORATION-BY-REFERENCE OF MATERIAL SUBMITTED ELECTRONICALLY

This application contains a sequence listing. It has been submitted electronically via EFS-Web as an ASCII text file entitled "P10775-05 Sequence Listing.txt." The sequence listing is 1,288 bytes in size, and was created on May 3, 2013. It is hereby incorporated by reference in its entirety.

BACKGROUND OF THE INVENTION

Chronic idiopathic inflammatory bowel disease (IBD) predisposes to the development of colorectal carcinoma. Current preventive measures to diminish colorectal cancer mortality in IBD patients consist of periodic surveillance colonoscopies with random biopsies combined with total colectomy if dysplasia or neoplasia are found. However, challenges regarding management and early detection of inflammatory bowel disease-associated neoplasia (IBDN) still remain. Precancerous dysplastic lesions still escape detection. Morphologic alterations associated with chronic inflammation make dysplasia difficult to diagnose and prone to subjective interpretation. In addition, sporadic colorectal adenomas and adenocarcinomas may also develop in the setting of IBD. Distinguishing between IBD-caused dysplasia or neoplasia and sporadic adenoma or carcinoma is essential, since one diagnosis warrants total colectomy while the other can be treated with local excision.

SUMMARY OF THE INVENTION

The present invention is based, at least in part, on the discovery that microRNA expression levels can serve as diagnostic biomarkers in inflammatory bowel disease-associated neoplasia (IBDN). More specifically, in certain embodiments, the present invention can be used to differentiate or distinguish IBDN from sporadic colorectal cancer (S-CRC), IBD-Dysplasia, IBD and/or normal.

In one embodiment, a method for diagnosing inflammatory bowel disease-associated neoplasia (IBDN) in a patient comprises the steps of (a) obtaining a sample from the patient; (b) determining the amount of one or more microRNA (miR) biomarker proteins in the sample; and (c) correlating the amount of microRNA biomarker proteins to a patient having IBDN or to a patient not having IBDN, thereby providing the diagnosis. The sample can be blood, peripheral blood, serum, plasma, cerebrospinal fluid, urine, saliva, stool or synovial fluid. More specifically, the sample can be blood, plasma, serum or stool. In one embodiment, the sample is blood. In another embodiments, the sample is plasma. In an alternative embodiment, the sample is serum.

In certain embodiments, the step of determining the miR amount(s) is accomplished using polymerase chain reaction (PCR). Specifically, the PCR can be quantitative RT-PCR. In specific embodiments, the determining step is accomplished using a microarray with or without PCR. In further embodiments, the determining step is accomplished using mass spectrometry. In a specific embodiment, the mass spectrometry is MALDI-TOF. In another embodiments, the mass spectrometry method is selected reaction monitoring (SRM) or multiple SRM (MRM).

In one embodiment, the one or more microRNA biomarker proteins are miR-224, miR-135b, miR-31*, miR-452, miR-552, miR-31, miR-95, miR-424*, miR-550*, miR-96, miR-200a, miR-424, miR-542-3p, miR-7, miR-214, miR-335, miR-1246, miR-200b, miR-1288, miR-1295, miR-138, miR-892b, miR-501-5p, miR-760, miR-1305, miR-124, miR-150, miR-139-5p, miR-146b-5p, and miR-122, and wherein the diagnosis distinguishes between IBDN and inflammatory bowel disease (IBD).

In another embodiment, the microRNA biomarker protein is one or more proteins selected from the group consisting of miR-224, miR-135b, miR-31*, miR-452, miR-552, miR-31, miR-95, miR-424*, miR-550*, miR-96, miR-200a, miR-424, miR-542-3p, miR-7, miR-214, miR-335, miR-1246, miR-200b, miR-1288, miR-1295, miR-138, miR-892b, miR-501-5p, miR-760, miR-1305, miR-124, miR-150, miR-139-5p, miR-146b-5p, and miR-122, and wherein the diagnosis distinguishes between IBDN and inflammatory bowel disease (IBD).

In a more specific embodiment, the one or more microRNA biomarker proteins are miR-31, miR-552, miR-135b, miR-200a and miR-224, and wherein the diagnosis distinguishes between IBDN and inflammatory bowel disease (IBD).

In other embodiments, the one or more microRNA biomarker proteins are miR-31, miR-135 and miR-21, and wherein the diagnosis distinguishes between IBDN and sporadic colorectal cancer (S-CRC). In further embodiments, the one or more microRNA biomarker proteins are miR-424, miR-214, miR-503, miR-650, miR-194, and miR-192, and wherein the diagnosis distinguishes between IBDN and IBD-Dysplasia.

The present invention also provides a method for diagnosing IBDN in a patient having IBD comprising the steps of (a) collecting a sample from the patient; (b) measuring the levels of a panel of microRNA biomarker proteins in the sample collected from the patient using qRT-PCR or a microarray, wherein the panel of biomarkers comprises miR-31, miR-552, miR-135b, miR-200a and miR-224; and (c) comparing the levels of the panel of biomarkers with predefined levels of the same panel of biomarkers that correlate to a patient having IBDN and predefined levels of the same panel of biomarkers that correlate to a patient not having IBDN, wherein a correlation to one of the predefined levels provides the diagnosis. In a specific embodiment, the predefined levels of the same panel of biomarkers that correlate to a patient not having IBDN comprises a patient having IBD.

The present invention also provides a method for diagnosing IBDN in a patient having IBD-Dysplasia comprising the steps of (a) collecting a sample from the patient; (b) measuring the levels of a panel of microRNA biomarker proteins in the sample collected from the patient using qRT-PCR or a microarray, wherein the panel of biomarkers comprises miR-424, miR-214, miR-503, miR-650, miR-194, and miR-192; and (c) comparing the levels of the panel of biomarkers with predefined levels of the same panel of biomarkers that correlate to a patient having IBDN and predefined levels of the same panel of biomarkers that correlate to a patient not having IBDN, wherein a correlation to one of the predefined levels provides the diagnosis. In a specific embodiment, the predefined levels of the same panel of biomarkers that correlate to a patient not having IBDN comprises a patient having IBD-Dysplasia.

The present invention also provides methods for diagnosing inflammatory bowel disease-associated neoplasia (IBDN) in a patient comprising the steps of (a) obtaining a serum or plasma sample from the patient; (b) determining the amount of one or more microRNA (miR) biomarker proteins in the sample; and (c) correlating the amount of microRNA biomarker proteins to (i) a patient having IBDN and not having IBD based on expression levels of miR-31, miR-552, miR-135b, miR-200a and miR-224, (ii) a patient having IBDN and not having IBD-Dysplasia based on expression levels of miR-424, miR-214, miR-503, miR-650, miR-194, and miR-192, or (iii) a patient having IBDN and not having S-CRC based on expression levels of miR-31, miR-135 and miR-21, thereby providing the diagnosis. In another embodiment, the correlating step c(i) further comprises expression levels of miR-224, miR-135b, miR-31*, miR-452, miR-552, miR-31, miR-95, miR-424*, miR-550*, miR-96, miR-200a, miR-424, miR-542-3p, miR-7, miR-214, miR-335, miR-1246, miR-200b, miR-1288, miR-1295, miR-138, miR-892b, miR-501-5p, miR-760, miR-1305, miR-124, miR-150, miR-139-5p, miR-146b-5p, and miR-122. In another embodiment, the correlating step c(i) further comprises expression levels of miR-452, miR-95, miR-550*, miR-424, miR-542-3p, miR-7, miR-214, miR-335, miR-1246, miR-1295, miR-138, miR-760, miR-1305, miR-124, and miR-150. In certain embodiments, the determining step is accomplished using qRT-PCR or a microarray.

In certain embodiments, the one or more miR biomarker proteins detected using a method described herein can be miR-31, miR-552, miR-135b, miR-200a, miR-224 or combinations thereof. In some embodiments, the one or more miR biomarker proteins can be miR-31, miR-135b, miR-21 or combinations thereof. In particular embodiments, the one or more miR biomarker proteins can be miR-424, miR-214, miR-503 or combinations thereof. In specific embodiments, the one or more miR biomarker proteins can be miR-424, miR-214, miR-503, miR-650, miR-194, miR-192 or combinations thereof.

In certain embodiments, the one or more miR biomarker proteins detected using a method described herein can be at least one, at least two, at least three, at least four, at least five and so on of miR-224, miR-135b, miR-31*, miR-452, miR-552, miR-31, miR-95, miR-424*, miR-550*, miR-96, miR-200a, miR-424, miR-542-3p, miR-7, miR-214, miR-335, miR-1246, miR-200b, miR-1288, miR-1295, miR-138, miR-892b, miR-501-5p, miR-760, miR-1305, miR-124, miR-150, miR-139-5p, miR-146b-5p, and miR-122. In some embodiments, the one or more miR biomarker proteins can be at least one, at least two, at least three, at least four, at least five and so on of miR-452, miR-95, miR-550*, miR-424, miR-542-3p, miR-7, miR-214, miR-335, miR-1246, miR-1295, miR-138, miR-760, miR-1305, miR-124, and miR-150.

In particular embodiments, the one or more miR biomarker proteins detected using a method described herein can be at least one, at least two, at least three, at least four, at least five and so on of miR-552, miR-31, miR-31*, miR-203, miR-215, miR-135b, miR-200b*, miR-200a, miR-200c, miR-197, miR-200b, miR-192, miR-192*, miR-141, miR-96, miR-194*, miR-200a*, miR-429, miR-375, miR-424*, miR-183, miR-224, miR-892b, miR-122, miR-223, miR-501-5p, miR-146b-5p, miR-142-3p, miR-139-5p, miR-, miR-155, miR-1288, and miR-490-3p.

In specific embodiments, the one or more miR biomarker proteins detected using a method described herein can be the one or more miR biomarker proteins can be at least one, at least two, at least three, at least four, at least five and so on of miR-203, miR-215, miR-200c, miR-194, miR-200b, miR-192, miR-192*, miR-141, miR-194*, miR-200a*, miR-429, miR-375, miR-183, miR-223, miR-142-3p, miR-155, and miR-490-3p.

In certain embodiments, the one or more miR biomarker proteins detected using a method described herein can be a single biomarker or a combination of any miR described herein.

DETAILED DESCRIPTION OF THE INVENTION

Figure 1:
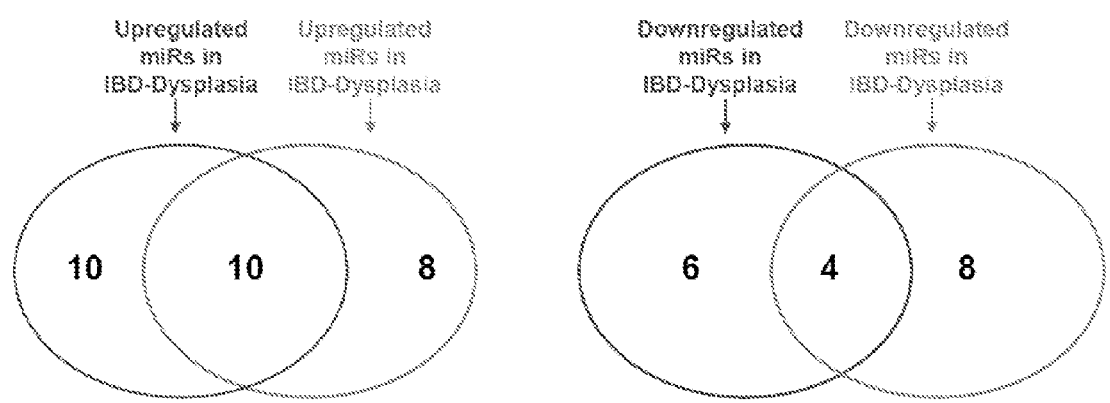
FIG. 1. Venn Diagram showing overlapping of miR dysregulation in IBD Dysplasia and IBD Cancer.
Figure 2:
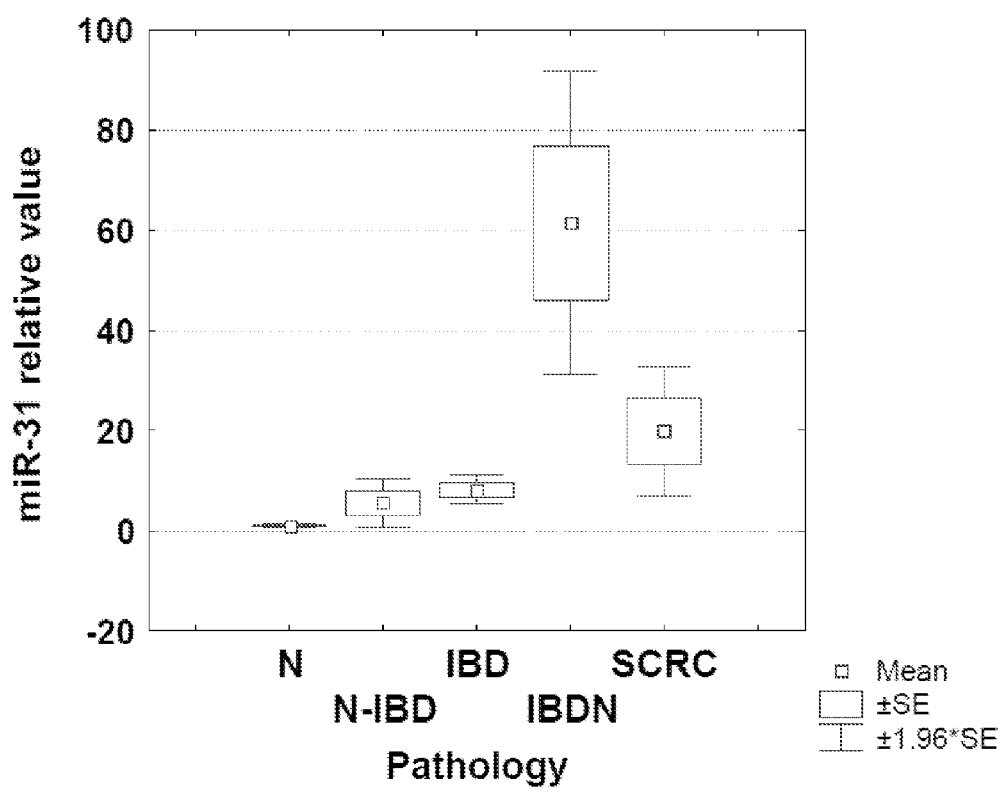
FIG. 2. Box plot showing that the expression level of miR-31 increases steadily along the normal to inflammation to cancer continuum.
Figure 3:
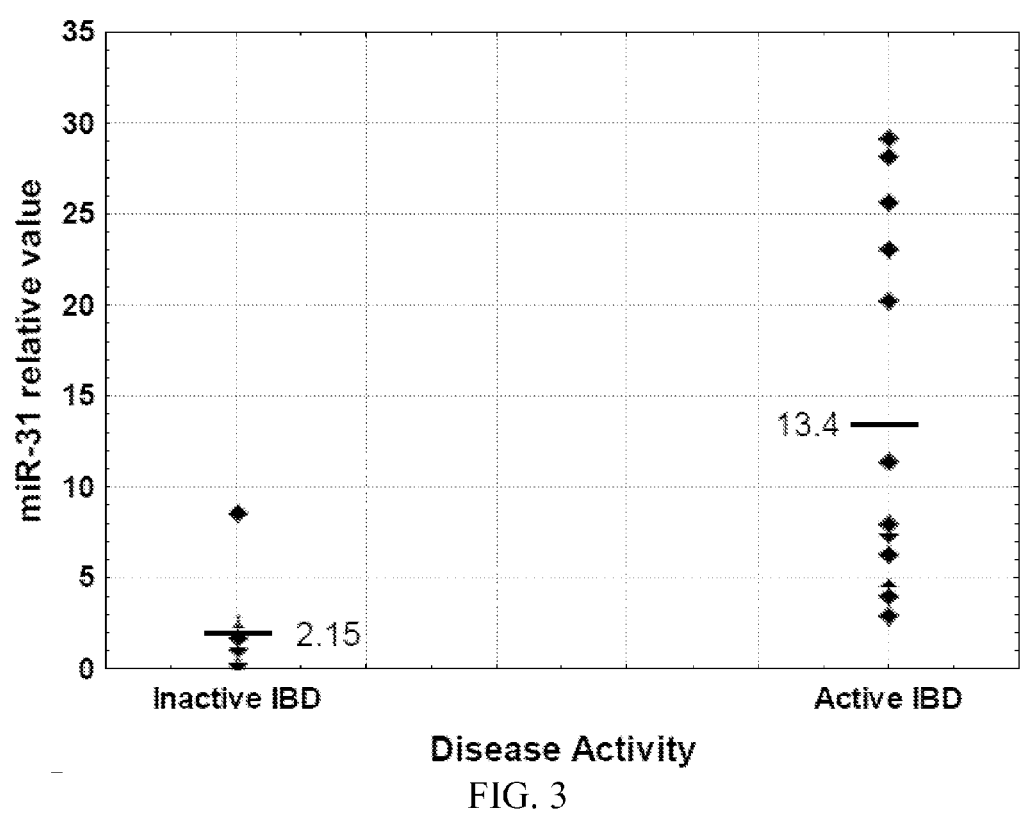
FIG. 3. In patients with active IBD, miR-31 exhibited a 6.23 fold increase over the quiescent disease group (p=0.002 Student's T-test).
Figure 4:
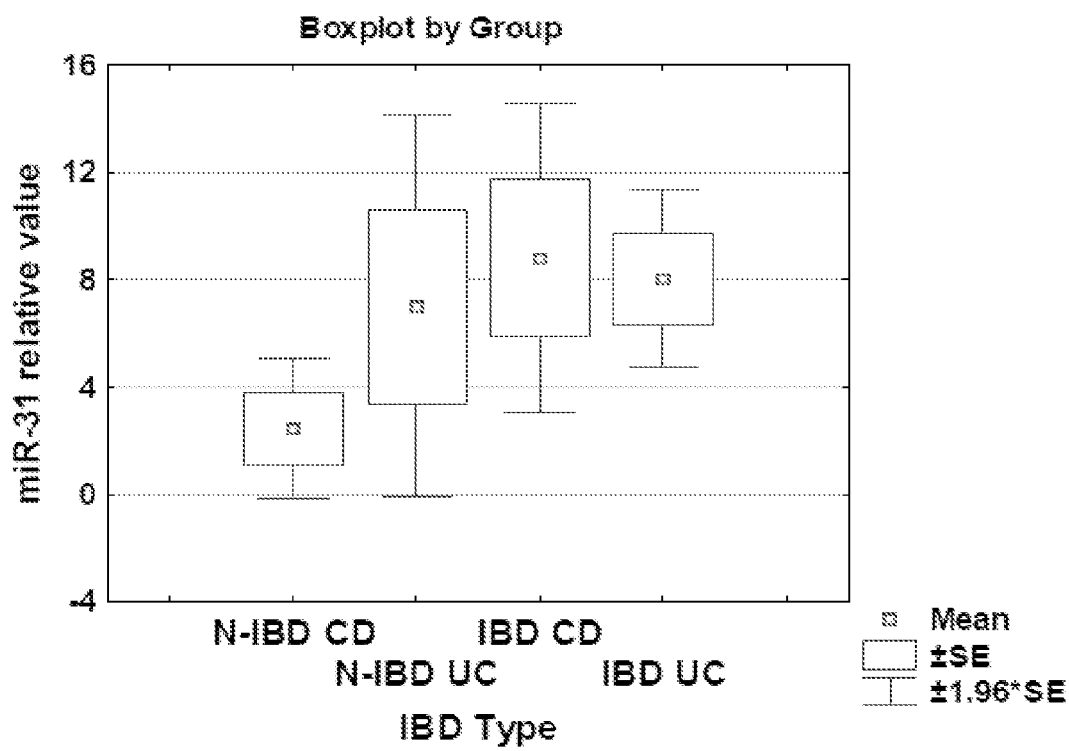
FIG. 4. Box plot showing that no statistically significant correlations with age, sex, duration of disease or IBD type were found.
Figure 4:
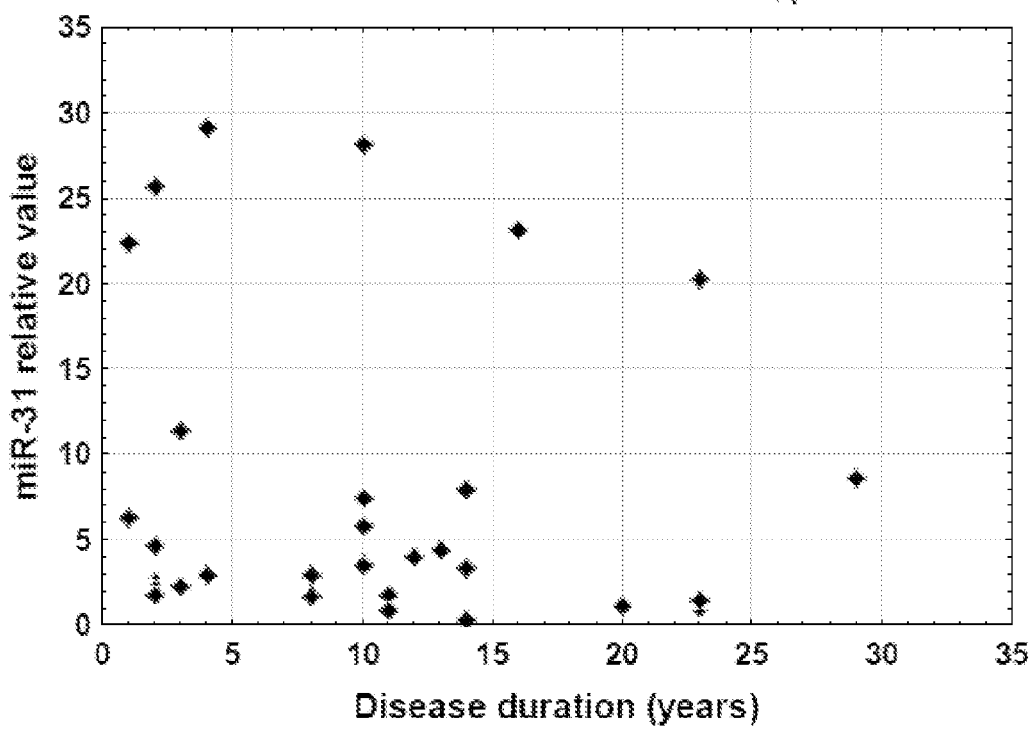
Figure 5:
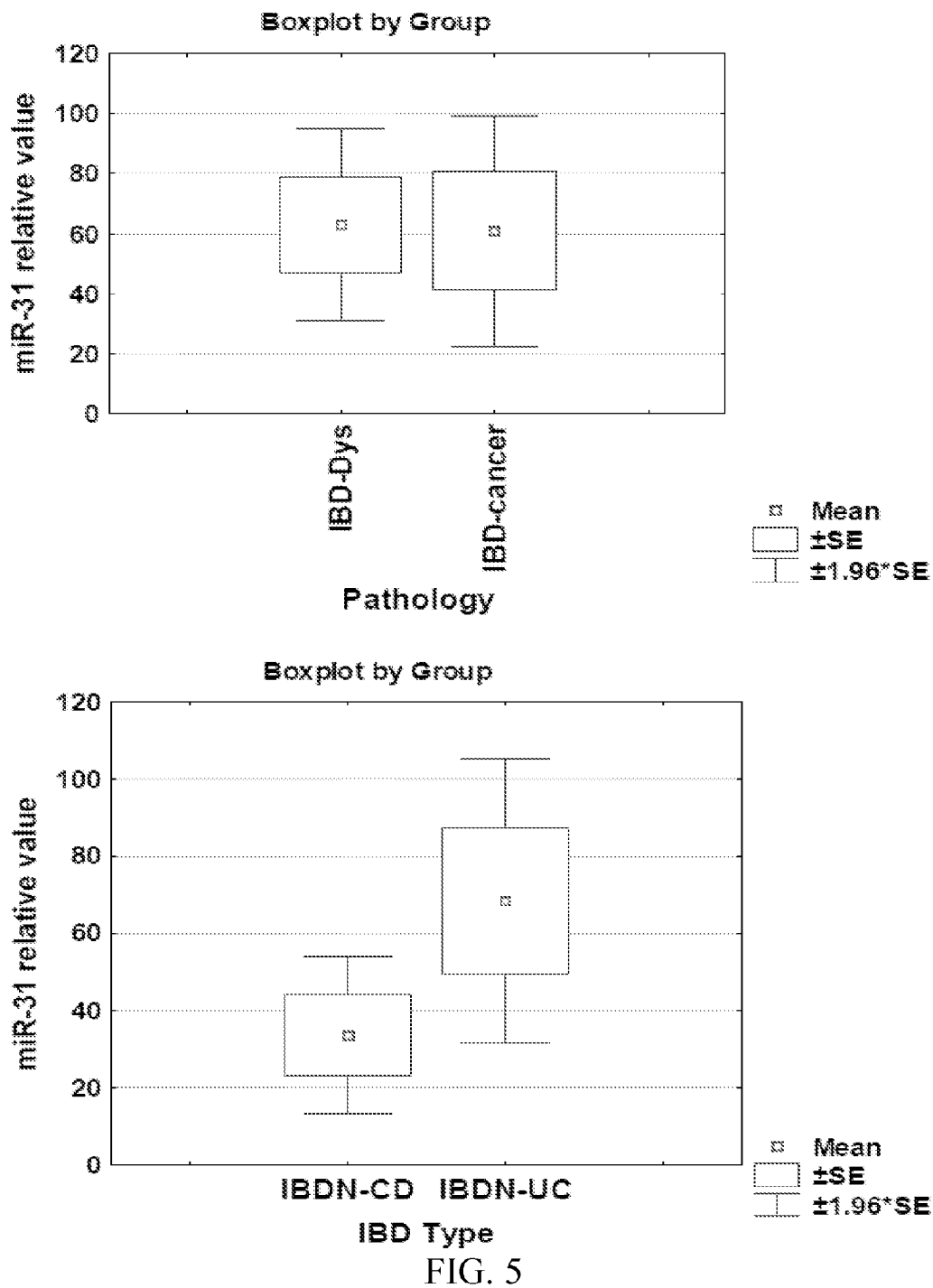
FIG. 5. Box plot showing that no difference in miR-31 expression was noted between IBD-Dysplasia and IBD carcinoma. Within the IBDN group (which includes IBD-Dysplasia and IBD-Cancer), no correlation was observed between miR-31 level and age, sex or underlying IBD type.
Figure 6:
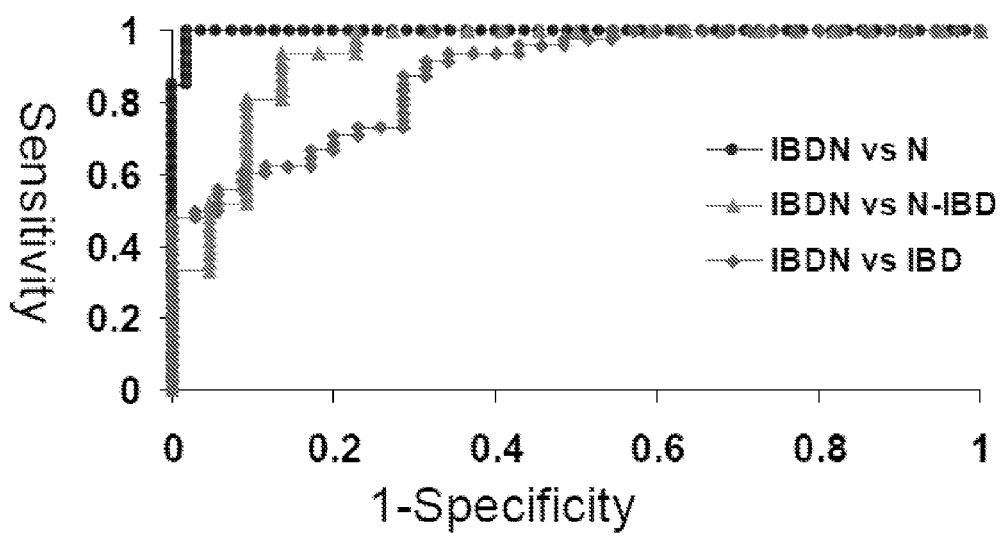
FIG. 6. Evaluation of the clinical utility of miR-31 expression as a disease marker for neoplasia in IBD.
Figure 7:
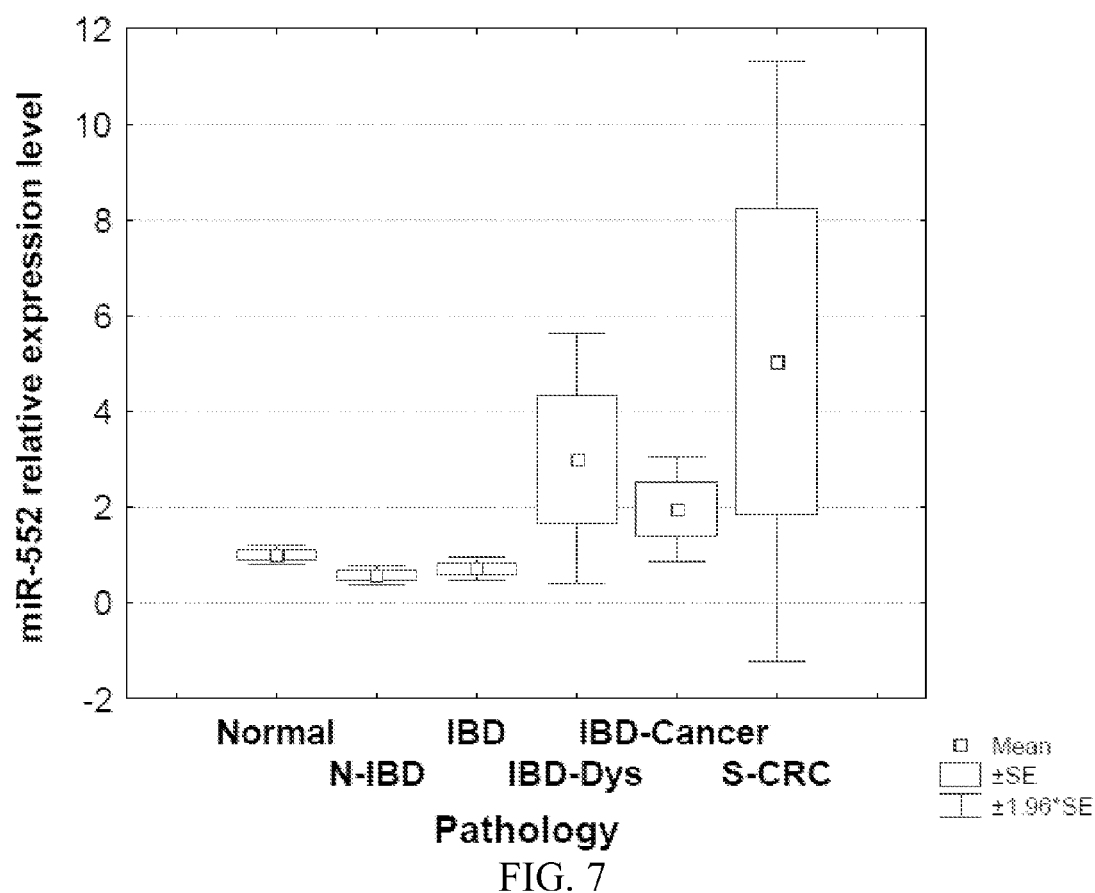
FIG. 7. Box plot of miR-552 expression levels in normal, N-IBD, IBD, IBD-Dysplasia, IBD-Cancer and S-CRC.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The following definitions are used throughout this specification. Other definitions are embedded within the specification for ease of reference.

As used herein, "comparing" refers to making an assessment of how the proportion, level or cellular localization of one or biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample.

As used herein, "indicates" or "correlates" (or "indication" or "correlation," depending on the context) in reference to a parameter, e.g., a modulated proportion, level, or cellular localization in the cell from a patient, may mean that the patient has cancer. In specific embodiments, the parameter may comprise the presence, absence and/or particular amounts of one or more biomarkers of the present invention. A particular set or pattern of one or more biomarkers (including the presence, absence, and/or particular amounts) may indicate that a patient has cancer (or correlated to a patient having cancer), in particular, IBDN. In other embodiments, a particular set or pattern of one or more biomarkers (including the presence, absence, and/or particular amounts) may be correlated to a patient having inflammatory bowel disease-associated neoplasia (IBDN) (or may indicate that a patient has IBDN). In yet other embodiments, a particular set or pattern of one or more biomarkers (including the presence, absence, and/or particular amounts) may be correlated to a patient being unaffected. In certain embodiments, "correlating" or "normalization" as used according to the present invention may be by any method of relating levels of expression or localization of markers to a standard valuable for the: assessment of the diagnosis, prediction of a cancer or cancer progression, assessment of efficacy of clinical treatment, identification of a tumor that may respond to a treatment, selection of a patient for a particular treatment, monitoring of the progress of treatment, and in the context of a screening assay, for the identification of an anti-IBDN therapeutic.

The terms "individual," "subject" or "patient" are used interchangeably herein, and refer to a mammal, particularly, a human. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The term "measuring" means methods which include detecting the presence or absence of a biomarker(s) in a sample, quantifying the amount of biomarker(s) in the sample, and/or qualifying the type of biomarker(s). Measuring can be accomplished by methods known in the art and those further described herein including, but not limited to, polymerase chain reaction. The term "measuring" is used interchangeably throughout with the term "detecting" and "performing an assay."

Various methodologies of the instant invention include a step that involves comparing a value, level, feature, characteristic, property, etc. to a "suitable control," referred to interchangeably herein as an "appropriate control," a "control sample" or a "reference." A "suitable control," "appropriate control," a "control sample" or a "reference" is any control or standard familiar to one of ordinary skill in the art useful for comparison purposes. In one embodiment, a "suitable control" or "appropriate control" is a value, level, feature, characteristic, property, etc. determined in a cell, organ, or patient, e.g., a control or normal cell, organ, or patient, exhibiting, for example, normal traits. For example, the biomarkers of the present invention may be assayed for their presence in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a cancer therapy on a patient. In yet another embodiment, a transcription rate, mRNA level, translation rate, protein level, biological activity, cellular characteristic or property, genotype, phenotype, etc. can be determined prior to, during, or after administering a cancer therapy into a cell, organ, or patient. In a further embodiment, a "suitable control" or "appropriate control" is a predefined value, level, feature, characteristic, property, etc.

II. MicroRNA Biomarkers for Inflammatory Bowel Disease-Associated Neoplasia (IBDN)

As used herein, the terms "microRNA," "miRNA," or "miR" are synonymous and include human miR, mature single stranded miR, precursor miR (pre-miR), and variants thereof. In some instances, the terms also include primary miR transcripts and duplex miR. The sequences for particular miR, including human mature and precursor sequences, can be found in several publicly available database including, but not limited to, the miRBase database (accessible at http://www.mirbase.org). For certain miR, a single precursor contains more than one mature miR sequence. In other instances, multiple precursor miR contain the same mature sequence. In some instances, mature miR have been renamed based on new scientific consensus. One of ordinary skill in the art appreciates that scientific consensus regarding the precise nucleic acid sequence for a given miR, in particular for mature forms of the miR, may change with time.

In one aspect, the present invention provides a panel of miR as biomarkers for IBDN. In particular embodiments, miR that are present at elevated levels in patients with IBDN are used as biomarkers. In other embodiments, miR that are present at reduced levels in the patients with IBDN are used as biomarkers. In some embodiments, more than one miR can be used as biomarkers. In such cases, the miR may all have elevated levels, all have reduced levels, or a mixture of miR with elevated and reduced levels may be used. In particular embodiments, the miR can be detected in a patient sample which includes, but is not limited to, blood, plasma, serum, urine, saliva, stool, synovial fluid and the like.

The terms "reduced levels" or "elevated levels" refer to the amount of a miR in a sample from a patient compared to the amount of the miR from a suitable control. For example, a miR present in the sera of an IBDN patient may be determined to be present at lower amounts than in serum from a subject who does not have IBDN. For certain miR, elevated levels in a patient serum or plasma sample correlate or indicate presence of or prognosis for IBDN. Other miR are present in reduced levels in patients with IBDN.

In particular embodiments, the level of the miR marker will be compared to a suitable control to determine whether the level is reduced or elevated. The control may be an external control, such as a miR in a serum or plasma sample from a patient known to be free of IBDN. In other embodiments, the external control may be a miR from a non-serum sample like a tissue sample or a known amount of a synthetic RNA. An internal control may be a miR from the same serum or plasma sample being tested. The identity of a miR control may be the same as or different from the patient serum or plasma miR being measured.

The terms "characterizing" and "identifying" includes making diagnostic or prognostic determinations or predictions of disease. In some instances, "characterizing" and "identifying" include identifying whether a subject has a cancer such as IBDN. The terms "characterizing" and "identifying" further includes distinguishing patients with IBDN from patients having other diseases. In other circumstances, "characterizing" includes determining the stage or aggressiveness of a disease state such as IBDN, determining an appropriate treatment method for IBDN, or assessing the effectiveness of a treatment for IBDN. The terms further include distinguishing patients among those having IBD, IBD-Dysplasia, and/or S-CRC.

The methods of the present invention can be used to characterize a patient with at least about 80%, at least about 85%, at least about 90%, at least about 91%, at least about 92%, at least about 93%, at least about 94%, at least about 95%, at least about 96%, at least about 97%, at least about 98%, or at least about 99% sensitivity. The degree of sensitivity indicates the percentage of patients with a disease who are positively characterized as having the disease. The methods described herein can also be used to characterize a patient with at least about 80%, at least about 85%, at least about 90%, at least about 91%, at least about 92%, at least about 93%, at least about 94%, at least about 95%, at least about 96%, at least about 97%, at least about 98%, or at least about 99% specificity (e.g., the percentage of non-diseased patients who are correctly characterized). The assay parameters can be adjusted to optimize for both sensitivity and specificity.

III. Samples Containing MicroRNA

The terms "sample," "biological sample," "patient sample" and the like, encompass a variety of sample types obtained from an individual, subject or a patient and can be used in a diagnostic or monitoring assay. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, serum, plasma, urine, saliva, stool and synovial fluid), solid tissue samples such as a biopsy specimen or tissue cultures or cells derived therefrom and the progeny thereof. The definition also includes samples that have been manipulated in any way after their procurement, such as by centrifugation, filtration, precipitation, dialysis, chromatography, treatment with reagents, washed or enriched for certain cell populations including tumor cells and the like. The terms further encompass a clinical sample, and also include cells in culture, cell supernatants, tissue samples, organs, bone marrow, and the like. In a specific embodiment, a sample comprises a blood sample.

In another embodiment, a serum sample is used. Serum is typically the fluid, non-cellular portion of coagulated blood. Plasma is also a non-cellular blood sample, but unlike serum, plasma contains clotting factors. In some embodiments, serum or plasma samples may be obtained from a human patient previously screened for IBD, IBD-Dysplasia, and/or IBDN using known diagnostic methods. In other embodiments, the patient has undergone a physical exam, endoscopy, esophagogastroduodenoscopy or biopsy to detect IBDN. Additional embodiments include measuring miR in samples from patients previously or currently undergoing treatment for IBDN, IBD-Dysplasia or IBD. The volume of the sample, e.g., blood, plasma serum or stool, obtained and used for the assay may be varied depending upon clinical intent.

Methods for obtaining and preparing serum samples are known in the art. Generally, blood is drawn into a collection tube using standard methods and allowed to clot. The serum is then separated from the cellular portion of the coagulated blood. In some methods, clotting activators such as silica particles are added to the blood collection tube. In other methods, the blood is not treated to facilitate clotting. Blood collection tubes are commercially available from many sources and in a variety of formats (e.g., Becton Dickinson Vacutainer® SST, glass serum tubes, or plastic serum tubes).

In some methods, the blood is collected by venipuncture and processed within three hours after drawing to minimize hemolysis and minimize the release of miR from intact cells in the blood. In some methods, blood is kept on ice until use. The blood may be fractionated by centrifugation to remove cellular components. In some embodiments, centrifugation to prepare serum can be at a speed of at least about 500, at least about 1000, at least about 2000, at least about 3000, at least about 4000, or at least about 5000×G. In certain embodiments, the blood can be incubated for at least about 10, at least about 20, at least about 30, at least about 40, at least about 50, at least about 60, at least about 90, at least about 120, or at least about 150 minutes to allow clotting. In other embodiments, the blood is incubated for at most 3 hours. When using plasma, the blood is not permitted to coagulate prior to separation of the cellular and acellular components. Serum or plasma can be frozen after separation from the cellular portion of blood until further assayed.

Before analysis, RNA may be extracted from serum or plasma and purified using methods known in the art. Many methods are known for isolating total RNA, or to specifically extract small RNAs, including miR. The RNA may be extracted using commercially-available kits (e.g., miRNeasy Mini Kit (QIAGEN, Inc. (Valencia, Calif.)); Perfect RNA Total RNA Isolation Kit (5 Prime, Inc. (Gaithersburg, Md.)); and mirVana™ miRNA Isolation Kit (Ambion, Inc. (Austin, Tex.))). Alternatively, RNA extraction methods previously published for the extraction of mammalian intracellular RNA or viral RNA may be adapted, either as published or with modification, for extraction of RNA from plasma and serum. RNA may be extracted from plasma or serum using silica particles, glass beads, or diatoms, as in the method or adaptations described in U.S. Patent Application Publication No. 2008/0057502.

IV. Methods to Measure The Level of MicroRNA

Many methods of measuring the levels or amounts of miR are contemplated. Any reliable, sensitive, and specific method can be used. In particular embodiments, a miR is amplified prior to measurement. In other embodiments, the level of miR is measured during the amplification process. In still other methods, the miR is not amplified prior to measurement.

A. Amplification Reactions

Many methods exist for amplifying miR nucleic acid sequences such as mature miR, precursor miR, and primary miR. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method is used, such as reverse transcription followed by real time quantitative PCR (qRT-PCR). See, e.g., Chen et al., 33(20) NUCL. ACIDS RES. e179 (2005).

A typical PCR reaction comprises multiple amplification steps or cycles that selectively amplify target nucleic acid species including a denaturing step in which a target nucleic acid is denatured; an annealing step in which a set of PCR primers (forward and reverse primers) anneal to complementary DNA strands; and an extension step in which a thermostable DNA polymerase extends the primers. By repeating these steps multiple times, a DNA fragment is amplified to produce an amplicon, corresponding to the target DNA sequence. Typical PCR reactions include about 20 or more cycles of denaturation, annealing, and extension. In many cases, the annealing and extension steps can be performed concurrently, in which case the cycle contains only two steps. Because mature miR are single-stranded, a reverse transcription reaction (which produces a complementary cDNA sequence) may be performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than about 15, fewer than about 20, fewer than about 25, fewer than about 30, or fewer than about 35 nucleotides in length. In additional embodiments, a primer is at least about 35 nucleotides in length.

In a further embodiment, a forward primer can comprise at least one sequence that anneals to a miR biomarker and alternatively can comprise an additional 5' non-complementary region. In another embodiment, a reverse primer can be designed to anneal to the complement of a reverse transcribed miR. The reverse primer may be independent of the miR biomarker sequence, and multiple miR biomarkers may be amplified using the same reverse primer. Alternatively, a reverse primer may be specific for a miR biomarker.

In some embodiments, two or more miR are amplified in a single reaction volume. One aspect includes multiplex q-PCR, such as qRT-PCR, which enables simultaneous amplification and quantification of at least two miR of interest in one reaction volume by using more than one pair of primers and/or more than one probe. The primer pairs comprise at least one amplification primer that uniquely binds each miR, and the probes are labeled such that they are distinguishable from one another, thus allowing simultaneous quantification of multiple miR. Multiplex qRT-PCR has research and diagnostic uses including, but not limited, to detection of miR for diagnostic, prognostic, and therapeutic applications.

The qRT-PCR reaction may further be combined with the reverse transcription reaction by including both a reverse transcriptase and a DNA-based thermostable DNA polymerase. When two polymerases are used, a "hot start" approach may be used to maximize assay performance. See U.S. Pat. Nos. 5,985,619 and 5,411,876. For example, the components for a reverse transcriptase reaction and a PCR reaction may be sequestered using one or more thermoactivation methods or chemical alteration to improve polymerization efficiency. See U.S. Pat. Nos. 6,403,341; 5,550,044; and 5,413,924.

B. Detection of MicroRNA

In certain embodiments, labels, dyes, or labeled probes and/or primers are used to detect amplified or unamplified miR. One of ordinary skill in the art will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miR amplification is preferred.

A probe or primer may include Watson-Crick bases or modified bases. Modified bases include, but are not limited to, the AEGIS bases (from EraGen Biosciences, Inc. (Madison, Wis.)), which have been described, e.g., in U.S. Pat. Nos. 6,001,983; 5,965,364; and 5,432,272. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan®) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,649,349 and 6,485,901), peptide nucleic acid (PNA) Molecular Beacons (see, e.g., U.S. Pat. Nos. 6,593,091 and 6,355,421), linear PNA beacons (see, e.g., U.S. Pat. No. 6,329,144), non-FRET probes (see, e.g., U.S. Pat. No. 6,150,097), Sunrise®/Amplifluor® probes (see, e.g., U.S. Pat. No. 6,548,250), stem-loop and duplex Scorpion™ probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse® probe (Sigma-Aldrich Corp. (St. Louis, Mo.)), hairpin probes (see, e.g., U.S. Pat. No. 6,596,490), PNA light-up probes, antiprimer quench probes (Li et al., 53 CLIN. CHEM. 624-33 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv)

provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

MicroRNA can be detected by direct or indirect methods. In a direct detection method, one or more miR are detected by a detectable label that is linked to a nucleic acid molecule. In such methods, the miR may be labeled prior to binding to the probe. Therefore, binding is detected by screening for the labeled miR that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miR, are detected using xMAP Microspheres (Luminex Corp. (Austin, Tex.)) conjugated with probes to capture the desired nucleic acids. Some methods may involve detection with polynucleotide probes modified, for example, with fluorescent labels or branched DNA (bDNA) detection.

In other embodiments, nucleic acids are detected by indirect detection methods. For example, a biotinylated probe may be combined with a stretavidin-conjugated dye to detect the bound nucleic acid. The streptavidin molecule binds a biotin label on amplified miR, and the bound miR is detected by detecting the dye molecule attached to the streptavidin molecule. In one embodiment, the streptavidin-conjugated dye molecule comprises Phycolink® Streptavidin R-Phycoerythrin (ProZyme, Inc. (Heward, Calif.)). Other conjugated dye molecules are known to persons skilled in the art.

Labels include, but are not limited to, light-emitting, light-scattering, and light-absorbing compounds which generate or quench a detectable fluorescent, chemiluminescent, or bioluminescent signal. See, e.g., Garman A., Non-Radioactive Labeling, Academic Press (1997) and Kricka, L., Nonisotopic DNA Probe Techniques, Academic Press, San Diego (1992). Fluorescent reporter dyes useful as labels include, but are not limited to, fluoresceins (see, e.g., U.S. Pat. Nos. 6,020,481; 6,008,379; and 5,188,934), rhodamines (see, e.g., U.S. Pat. Nos. 6,191,278; 6,051,719; 5,936,087; 5,847,162; and 5,366,860), benzophenoxazines (see, e.g., U.S. Pat. No. 6,140,500), energy-transfer fluorescent dyes, comprising pairs of donors and acceptors (see, e.g., U.S. Pat. Nos. 5,945,526; 5,863,727; and 5,800,996; and), and cyanines (see, e.g., WO 9745539), lissamine, phycoerythrin, Cy2, Cy3, Cy3.5, Cy5, Cy5.5, Cy7, FluorX (Amersham Biosciences, Inc. (Piscataway, N.J.)), Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, Tetramethylrhodamine, and/or Texas Red, as well as any other fluorescent moiety capable of generating a detectable signal. Examples of fluorescein dyes include, but are not limited to, 6-carboxyfluorescein; 2',4',1,4,-tetrachlorofluorescein, and 2',4',5',7',1,4-hexachlorofluorescein. In certain aspects, the fluorescent label is selected from SYBR-Green, 6-carboxyfluorescein ("FAM"), TET, ROX, VICTM, and JOE. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In further embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in Nucleic Acids in Chemistry and Biology (1996)).

In further aspects, methods relying on hybridization and/or ligation to quantify miR may be used including, but not limited to, oligonucleotide ligation (OLA) methods and methods that allow a distinguishable probe that hybridizes to the target nucleic acid sequence to be separated from an unbound probe. For example, HARP-like probes, as disclosed in U.S. Patent Application Publication No. 2006/0078894 may be used to measure the quantity of miR. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

In an additional embodiment of the method, a probe ligation reaction may be used to quantify miR. In a Multiplex Ligation-dependent Probe Amplification (MLPA) technique, pairs of probes which hybridize immediately adjacent to each other on the target nucleic acid are ligated to each other only in the presence of the target nucleic acid. See Schouten et al., 30 NUCL. ACIDS RES. e57 (2002). In some aspects, MLPA probes have flanking PCR primer binding sites. MLPA probes can only be amplified if they have been ligated, thus allowing for detection and quantification of miR biomarkers.

Furthermore, a sample may also be analyzed by means of a microarray. Microarrays generally comprise solid substrates and have a generally planar surface, to which a capture reagent (also called an adsorbent or affinity reagent) is attached. Frequently, the surface of a microarray comprises a plurality of addressable locations, each of which has the capture reagent (e.g., miR probes specific for particular biomarkers) bound there. Many microarrays are described in the art. These include, for example, miR biochips produced by Asuragen, Inc. (Austin, Tex.); Affymetrix, Inc. (Santa Clara, Calif.); GenoSensor Corp. (Tempe, Ariz.); Invitrogen, Corp. (Carlsbad, Calif.); and Illumina, Inc. (San Diego, Calif.).

V. Determination or Characterization of Cancer Status

The present invention relates to the use of biomarkers to detect cancer. More specifically, the biomarkers of the present invention can be used in diagnostic tests to determine, characterize, qualify, and/or assess cancer status, for example, to diagnose cancer, in an individual, subject or patient. In particular embodiments, the cancer is IBDN.

A. MicroRNA Biomarker Panels

The miR biomarkers of the present invention can be used in diagnostic tests to assess, characterize, determine, and/or qualify (used interchangeably herein) cancer status in a subject. The phrase "cancer status" includes any distinguishable manifestation of the disease, including non-disease. For example, cancer status includes, without limitation, the presence or absence of cancer (e.g., distinguishing between unaffected individuals (UI) and IBDN in a subject), the risk of developing cancer (e.g., distinguishing among UI, IBD, IBD-Dysplasia, IBDN, and/or S-CRC in a subject or patient), the stage of the cancer, the progress of cancer (e.g., progress of cancer or remission of cancer over time) and the effectiveness or response to treatment of cancer (e.g., clinical follow up and surveillance of IBD-Dysplasia and IBDN after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the miR biomarker panels of the present invention may show a statistical difference in different cancer statuses of at least about $p<0.05$, at least about $p<10^{-2}$, at least about $p<10^{-3}$, at least about $p<10^{-4}$ or at least about $p<10^{-5}$. Diagnostic tests that use these miR biomarkers may show a sensitivity and specificity of at least about 70%, at least about 75%, at least about 80%, at least about 85%, at least about 90%, at least about 95%, at least about 98% and about 100%.

The miR biomarkers are differentially present in UI (or normal control individuals (NC)), IBD, IBD-Dysplasia, IBDN and/or S-CRC, and, therefore, are useful in aiding in the determination of cancer status. In certain embodiments, the miR biomarkers are measured in a patient sample using the methods described herein. The measurement(s) may then be compared with a relevant diagnostic amount(s) or cut-off(s) that distinguish a positive cancer status from a negative cancer status. The diagnostic amount(s) represents a measured amount of a miR biomarker(s) above which or below which a subject is classified as having a particular cancer status. For example, if the miR biomarker(s) is/are up-regulated compared to normal during cancer (e.g., elevated levels), then a measured amount(s) above the diagnostic cutoff(s) provides a diagnosis of cancer. Alternatively, if the biomarker(s) is/are down-regulated during cancer (e.g., reduced levels), then a measured amount(s) below the diagnostic cutoff(s) provides a diagnosis of cancer. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of the miR biomarker(s) in a statistically significant number of samples from subjects with the different cancer statuses, and drawing the cut-off to suit the desired levels of specificity and sensitivity.

Indeed, as the skilled artisan will appreciate there are many ways to use the measurements of two or more miR biomarkers in order to improve the diagnostic question under investigation. In a quite simple, but nonetheless often effective approach, a positive result is assumed if a sample is positive for at least one of the markers investigated.

Frequently, however, the combination of miR biomarkers is evaluated. In particular embodiments, the values measured for biomarkers of a miR biomarker panel are mathematically combined and the combined value is correlated to the underlying diagnostic question. MicroRNA biomarker values may be combined by any appropriate state of the art mathematical method. Well-known mathematical methods for correlating a marker combination to a disease employ methods like discriminant analysis (DA) (e.g., linear-, quadratic-, regularized-DA), Kernel Methods (e.g., SVM), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will recognize an appropriate method to evaluate a miR biomarker combination of the present invention. In certain embodiments, the method used in correlating miR biomarker combination of the present invention is selected from DA (e.g., Linear-, Quadratic- and Regularized DA), Kernel Methods (e.g., SVM), Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression). Details relating to these statistical methods are found in the following references: Pepe, M. S., The Statistical Evaluation of Medical Tests for Classification and Prediction, Oxford Statistical Science Series, 28 (2003); Ruczinski et al., 12 J. OF COMPUTATIONAL AND GRAPHICAL STATISTICS 475-511 (2003); Breiman, L., 45 MACHINE LEARNING 5-32 (2001); Duda, R. O., Hart, P. E., Stork, D. G., Pattern Classification, Wiley Interscience, 2nd Edition (2001); Hastie, Trevor, Tibshirani, Robert, and Friedman, Jerome, The Elements of Statistical Learning, Springer Series in Statistics (2001); Friedman, J. H., 84 J. OF THE AMERICAN STATISTICAL ASSOCIATION 165-75 (1989); Breiman, L., Friedman, J. H., Olshen, R. A., and Stone, C. J. Classification and regression trees, California: Wadsworth (1984).

B. Determining Risk of Developing Cancer

In a specific embodiment, the present invention provides methods for determining the risk of developing cancer in a subject. MicroRNA biomarker amounts or patterns are characteristic of various risk states, e.g., high, medium or low. The risk of developing a cancer is determined by measuring the relevant miR biomarkers and then either submitting them to a classification algorithm or comparing them with a reference amount and/or pattern of miR biomarkers that is associated with the particular risk level.

C. Determining Stage of Cancer

In another embodiment, the present invention provides methods for determining the stage of cancer in a subject. Each stage of the cancer has a characteristic amount of a miR biomarker or relative amounts of a set of miR biomarkers (a pattern). The stage of a cancer is determined by measuring the relevant miR biomarkers and then either submitting them to a classification algorithm or comparing them with a reference amount and/or pattern of miR biomarkers that is associated with the particular stage.

D. Determining Course (Progression/Remission) of Cancer

In one embodiment, the present invention provides methods for determining the course of cancer in a subject. Cancer course refers to changes in cancer status over time, including cancer progression (worsening) and cancer regression (improvement). Over time, the amounts or relative amounts (e.g., the pattern) of the miR biomarkers change. For example, miR biomarker "X" is increased with IBDN, while biomarker "Y" may be decreased in IBDN. Therefore, the trend of these miR biomarkers, either increased or decreased over time toward cancer or non-cancer indicates the course of the disease. Accordingly, this method involves measuring one or more miR biomarkers in a subject at least two different time points, e.g., a first time and a second time, and comparing the change in amounts, if any. The course of cancer is determined based on these comparisons.

E. Subject Management

In certain embodiments of the methods of qualifying cancer status, the methods further comprise managing subject treatment based on the status. Such management includes the actions of the physician or clinician subsequent to determining cancer status. For example, if a physician makes a diagnosis of IBD, IBD-Dysplasia, IBDN or S-CRC, then a certain regime of monitoring (i.e., periodic endoscopy) would follow. A diagnosis of IBDN or S-CRC may then require a certain cancer therapy regimen. Alternatively, a diagnosis of non-IBDN (UI, IBD or IBD-Dysplasia, for example) might be followed with further testing to determine a specific disease that the patient might be suffering from. Also, further tests may be called for if the diagnostic test gives an inconclusive result on cancer status.

F. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of one or more of the miR biomarkers of the present invention may change toward a non-cancer profile. Therefore, one can follow the course of the amounts of one or more biomarkers in the subject during the course of treatment. Accordingly, this method involves measuring one or more miR biomarkers in a subject receiving drug therapy, and correlating the amounts of the miR biomarkers with the cancer status of the subject. One embodiment of this method involves determining the levels of one or more miR biomarkers at least two different time points during a course of drug therapy, e.g., a first time and a second time, and comparing the change in amounts of the miR biomarkers, if any. For example, the one or more miR biomarkers can be measured before and after drug administration or at two different time points during drug administration. The effect of therapy is determined based on these comparisons. If a treatment is effective, then one or more miR biomarkers will trend toward normal, while if treatment is ineffective, the one or more miR biomarkers will trend toward cancer indications.

G. Generation of Classification Algorithms for Qualifying Cancer Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain et al., "Statistical Pattern Recognition: A Review", 22(1) IEEE Transactions on Pattern Analysis and Machine Intelligence (2000).

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART-classification and regression trees), artificial neural networks such as back propagation networks, discriminant analyses (e.g., Bayesian classifier or Fischer analysis), logistic classifiers, and support vector classifiers (support vector machines). Another supervised classification method is a recursive partitioning process. Recursive partitioning processes use recursive partitioning trees to classify data derived from unknown samples. See U.S. Patent Application Publication No. 2002/0138208.

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm. Learning algorithms asserted for use in classifying biological information are described, for example, in WO 01/31580, U.S. Patent Applications Publication No. 2003/0055615, No. 2003/0004402, and No. 2002/0193950.

The classification models can be formed on and used on any suitable digital computer. Suitable digital computers include micro, mini, or large computers using any standard or specialized operating system, such as a Unix, Windows® or Linux™ based operating system. The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the miR biomarkers already discovered, and for finding new miR biomarkers. The classification algorithms, in turn, form the base for diagnostic tests by providing diagnostic values (e.g., cut-off points) for miR biomarkers used singly or in combination.

H. Kits for the Detection of Cancer Biomarkers

In another aspect, the present invention provides kits for qualifying cancer status, which kits are used to detect the miR biomarkers described herein. In a specific embodiment, the kit provided is a polymerase chain reaction kit comprising primers to the microRNA biomarkers of the present invention including, but not limited to, miR-224, miR-135b, miR-31*, miR-452, miR-552, miR-31, miR-95, miR-424*, miR-550*, miR-96, miR-200a, miR-424, miR-542-3p, miR-7, miR-214, miR-335, miR-1246, miR-200b, miR-1288, miR-1295, miR-138, miR-892b, miR-501-5p, miR-760, miR-1305, miR-124, miR-150, miR-139-5p, miR-146b-5p, and miR-122.

The kit may further comprise a solid support, such as a chip, microtiter plate (e.g., a 96-well plate), microfuge tubes, and the like. The kit may further comprise a means for detecting the biomarkers.

A cancer patient can be diagnosed by adding blood or blood serum from the patient to the kit and detecting the relevant miR biomarkers, specifically, by a method which comprises the steps of: (i) collecting blood or blood serum from the patient; (ii) separating blood serum from the patient's blood; (iii) adding the blood serum from patient to a diagnostic kit; (iv) amplifying the miR biomarkers with appropriate primers; and, (v) detecting and/or measuring the amplified miR biomarkers. In this method, the primers are brought into contact with the patient's blood. If the miR biomarkers are present in the sample, the primers will bind to the sample, or a portion thereof, and amplification will occur. In other kit and diagnostic embodiments, blood or blood serum need not be collected from the patient (i.e., it is already collected).

The kit can also comprise appropriate solutions to maximize amplification conditions and/or instructions for making such solutions. In a further embodiment, a kit can comprise instructions for suitable operational parameters in the form of a label or separate insert. For example, the instructions may inform a consumer about how to collect the sample, how to perform the amplification and detection steps, etc. In yet another embodiment, the kit can comprise one or more containers with biomarker samples, to be used as standard(s) for calibration, as well as applicable controls.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Identify miRs Uniquely Involved in Development and Progression of IBDN. We first aimed at identifying miR species that are dysregulated in IBDN. To that end, we proposed to perform miR arrays on 40 specimens (10 IBD-Cancers, 10 IBD-Dysplasias, 10 non-neoplastic IBDs, and 10 S-CRCs (S-CRCs)). We have performed 32 human miRs arrays (8 specimens per group). As proposed, we performed pair-wise comparisons between groups (e.g., IBDN vs. IBD, IBD-Cancer vs. IBD-Dysplasia and IBDN vs. S-CRC) by using binary classification algorithms, in particular Significance Analysis of Microarray (SAM). First, we contrasted IBD with IBD-Dysplasia (Table 1A). We found 20 miRs overexpressed and 10 underexpressed in IBD-Dysplasia vs. IBD. To identify miRs that are dysregulated in frank cancer, we also compared IBD with IBD Cancers (Table 1B). Similarly, expression of 30 miRs was altered in IBD-Cancer specimens, 18 being found up-regulated and 12 down-regulated vs. IBD.

Expectedly, there was a high degree of overlap between the results of the two comparisons, particularly among miRs with high fold differences (FIG. 1). For example, miR-31, miR-31*miR-552, miR-135b, miR-200a and miR-96, 6 out of the top 7 up-regulated miRs in IBD-Cancer were also up-regulated in IBD-Dysplasia as compared to non-neoplastic IBD. MiR-892b and miR-139-5p, the most underexpressed miRs in IBD-Cancer were also down-regulated in IBD-Dysplasia when compared with IBD specimens.

TABLE 1A

Differentially expressed miRs in IBD-Dysplasia vs. IBD
IBD vs IBD-Dysplasia

| Systematic Name | p-value | Fold dif. | regulation |
|---|---|---|---|
| hsa-miR-552 | 0.0085 | 6.31 | up in Dys |
| hsa-miR-31* | <0.0001 | 5.94 | up in Dys |
| hsa-miR-31 | 0.0001 | 5.85 | up in Dys |
| hsa-miR-200a | 0.0102 | 5.03 | up in Dys |
| hsa-miR-203 | 0.0195 | 4.71 | up in Dys |
| hsa-miR-200b* | 0.0074 | 4.60 | up in Dys |

TABLE 1A-continued

Differentially expressed miRs in IBD-Dysplasia vs. IBD
IBD vs IBD-Dysplasia

| Systematic Name | p-value | Fold dif. | regulation |
|---|---|---|---|
| hsa-miR-192 | 0.0121 | 4.52 | up in Dys |
| hsa-miR-200c | 0.0164 | 4.41 | up in Dys |
| hsa-miR-192* | 0.0355 | 4.40 | up in Dys |
| hsa-miR-200b | 0.0096 | 4.34 | up in Dys |
| hsa-miR-194 | 0.0190 | 4.13 | up in Dys |
| hsa-miR-194* | 0.0200 | 4.12 | up in Dys |
| hsa-miR-215 | 0.0228 | 4.06 | up in Dys |
| hsa-miR-141 | 0.0367 | 3.88 | up in Dys |
| hsa-miR-429 | 0.0426 | 3.71 | up in Dys |
| hsa-miR-200a* | 0.0398 | 3.20 | up in Dys |
| hsa-miR-96 | 0.0125 | 2.93 | up in Dys |
| hsa-miR-135b | 0.0254 | 2.88 | up in Dys |
| hsa-miR-183 | 0.0356 | 2.35 | up in Dys |
| hsa-miR-424* | 0.0407 | 2.09 | up in Dys |
| hsa-miR-490-3p | 0.0482 | 5.15 | down in Dys |
| hsa-miR-892b | 0.0002 | 3.63 | down in Dys |
| hsa-miR-143 | 0.0389 | 3.48 | down in Dys |
| hsa-miR-363 | 0.0226 | 3.38 | down in Dys |
| hsa-miR-145* | 0.0388 | 3.09 | down in Dys |
| hsa-miR-139-5p | 0.0033 | 3.09 | down in Dys |
| hsa-miR-223 | 0.0174 | 2.70 | down in Dys |
| hsa-miR-146b-5p | 0.0016 | 2.48 | down in Dys |
| hsa-miR-501-5p | 0.0014 | 2.25 | down in Dys |
| hsa-miR-30a* | 0.0328 | 2.07 | down in Dys |

TABLE 1B

Differentially expressed miRs in IBD-Cancer vs. IBD
IBD vs IBD Cancer (IBDC)

| Systematic Name | p-value | Fold dif. | regulation |
|---|---|---|---|
| hsa-miR-31 | 0.0037 | 7.22 | up in IBDC |
| hsa-miR-31* | 0.0028 | 6.40 | up in IBDC |
| hsa-miR-552 | 0.0036 | 6.26 | up in IBDC |
| hsa-miR-135b | 0.0002 | 6.05 | up in IBDC |
| hsa-miR-200a | 0.0196 | 4.06 | up in IBDC |
| hsa-miR-224 | 0.0001 | 3.68 | up in IBDC |
| hsa-miR-96 | 0.0135 | 3.52 | up in IBDC |
| hsa-miR-200b* | 0.0453 | 2.90 | up in IBDC |
| hsa-miR-7 | 0.0228 | 2.80 | up in IBDC |
| hsa-miR-214 | 0.0312 | 2.62 | up in IBDC |
| hsa-miR-550* | 0.0085 | 2.55 | up in IBDC |
| hsa-miR-452 | 0.0032 | 2.51 | up in IBDC |
| hsa-miR-95 | 0.0073 | 2.44 | up in IBDC |
| hsa-miR-335 | 0.0344 | 2.14 | up in IBDC |
| hsa-miR-542-3p | 0.0225 | 2.09 | up in IBDC |
| hsa-miR-424 | 0.0201 | 2.07 | up in IBDC |
| hsa-miR-1246 | 0.0356 | 2.06 | up in IBDC |
| hsa-miR-424* | 0.0080 | 2.02 | up in IBDC |
| hsa-miR-892b | <0.0001 | 6.09 | down in IBDC |
| hsa-miR-139-5p | 0.0096 | 3.50 | up in IBDC |
| hsa-miR-150 | 0.0089 | 3.32 | up in IBDC |
| hsa-miR-138 | <0.0001 | 2.98 | up in IBDC |
| hsa-miR-124 | 0.0025 | 2.90 | up in IBDC |
| hsa-miR-1288 | <0.0001 | 2.81 | up in IBDC |
| hsa-miR-501-5p | 0.0001 | 2.81 | up in IBDC |
| hsa-miR-1295 | <0.0001 | 2.69 | up in IBDC |
| hsa-miR-760 | 0.0001 | 2.63 | up in IBDC |
| hsa-miR-1305 | 0.0014 | 2.30 | up in IBDC |
| hsa-miR-146b-5p | 0.0139 | 2.18 | up in IBDC |
| hsa-miR-122 | 0.0342 | 2.05 | up in IBDC |

As clinicians, we confront ourselves with the dilemma of differentiating between sporadic vs. IBD-related neoplasia. In an attempt to study the miR profile and to quantify differences between these 2 pathological entities, we contrasted IBD-Cancer with S-CRC. We identified 77 differentially expressed miRs, with 45 being overexpressed, and 32 underexpressed in IBDN (Table 2A). These miR species are relevant for differences between the pathogenesis of colorectal cancers arising in IBD vs. sporadic cancers. Last, we also performed SAM comparing IBD-Dysplasia and IBD-Cancer. Six miRs were identified differentially expressed (Table 2B). These miRs are particularly important for functional studies that aim to identify early vs. late oncogenic events along the continuum from inflammation to dysplasia to cancer.

TABLE 2

Differentially expressed miRs in IBDC vs.
SCRC and IBD-Dysplasia vs. IBDC

| Systematic Name | p-value | Fold dif. | regulation |
|---|---|---|---|
| hsa-miR-31 | 0.0167 | 6.79 | Up in IBDC |
| hsa-miR-31* | 0.0420 | 4.70 | Up in IBDC |
| hsa-miR-1 | 0.0476 | 4.24 | Up in IBDC |
| hsa-miR-129-3p | 0.0453 | 3.87 | Up in IBDC |
| hsa-miR-551b | 0.0392 | 3.32 | Up in IBDC |
| hsa-miR-337-5p | 0.0060 | 3.32 | Up in IBDC |
| hsa-miR-199b-5p | 0.0066 | 3.16 | Up in IBDC |
| hsa-miR-199a-5p | 0.0113 | 3.15 | Up in IBDC |
| hsa-miR-376c | 0.0023 | 3.13 | Up in IBDC |
| hsa-miR-139-5p | 0.0485 | 3.06 | Up in IBDC |
| hsa-miR-142-5p | 0.0008 | 3.05 | Up in IBDC |
| hsa-miR-299-5p | 0.0065 | 3.03 | Up in IBDC |
| hsa-miR-130a | 0.0051 | 2.93 | Up in IBDC |
| hsa-miR-377 | 0.0066 | 2.92 | Up in IBDC |
| hsa-miR-30a* | 0.0209 | 2.81 | Up in IBDC |
| hsa-miR-142-3p | 0.0019 | 2.73 | Up in IBDC |
| hsa-miR-299-3p | 0.0085 | 2.68 | Up in IBDC |
| hsa-miR-654-3p | 0.0131 | 2.64 | Up in IBDC |
| hsa-miR-376a | 0.0060 | 2.63 | Up in IBDC |
| hsa-miR-379 | 0.0146 | 2.62 | Up in IBDC |
| hsa-miR-150 | 0.0245 | 2.62 | Up in IBDC |
| hsa-miR-144 | 0.0243 | 2.54 | Up in IBDC |
| hsa-miR-503 | 0.0048 | 2.54 | Up in IBDC |
| hsa-miR-136 | 0.0048 | 2.54 | Up in IBDC |
| hsa-miR-758 | 0.0079 | 2.50 | Up in IBDC |
| hsa-miR-199a-3p | 0.0132 | 2.47 | Up in IBDC |
| hsa-miR-154 | 0.0102 | 2.46 | Up in IBDC |
| hsa-miR-542-3p | 0.0048 | 2.42 | Up in IBDC |
| hsa-miR-424 | 0.0052 | 2.42 | Up in IBDC |
| hsa-miR-542-5p | 0.0019 | 2.39 | Up in IBDC |
| hsa-miR-127-3p | 0.0141 | 2.36 | Up in IBDC |
| hsa-miR-22* | 0.0055 | 2.23 | Up in IBDC |
| hsa-miR-381 | 0.0104 | 2.20 | Up in IBDC |
| hsa-miR-410 | 0.0132 | 2.20 | Up in IBDC |
| hsa-miR-136* | 0.0113 | 2.19 | Up in IBDC |
| hsa-miR-487b | 0.0136 | 2.19 | Up in IBDC |
| hsa-miR-495 | 0.0221 | 2.18 | Up in IBDC |
| hsa-miR-146b-5p | 0.0157 | 2.18 | Up in IBDC |
| hsa-miR-30a | 0.0128 | 2.17 | Up in IBDC |
| hsa-miR-1271 | 0.0284 | 2.14 | Up in IBDC |
| hsa-let-7e | 0.0363 | 2.13 | Up in IBDC |
| hsa-miR-342-5p | 0.0310 | 2.08 | Up in IBDC |
| hsa-miR-409-3p | 0.0213 | 2.08 | Up in IBDC |
| hsa-miR-140-5p | 0.0076 | 2.04 | Up in IBDC |
| hsa-miR-193b | 0.0124 | 2.03 | Up in IBDC |
| hsa-miR-424* | 0.0001 | 6.49 | down in IBDC |
| hsa-miR-203 | 0.0082 | 4.77 | down in IBDC |
| hsa-miR-664* | <0.0001 | 3.57 | down in IBDC |
| hsa-miR-622 | 0.0023 | 3.51 | down in IBDC |
| hsa-miR-192* | 0.0083 | 3.30 | down in IBDC |
| hsa-miR-663 | 0.0016 | 3.21 | down in IBDC |
| hsa-miR-429 | 0.0094 | 3.18 | down in IBDC |
| hsa-miR-1300 | 0.0005 | 3.15 | down in IBDC |
| hsa-miR-194* | 0.0157 | 3.14 | down in IBDC |
| hsa-miR-196a | 0.0489 | 3.02 | down in IBDC |
| hsa-miR-493 | <0.0001 | 2.96 | down in IBDC |
| hsa-miR-1305 | 0.0002 | 2.95 | down in IBDC |
| hsa-miR-892b | 0.0001 | 2.84 | down in IBDC |
| hsa-miR-1909* | 0.0006 | 2.83 | down in IBDC |
| hsa-miR-192 | 0.0090 | 2.74 | down in IBDC |
| hsa-miR-200a* | 0.0340 | 2.71 | down in IBDC |
| hsa-miR-200b | 0.0378 | 2.56 | down in IBDC |
| hsa-miR-200a | 0.0270 | 2.49 | down in IBDC |

TABLE 2-continued

Differentially expressed miRs in IBDC vs.
SCRC and IBD-Dysplasia vs. IBDC

| | | | |
|---|---|---|---|
| hsa-miR-610 | 0.0033 | 2.39 | down in IBDC |
| hsa-miR-138 | 0.0013 | 2.35 | down in IBDC |
| hsa-miR-1181 | 0.0183 | 2.29 | down in IBDC |
| hsa-miR-648 | 0.0005 | 2.28 | down in IBDC |
| hsa-miR-1321 | 0.0002 | 2.28 | down in IBDC |
| hsa-miR-17 | 0.0091 | 2.27 | down in IBDC |
| hsa-miR-627 | 0.0077 | 2.20 | down in IBDC |
| hsa-miR-1246 | 0.0185 | 2.14 | down in IBDC |
| hsa-miR-760 | 0.0009 | 2.10 | down in IBDC |
| hsa-miR-1208 | 0.0006 | 2.07 | down in IBDC |
| hsa-miR-765 | 0.0001 | 2.06 | down in IBDC |
| hsa-miR-584 | 0.0077 | 2.05 | down in IBDC |
| hsa-miR-425 | 0.0077 | 2.04 | down in IBDC |
| hsa-miR-1182 | 0.0001 | 2.03 | down in IBDC |

Table B. Differentially expressed miRs in
IBD-Dysplasia vs. IBDC
B. IBD-Dyplasia vs IBDC

| Systematic Name | p-value | Fold dif. | regulation |
|---|---|---|---|
| hsa-miR-424 | 0.0118 | 2.61 | up in IBDC |
| hsa-miR-214 | 0.0395 | 2.53 | up in IBDC |
| hsa-miR-503 | 0.0174 | 2.46 | up in IBDC |
| hsa-miR-650 | 0.0113 | 8.00 | down in IBDC |
| hsa-miR-194* | 0.0186 | 3.28 | down in IBDC |
| hsa-miR-192 | 0.0386 | 2.52 | down in IBDC |

The next proposed and executed step was to validate the microarray results by employing quantitative RT-PCR using the same template RNA specimens used for the microarray studies. For validation, we selected the top 5 most up-regulated miRs in IBD Cancer vs. IBD, namely miR-31, miR-552, miR-135b, miR-200a and miR-224. We also included miR-21. The qRT-PCR results accurately matched the array results, confirming the up-regulation in IBDN for all 6 miRs.

To verify that the miRs we identified as differentially expressed are not a mere expression of sampling error, in the next step, we tested the expression of these miRs in a larger cohort of 175 colon specimens. The cohort included healthy controls as well as IBD, IBD-Dysplasia, IBD-Cancer and S-CRC specimens. The summary of clinical data for each disease group is illustrated in Table 3. Detailed clinical data for the neoplastic specimens is shown in Table 4.

TABLE 3

Summary of clinical data for individual disease groups.

| | IBD-C | IBD-Dys | IBD | N-IBD | N | SCRC |
|---|---|---|---|---|---|---|
| Age | 49.4 | 57.4 | 46.2 | 48.8 | 60.6 | 68.9 |
| Sex M/F | 21/16 | 6/5 | 24/11 | 16/6 | 12/2 | 7/8 |
| IBD type UC/CD/IC | 30/5/2 | 9/2 | 24/11/0 | 15/7/0 | N/A | N/A |
| Location Right/Left | 12/25 | 5/6 | 5/30 | 18/4 | 26/29 | 3/12 |

N = normal from patients without IBD or colorectal cancer history;
N-IBD = normal "unaffected" specimens from IBD patients;
IBD = "affected" chronically inflamed specimens from IBD patients;
IBD-Dys = dysplastic specimens from IBD patients;
IBD-C = cancer specimens from IBD patients;
SCRC = sporadic colorectal specimens from patients without any history of IBD.

TABLE 4

Summary of Clinical Data for Neoplastic Specimens

| Pathology | Location | Grade | Stage | Age | Sex | Type |
|---|---|---|---|---|---|---|
| IBD-C | Ascending | MD-PD | T3N0 | 33 | F | UC |
| IBD-C | Rectum | MD | T3N0 | 51 | M | UC |
| IBD-C | Cecum | WD | T1N0 | 38 | M | UC |
| IBD-C | Sigmoid | MD-PD | T3N0 | 58 | F | UC |
| IBD-C | Rectum | PD | T3NX | 57 | M | UC |
| IBD-C | Rectum | MD | T3bN1 | 49 | M | UC |
| IBD-C | Rectosigmoid | PD | T1N0 | 46 | M | UC |
| IBD-C | Sigmoid | PD | T3N1 | 63 | M | UC |
| IBD-C | Ileocecal valve | WD-MD | T3N0 | 69 | F | CD |
| IBD-C | Rectum | MD-PD | T2N0 | 57 | F | UC |
| IBD-C | Rectum | MD-PD | T3N2 | 43 | M | CD |
| IBD-C | Splenic Flexure | PD | T3N2 | 72 | F | CD |
| IBD-C | Ileocecal valve | MD-PD | T2N0 | 39 | M | CD |
| IBD-C | Rectosigmoid | MD-PD | T3N0 | 38 | M | UC |
| IBD-C | Rectum | PD | T2N0 | 51 | M | UC |
| IBD-C | Transverse | MD-PD | T3N2 | 58 | F | UC |
| IBD-C | Sigmoid | MD-PD | T3N0 | 57 | F | UC |
| IBD-C | Rectum | MD | T3aN0 | 51 | F | UC |
| IBD-C | Rectum | WD | T2N1 | 59 | M | IC |
| IBD-C | Rectosigmoid | WD-MD | T4N2 | 37 | M | UC |
| IBD-C | Hepatic Flexure | PD | T3N0 | 44 | M | UC |
| IBD-C | Rectum | WD-PD | T3N2 | 53 | F | UC |
| IBD-C | Ascending | MD-PD | T3N2 | 28 | M | UC |
| IBD-C | Hepatic Flexure | WD-PD | T3aN2 | 27 | M | UC |
| IBD-C | Rectosigmoid | MD | T4N2 | 59 | F | UC |
| IBD-C | Sigmoid | MD-PD | T3N0 | 56 | M | UC |
| IBD-C | Sigmoid | MD | T3N0 | 58 | M | UC |
| IBD-C | Cecum | MD | T4N1 | 50 | M | UC |
| IBD-C | Descending | MD | T2N0 | 30 | F | CD |
| IBD-C | Rectosigmoid | MD | T3N0 | 51 | M | UC |
| IBD-C | Transverse | WD | T3N0 | 30 | M | UC |
| IBD-C | Ascending | MD | T3N2 | 44 | F | IC |
| IBD-C | Cecum | PD | T4N0 | 23 | M | UC |
| IBD-C | Rectum | NA | T4Nx | 43 | F | UC |
| IBD-C | Rectum | MD | T4N1 | 41 | F | UC |
| IBD-C | Sigmoid | WD | T1N0 | 83 | F | UC |

TABLE 4-continued

Summary of Clinical Data for Neoplastic Specimens

| Pathology | Location | Grade | Stage | Age | Sex | Type |
|---|---|---|---|---|---|---|
| IBD-C | Rectum | MD | T1N0 | 82 | F | UC |
| IBD-Dys | Sigmoid | DALM, HGD&LGD | NA | 74 | F | CD |
| IBD-Dys | Transverse | DALM, LGD | NA | 47 | M | UC |
| IBD-Dys | transverse | DALM, HGD | NA | 57 | M | UC |
| IBD-Dys | Ascending | DALM, LGD | NA | 60 | M | UC |
| IBD-Dys | Ascending | DALM, LGD&HGD | NA | 68 | F | UC |
| IBD-Dys | Transverse | DALM, LGD | NA | 47 | F | CD |
| IBD-Dys | Rectosigmoid | DALM, HGD&LGD | NA | 59 | F | UC |
| IBD-Dys | Rectum | DALM, HGD&LGD | NA | 59 | M | UC |
| IBD-Dys | Sigmoid | LGD | NA | 60 | M | UC |
| IBD-Dys | Rectum | LGD | NA | 50 | M | UC |
| IBD-Dys | Rectosigmoid | LGD-HGD | NA | 50 | F | UC |
| SCRC | Rectum | PD | T3N1 | 48 | F | no IBD |
| SCRC | Rectosigmoid | NA | T1N0M1 | 79 | M | no IBD |
| SCRC | Rectosigmoid | MD | T3N2 | 52 | F | no IBD |
| SCRC | Rectosigmoid | PD | T3N0 | 85 | M | no IBD |
| SCRC | Rectum | PD | T3N0 | 88 | M | no IBD |
| SCRC | Rectosigmoid | MD | T3N2M1 | 65 | F | no IBD |
| SCRC | Sigmoid | MD | T3N0 | 74 | F | no IBD |
| SCRC | Rectum | MD | T3N0M1 | 69 | F | no IBD |
| SCRC | Sigmoid | MD | T2N0 | 78 | M | no IBD |
| SCRC | Ascending | MD-PD | T4N1 | 86 | F | no IBD |
| SCRC | Cecum | MD | T3N1 | 59 | M | no IBD |
| SCRC | Descending | MD | T3N1 | 62 | F | no IBD |
| SCRC | Ascending | MD | T3N1 | 60 | M | no IBD |
| SCRC | Rectum | MD | T3N0 | 57 | M | no IBD |
| SCRC | Rectosigmoid | MD | T3N0 | 71 | F | no IBD |

IBD-Dys, dysplastic specimens from IBD patients;
IBD-C, cancer specimens from IBD patients;
SCRC, sporadic colorectal specimens from patients without any history of IBD;
WD, well differentiated;
MD, moderate differentiated;
PD, poorly differentiated;
LGD, low grade dysplasia;
HGD, high grade dysplasia;
DALM, dysplasia associated lesion or mass.

Figure 8:
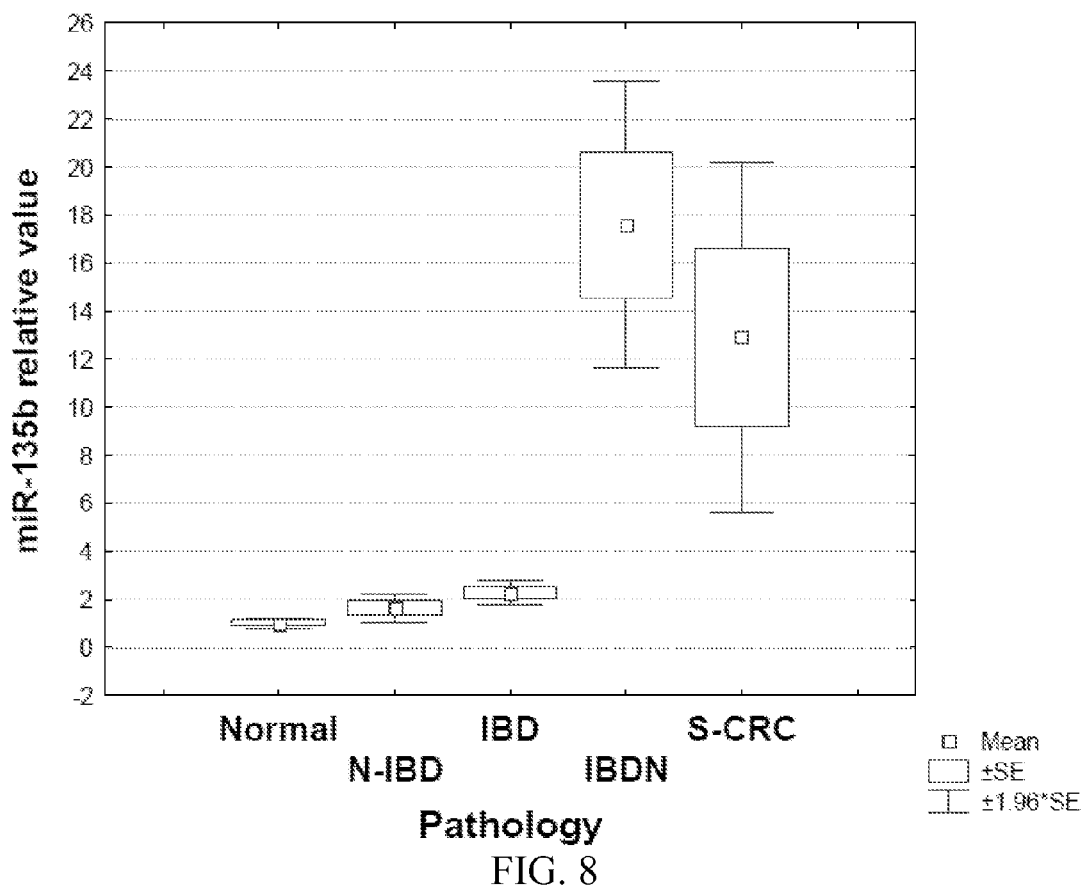
FIG. 8. Box plot showing that miR-135b expression was increased 17.5-fold in IBDN and 12.9-fold in S-CRC over the normal specimens from healthy patients.
Figure 9:
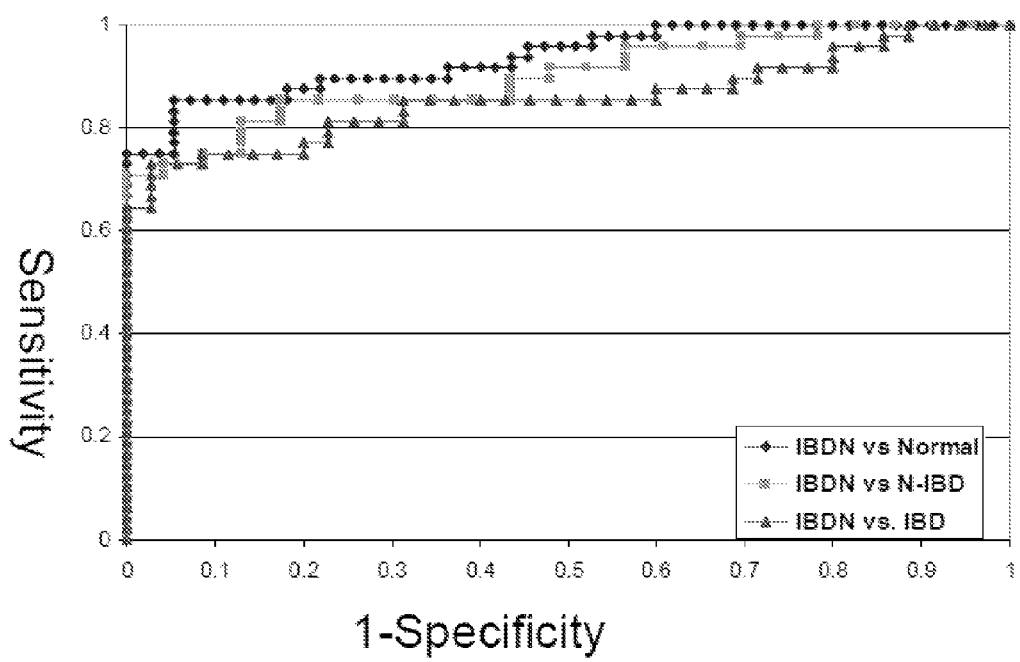
FIG. 9. Evaluation of the clinical utility of miR-135b expression as a disease marker for neoplasia in IBD.

The expression levels for miR-31, -21, 552, -135b, -224, and -200a are shown below:

miR-135b. This miR was found to be 17.5 fold increased in IBDN and 12.9 fold increased in S-CRC over the normal specimens from healthy patients (FIG. 8). A minimal but statistically significant difference was noted between IBD and normal specimens from non-IBD patients. No associations of miR-135b with respect to age, sex, duration of disease or IBD type were found. A 7.7 fold increase was observed in IBD neoplastic group compared to chronically inflamed nonneoplastic specimens from IBD patients. No difference between IBDN and S-CRC groups was observed. Next, we evaluated the potential clinical utility of miR-135b expression as disease marker for neoplasia in IBD (FIG. 9). MiR-135b sharply differentiated IBDNs from completely normal colonic mucosae (Ns), as demonstrated by an area under the ROC curve (AUROC) of 0.93 (sensitivity 85.42%, specificity 94.5% at the point on the curve closest to the origin). In our comparison of IBDNs vs. "unaffected" non-neoplastic IBD (N-IBDs), the AUROC was 0.899 (sensitivity 81.25%; specificity 86.96% at the point on the curve closest to the origin) for miR-135b qRTPCR; while in our comparison of IBDNs vs. inflamed but non-neoplastic IBD (IBDs), the AUROC was 0.857 (sensitivity 81.25%, specificity 77.14 at the point on the curve closest to the origin).

miR-200a. The qRT-PCR data performed on the specimens used in the microarray screening step confirmed the microarray results. Nonetheless, when we tested the expression of miR-200a in the larger, 178 specimen-cohort, no significant difference was detected between cancer, chronically inflamed and normal groups in our larger cohort (data not shown). No statistically significant correlations of miR-200a with age, sex, duration of disease or IBD type were found.

Figure 10:
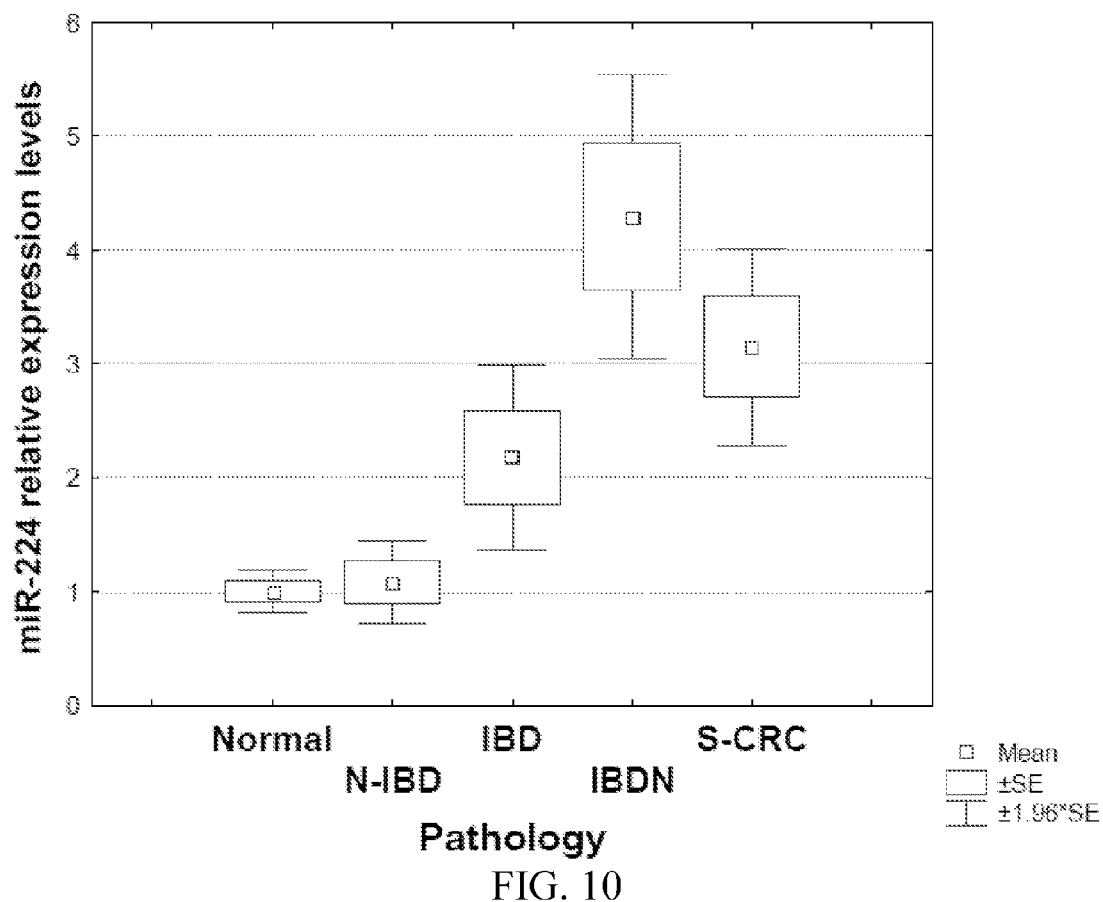
FIG. 10. Box plot of miR-224 expression in normal, N-IBD, IBD, IBDN and S-CRC.
Figure 11:
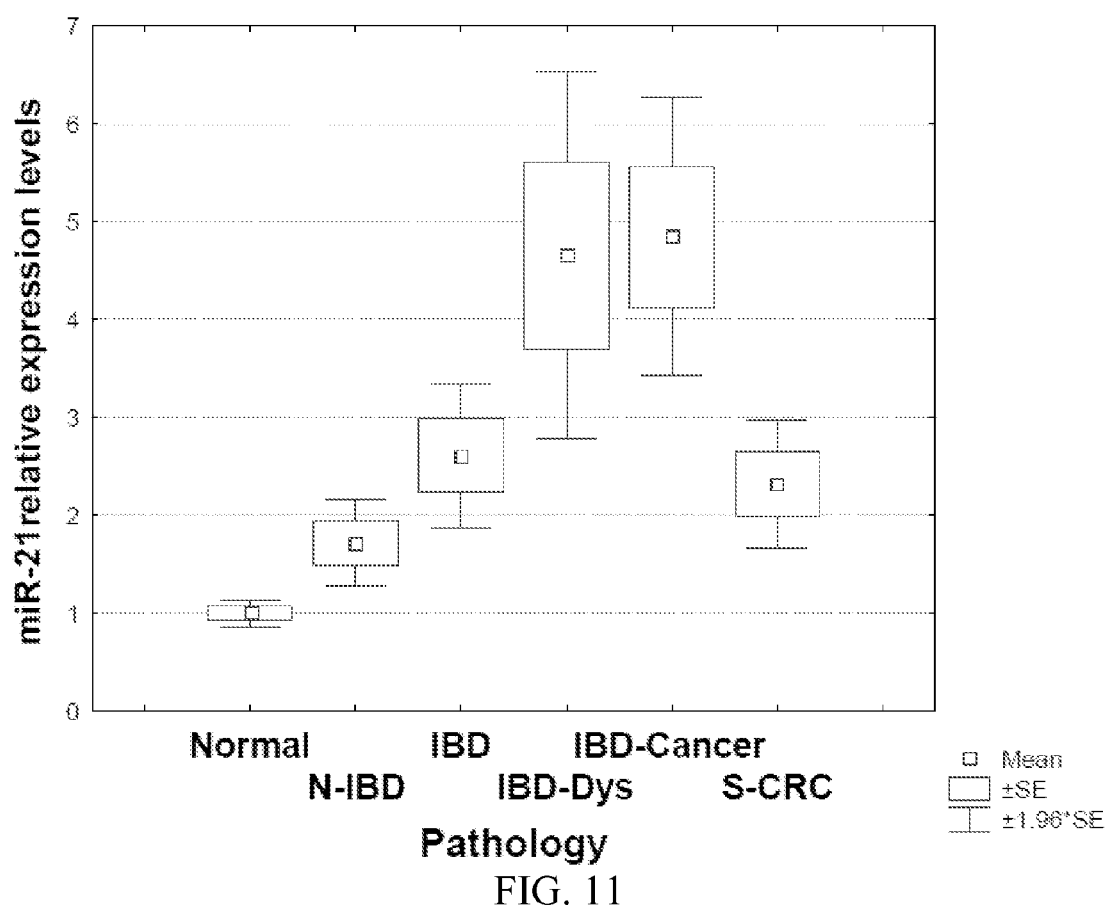
FIG. 11. Box plot of miR-21 expression in normal, N-IBD, IBD, IBD-Dys, IBD-Cancer and S-CRC.

As FIG. 10 demonstrates, miR-224 displayed a gradual increase from N-IBD to IBD-Cancer. Of note, in contrast to miR-31, there was no difference between normal specimens from patients without IBD (Normal in the FIG.) and unaffected specimens from patients with IBD (N-IBD). Also of clinical interest, miR-224 was 2.09 fold higher in IBD-Cancer vs. IBD (p=0.012, Student's t-test). In addition, miR-224 was found 3.14 fold up-regulated in SCRC vs. normal specimens (p<0.001, Student's t-test). Taken together, these results suggest that miR-224 exhibits a stepwise progression from normal to inflammation to neoplasia. No statistically significant correlations of miR-224 with age, sex, duration of disease, or IBD type were found.

miR-21. As FIG. 11 demonstrates, the expression of miR-21 in the large, 178-specimen cohort, accurately reflected our preliminary microarray experiments. miR-21 demonstrated an increased expression from normal to IBDN. These data suggest that miR-21 may be involved in the inflammatory as well as in the neoplastic transformation processes in IBD. To further augment the potential clinical use of miR-21 as disease marker, the expression of miR-21 was statistically significantly different between IBD-Cancer and S-CRC. The prospective value of differentiating between these 2 types of neoplasia stems from the vastly different management (total colectomy for neoplasia related to IBD vs. polypectomy or segmental resection for neoplasms with sporadic etiology). No associations of miR-21 with respect to age, sex, duration of disease or IBD type were found.

miR panel. Lastly, in the last part of this first year of the award, we will explore the increment in diagnostic power by evaluating a linear combination of the miR levels using coefficients obtained from a multivariate logistic discriminant analysis. We will test a forward stepwise model as well as a backward step-wise algorithm. We will employ the Discriminatory Analysis module within the Multivariate Exploratory Techniques in Statistica software (StatSoft, Tulsa, Okla.).

Example 2

Figure 12:
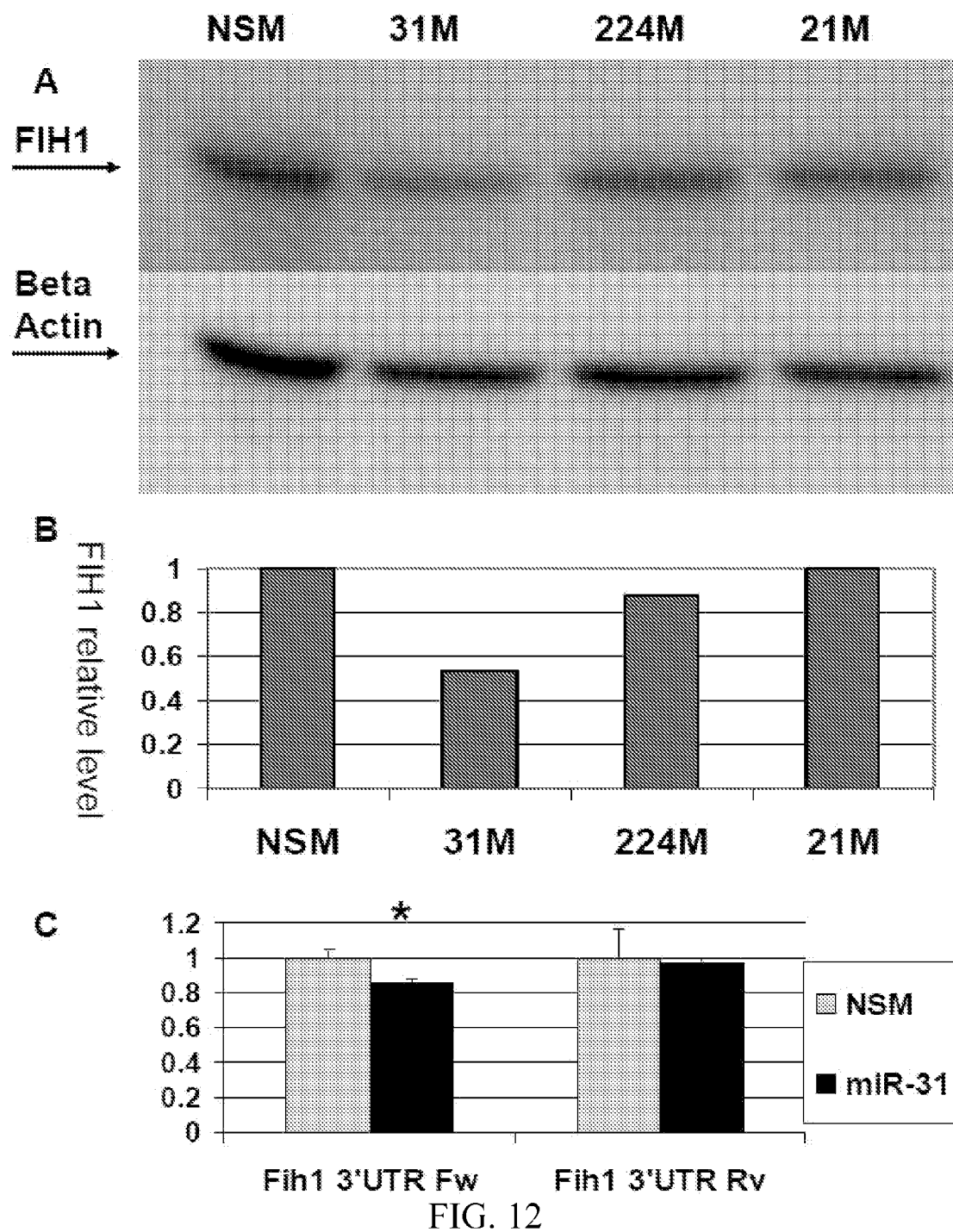
FIG. 12. (A) miR31-effect on FIH1 protein expression. (B) Quantification of FIH1 protein levels by densitometry. (C) Interaction of miR-31 with FIH1 3'UTR.

Identify genes that are controlled by specific dysregulated IBDN miRs. In the initial application, we have proposed to focus our mRNA target identification to miR-31, since this miR species appeared to accurately reflect the neoplastic progression. To this end, we have investigated 2 potential miR-31 mRNA targets. These targets were predicted by TargetScan (www.targetscan.org) to have complementarity in their 3'UTR to the seed region of miR-31. We therefore verified the regulation of liver receptor homolog-1 (LRH-1) and factor inhibiting hypoxia inducible factor-1 (FIH-1) by miR-31. LRH-1 protein expression proved to be independent of miR-31. Nonetheless, upon transfection of colon cancer cell lines with miR-31 mimic, FIH-1 protein expression was substantially reduced (46.63%) compared to cells transfected with a nonspecific control miR (FIGS. 12A and B). To add further negative controls, these cells were also transfected with mimics of miR-21 or miR-224. Next, we aimed at further describing the interaction between miR-31 and FIH-1. We sought to determine whether miR-31 interacts directly with the 3'-UTR of FIH1 (FIG. 12C). Compared to nonspecific negative control, miR-31-transfected HCT116 colon cancer cells demonstrated significantly lower FIH1 3'UTR luciferase activity (14.03%, p=0.001 Student's t-test). Reversing orientation of the FIH1 3'UTR did not altered the luciferase activity, confirming the direct nature of the interaction between miR-31 and the 3'UTR of FIH1 mRNA.

Figure 13:
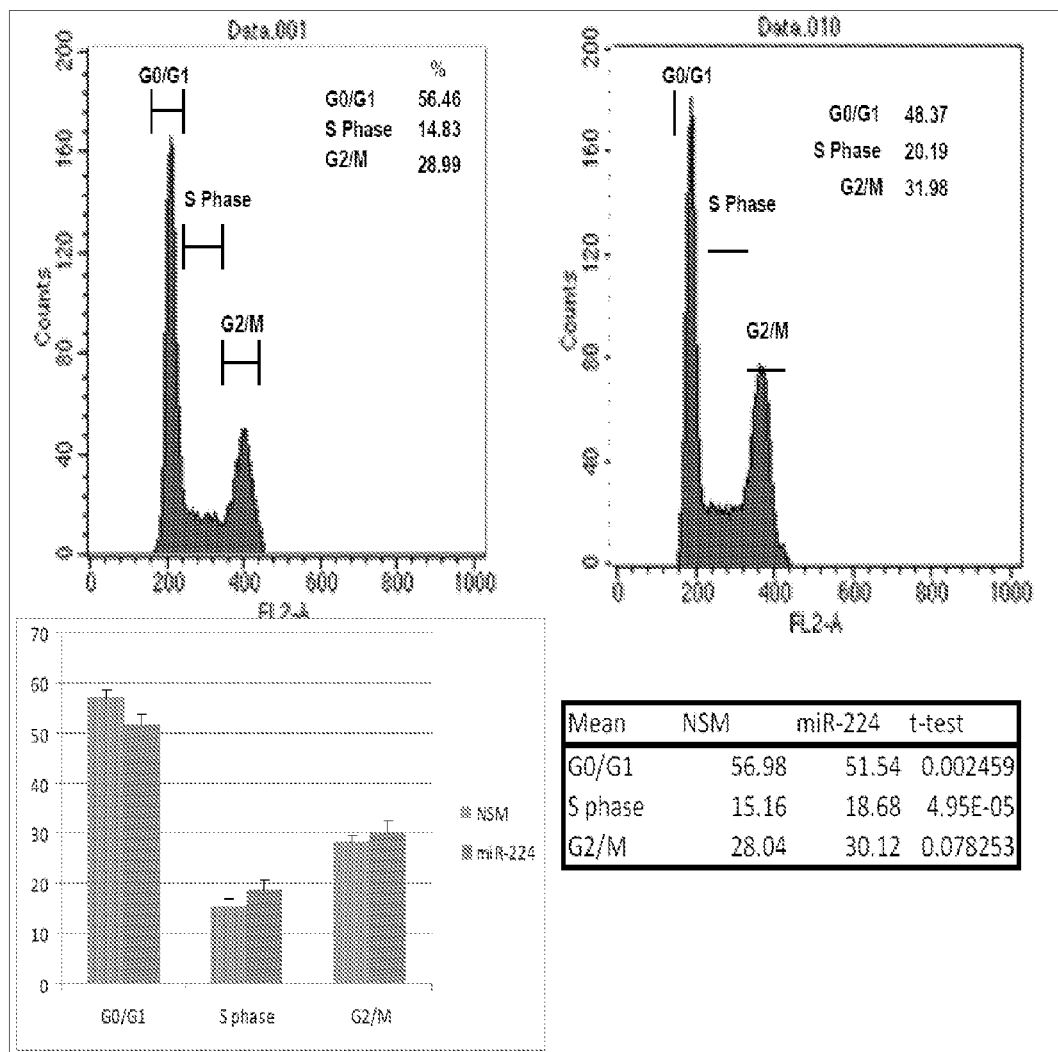
FIG. 13. Cell cycle analysis of H69 human normal epithelial cell lines transfected with miR-224 mimic or nonspecific mimic.
Figure 14:
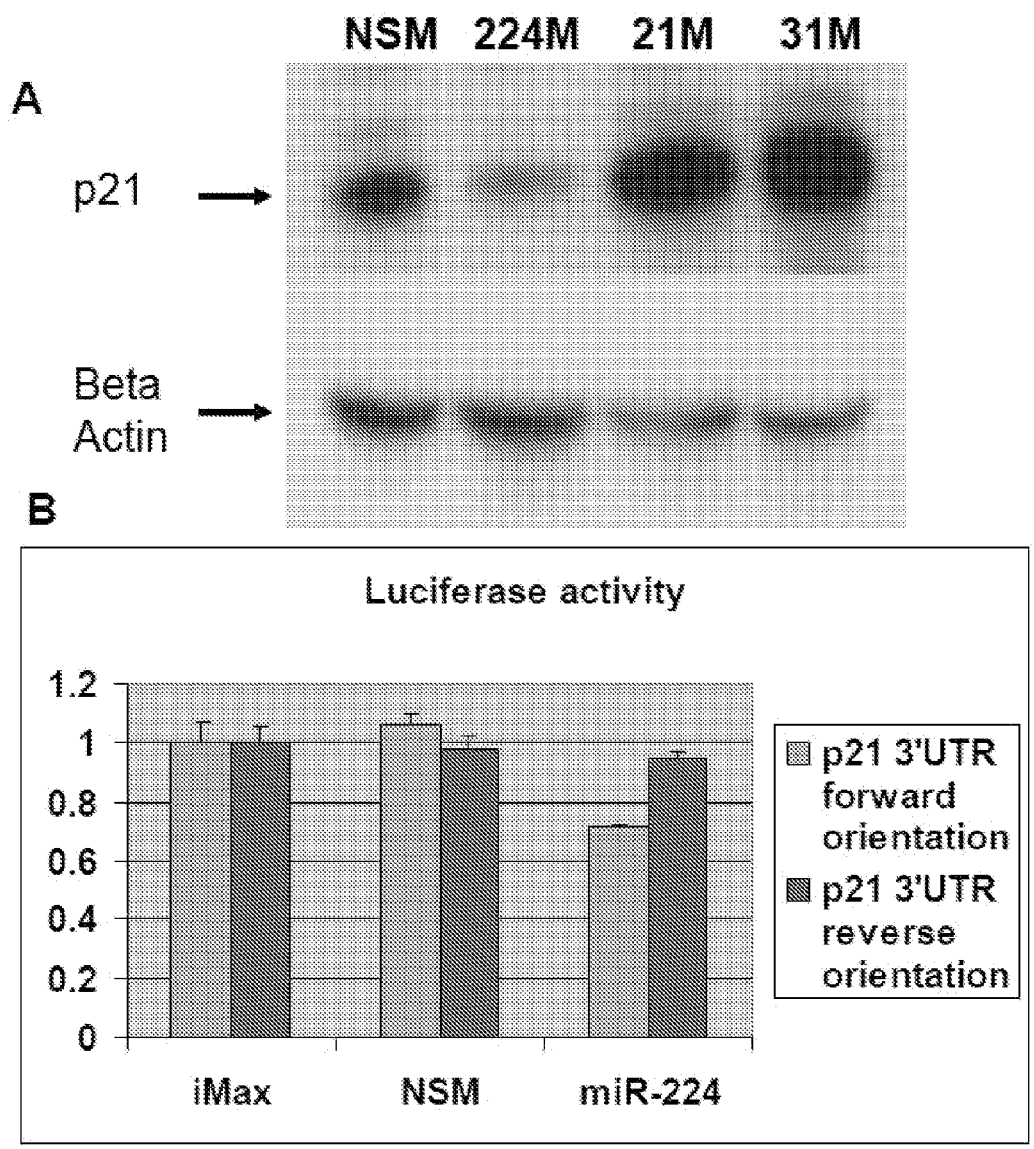
FIG. 14. (A) miR-224 effect on p21 expression. (B) Interaction of miR-224 with p21 3'UTR.
Figure 15:
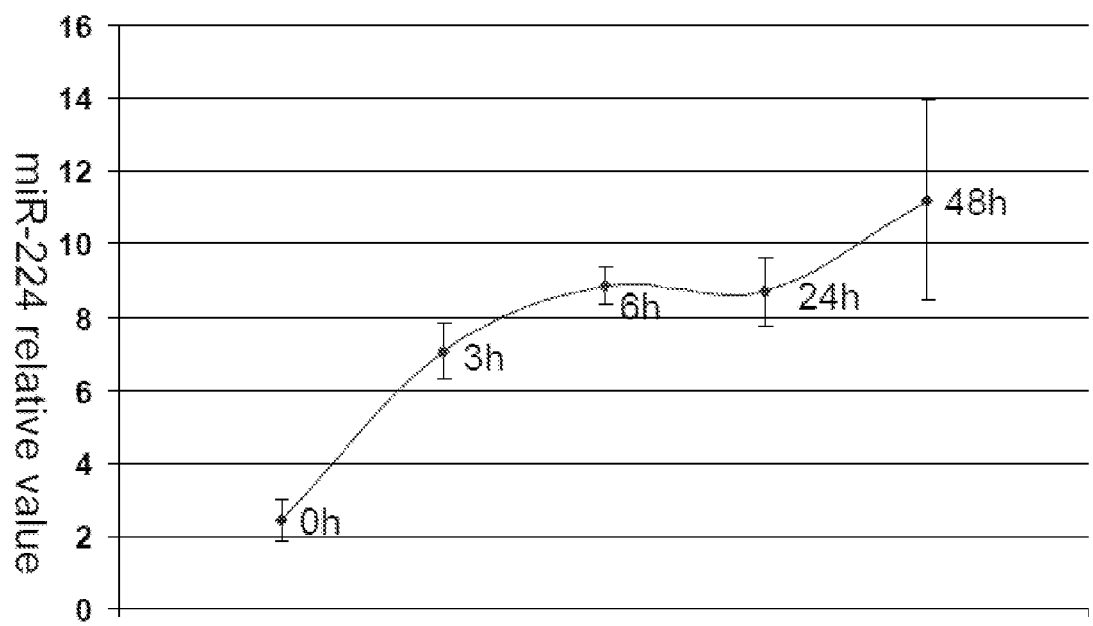
FIG. 15. Effect of IL-6 on miR-224 expression levels.

We have evaluated 5 miR species for their expression across all 178 specimens. We observed that the expression level of miR-224 appeared to be more linearly correlated to the progression from normal to inflammation to cancer, when compared to miR-31. Therefore, suspecting an etiologic role for this miR in this progression, we aimed at identifying mRNA targets for miR-224. In addition, our group's preliminary data in cholangiocarcinoma cells demonstrated that miR-224 exerts a phenotypic impact. More precisely, transfection with miR-224 mimics induced higher proliferation rate in HuCCT1 cholangiocarcinoma cells (data not shown). These data strongly suggest that, along with paralleling the neoplastic progression, miR-224 may play an active role in how neoplasia arises. In a set of preliminary experiments, we aimed at identifying the mechanisms involved with increased proliferation induced by miR-224 in cholangiocarcinoma cells. Cell cycle experiments demonstrated that miR-224 stimulation resulted in a decreased percentage of cells in G0/G1 with a corresponding increase in the percentage of cells in the S-phase (FIG. 13). These data strongly suggest that miR-224 releases the G1-S checkpoint. In conclusion, miR-224 appears to be involved with releasing an important cell-cycle checkpoint, the end result of which is increased proliferation. In addition, insilico searches for targets of miR-224 revealed p21 as a possible candidate. Since p21 is a cycline-dependent kinase inhibitor and functions as a regulator of cell cycle progression at the G1 to S transition, we explored the regulatory effect of miR-224 on its expression. Interestingly, as FIG. 14A demonstrates, the protein levels of p21 are decreased upon stimulation with a miR-224 mimic. To determine if miR-224 reduces p21 protein level by directly interacting with its 3'UTR, we cloned the full length p21 3'UTR in pGL4 luciferase-expressing vector. Compared to nonspecific mimics, cells transfected with plasmids containing p21 3'UTR in forward orientation had significantly lower luciferase activity when cotransfected with miR-224 mimic (FIG. 14B). Reversing orientation of 3'UTR annihilated this inhibitory effect confirming the direct nature of the interaction between miR-31 and the 3'UTR of p21 mRNA. To summarize, our preliminary experiments demonstrated that: 1. miR-224 increases from normal to inflamed, to dysplastic, to cancerous colonic tissue; 2. miR-224 induces increased proliferation in a cholangiocarcinoma cell line (proof of principle experiment performed by our group); 3. the increase in proliferation can be explained by releasing the G1 to S checkpoint (proof of principle experiments in cholangiocarcinoma cells); 4. The release of the G1 to S checkpoint is performed through its direct interaction with the tumor suppressor p21. These data suggest a mechanistic link between inflammation, miR-224 and cancerous transformation. Furthermore, since recent studies also linked IL-6 signaling pathways to the development of IBD and IBD associated neoplasia, we hypothesized that there may be a link between IL-6 and miR-224. To investigate this potential interaction, we treated cholangiocarcinoma cells with IL-6 and measured the level of miR-224. Interestingly, IL-6 stimulation results in a consistent induction of miR-224 (FIG. 15). We therefore propose that the elevated IL-6 levels in IBD may, in part, exert its pro-proliferative effects through stimulation of miR-224, which, in turn, inhibits p21.

The observed dys-regulation of miRs in neoplasia may be explained in two ways: 1. miRs are mere "witnesses" to disease progression and do not play any role in carcinogenesis associated with IBD 2. miRs play a functional role and are involved in malignant transformation. We plan on evaluating the panel of 5 miRs for their etiologic role in cancer development. We believe that through this study we will significantly add to our understanding of cancerous progression in IBD, as well as further define the role of these miRs as disease markers.

We plan on evaluating the 5-miR panel on 2 separate levels. First, we would like to advance our disease marker studies, through verifying the panel on additional specimens. Second, we would like to carefully examine all miRs identified to have dysregulated expression for their contribution to cancer formation in IBD.

A new cohort of 90 specimens will serve as the test set for our miR diagnostic panel. This cohort will be composed of 6 groups containing 15 specimens per group. The 6 groups will be: 1. IBD patients, 2. matched uninflamed specimens from the same IBD patients, 3. IBD dysplastic specimens, 4. IBD-Cancers, 5. sporadic adenomas and 6. SCRCs specimens. qRT-PCR will be performed for all 5 miRs and data will be analyzed based on linear discriminant function. In order to determine whether patients with dysplasia or cancer have IBD-neoplastic associated microRNA alterations in geographically separate, non-neoplastic areas, two additional biopsies, one from the immediate proximity of the lesion and one from the rectum will be collected and miR expression levels will be measured. Our goal is to perform the validation study on biopsies of non-neoplastic IBD, dysplastic IBD, and frankly cancerous IBD, as well as on sporadic colorectal adenoma and adenocarcinoma specimens.

Example 3

Figure 16:
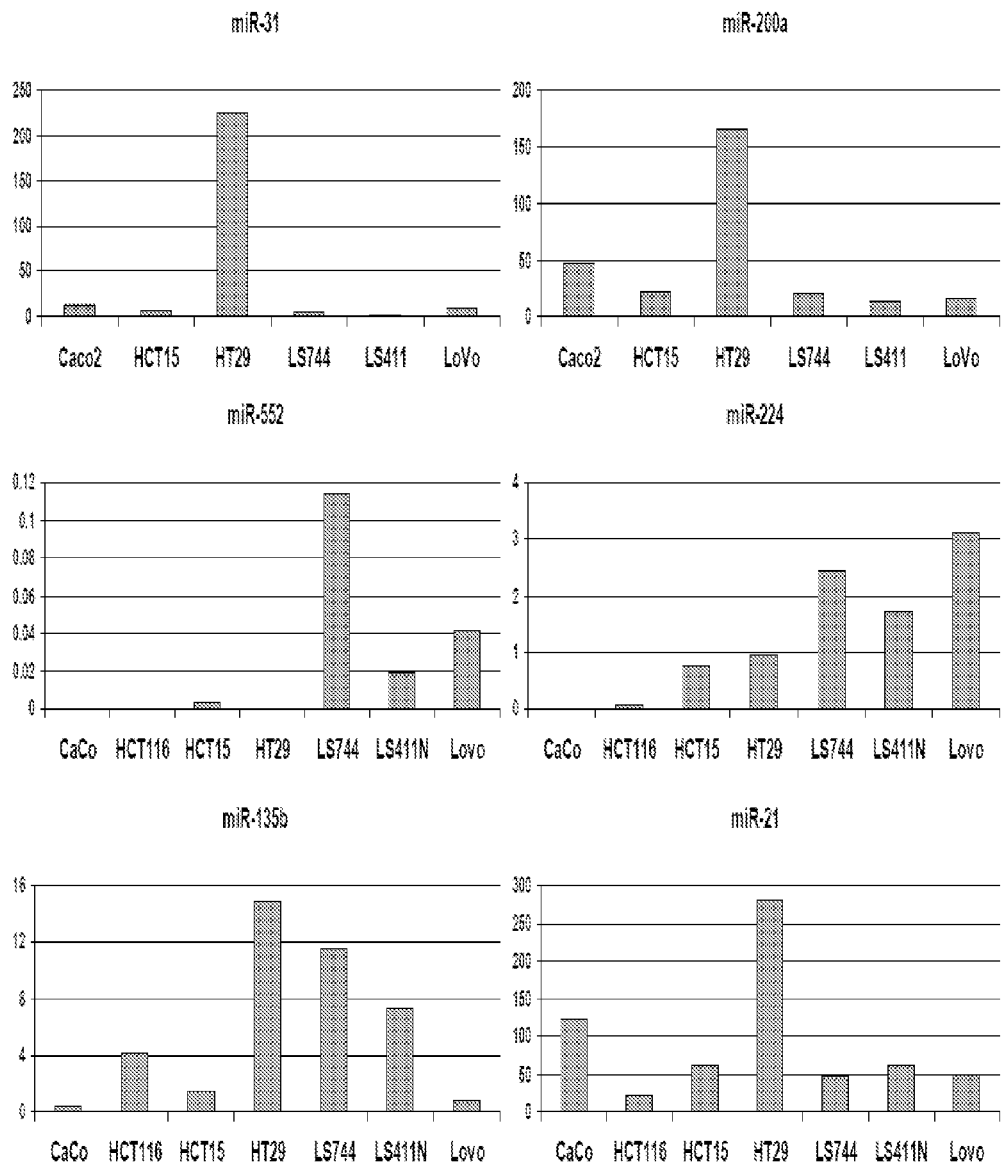
FIG. 16. Mir expression levels in colon cancer cell lines.

Identify the functional role of these miRs in malignant transformation associated with IBD. First, to determine which specific cell types are expressing dysregulated miRs, we will perform in situ hybridization on frozen tissue sections. For miR predominantly localized to epithelial cells, we will modulate miR activity in colon cancer cell lines by transfecting miR mimics or inhibitors. Our candidates for this step include the top five upregulated IBDN miRs and the top three downregulated miRs identified in our array experiments (Table 1B). Additionally, we will clone genomic fragments containing miRs of interest in retroviral viruses in order to stably express miRs via retroviral mediated gene transfer (described in methods section). The effects of manipulating the miR level will be assessed by quantifying proliferation, apoptosis, cell cycle progression, migration and invasion. As a first step we characterized the miR expression levels for the top five IBDN up-regulated miRs identified in our array experiments (FIG. 16). Transfection with miR mimics will be carried out in cells demonstrating low expression of the miR to be studied and in HCT116 DicerKO cells. Similarly, miR inhibition will be performed in cells with high level of expression for the miR of interest.

MiRs that demonstrated oncogenic effects based on cell growth, proliferation, apoptosis, or cell cycle progression in vitro will be selected for further study. MiRs may have a broad impact on the gene expression program of the cells, directly or through signaling pathways or cascades downstream of their direct target genes. Therefore, the global expression profile represents a key step in order to explore the outcomes associated with altered miR expression. For this purpose, we propose to perform expression microarray analysis utilizing a bead-based platform containing 60-mer oligonucleotide probes corresponding to 22,000 genes (Illumina HumanRef-8 v2 Expression BeadChip, Illumina Inc., San Diego, Calif.). This platform possesses superior data robustness due to the employment of the liquid-phase hybridization methodology utilizing multiple probes per each target. To identify pathways affected by the selected miRs, we will perform RNA gene expression array using RNA from Mimic or antagomiR-transfected cells and their appropriate negative controls. Genes with mRNA expression levels inversely correlated with miR-levels will be selected for validation by qRT-PCR and considered as candidates for further studies.

To evaluate the link between miRs and protein levels of their targeted genes, we will measure protein levels by Western blotting in cells transfected with miR mimic or inhibitor cells and their corresponding negative controls. To better define their localization, proteins that demonstrate negative regulation by miRs will also be evaluated in normal, chronically inflamed and IBD-neoplastic tissues by immunohistochemistry. To assess the direct or indirect nature of the effect of miR on protein levels, we will clone the 3'UTR of selected genes in luciferase-expressing vectors and measure the impact of miRs on luciferase activity.

Methods

Cell lines. HCT116/Dicer−/−, CaCo, Lovo, HT29, LS411, LS744, HCT16 and DLD1 cell lines will be used.

Human specimens. For the proposed studies we will collect a cohort of 90 specimens. We are currently accumulating biopsy specimens of IBD neoplasia under an IRB approved protocol. Biopsies are collected from long-standing IBD patients. The Johns Hopkins GI Division is also in the final stages of organizing a Tissue Bank that will collect IBD specimens. We will have full access to all specimens in this Tissue Bank. Research biopsy will be taken from every mass-like or polypoid lesion arising in the colons of IBD patients. An additional biopsy from the same location will also be taken for pathologic examination. These pinch biopsies will be used for secondary validation of our IBDN candidate biomarkers as identified during the first year of this award.

RNA extraction. TRIzol reagent (Invitrogen, Carlsbad, Calif.) will be used to extract total RNA. One hundred nanograms (ng) of total RNA will be used for each microarray and 10 ng for each individual miR-RT-PCR analysis.

Human genome-wide mRNA expression microarrays. Microarray chips containing 60-mer oligonucleotide probes corresponding to 22,000 genes (Illumina HumanRef-8 v2 Expression BeadChip, Illumina Inc., San Diego, Calif.) will be used for expression microarray analysis, to identify differentially expressed genes between cells transfected with miR mimic/inhibitor and their corresponding negative control. Raw output data of each array will be normalized for array-to-array comparison. Fluorescence intensities demonstrating a greater than two-fold difference will be considered significant. The relationship between miR and mRNA will be screened by homology search and will be further studied.

Quantitative RT-PCR (qRT-PCR). The miR test panel will be evaluated by qRT-PCR using TaqMan MiR Assays (Applied Biosystems). U6 small nuclear RNA will be used for normalization, as previously described. For mRNA expression levels, primers will be designed such that PCR product will cross an exon-exon border which overlaps one of the largest introns. Data will be normalized to beta-actin.

Transfections with miR mimics/antagonists. Synthesized RNA duplexes of miR inhibitors and mimics will be purchased from Dharmacon (Lafayette, Colo.). 30~50% confluent cells will be transfected with 60 nM of inhibitor/mimic, or negative control using Lipofectamine RNAi MAX (Invitrogen). RNA and proteins will be harvested 72 hours after transfection.

Retroviral vectors, viral supernatant production and viral transduction. MSCV-based bicistronic retroviral vectors, MIEG3 {Ghiaur et al, 2006 #618} will be used to express miRs. For this, genomic DNA sequence from −200 to +200 of miR of interest will be amplified using PCR primers flanked by EcoRI (5') and XhoI (3') and cloned into the multiple cloning site of MIEG3. The expression of miR will be linked to expression of enhanced green fluorescence protein (eGFP) via internal ribosome entry site 2 (IRES2). The plasmid DNA will be used to generate viral supernatant from Phoenix-gp cells as previously described {Wahlers et al, 2001}. Briefly, Phoenix-gp cells will be grown to 70% confluence in a 9 cm tissue culture treated dish (Corning, Inc., Corning, N.Y.). Eight micrograms of plasmid DNA of interest together with 10 µg MLV gag-pol plasmid and 3 µg VSVG envelope plasmid (Morita et al. 2000) will be cotransfected using Lipofectamine 2000 (Life Technologies, Carlsbad, Calif.) following the manufacturer's protocol. The cells will then be incubated at 37° C. in 5% CO2. Eight milliliters of viral supernatant will be collected every 24 h and stored at −80° C. until used. To stably express miRs via retroviral mediated gene transfer, 1×105 HCCT116 Dicer KO and additional colon cancer cells (with low miR expression) will be plated in each well of a 6-well plate and grown in DMEM overnight at 37° C. and 5% CO2. Subsequently, cells will be incubated with 3 mL of viral supernatant containing 8 mg/mL of hexadimethrine bromide (Polybrene, Sigma-Aldrich, Milwaukee, Wis.). After 6-8 h, the viral supernatant will be discarded and fresh DMEM will be added. Two days after transduction, cells will be harvested and sorted for eGFP expression using a fluorescence activated cell sorter (FACSVantage SE DiVa, Becton Dickinson, San Jose, Calif.).

Cell proliferation assays. Colon cancer cells will be plated at a density of 4×102 per well onto 96-well plates at day 0 (72 h after miR transfection). At every other day until day 6, WST-8 reagent (Dojindo, Mashiki-machi, Kumamoto, Japan) will be added to each well, incubated at 37° C. for 2 h, and then absorbance at OD450 nm will be measured using a plate reader (Molecular Devices, Sunnyvale, Calif.).

Cell cycle analysis by flow cytometry. Flow cytometric analysis of DNA content will be performed to assess cell cycle phase distribution. After transfection of siRNAs at day 0, cells will be harvested at day 3 and stained with propidium iodide using a Cellular DNA Flow Cytometric Analysis kit (Roche Diagnostics). DNA content will be evaluated using an LSR flow cytometer (BD Biosciences, San Jose, Calif.) and CellQuest software (BD Biosciences) for histogram analysis.

Apoptosis assay with Annexin V and PI. Seventy two hours after transfection with miR mimic/inhibitor, cells will be washed twice with ice-cold PBS and then treated for 20 minutes, at room temperature, with 5 uL of Annexin V and 5 uL of PI. Cells will then be analyzed for Annexin V/PI staining within one hour on an LSR flow cytometer (BD Biosciences, San Jose, Calif.).

Cell migration and invasion assays. These parameters will be determined by Transwell and Matrigel chamber plates (24-well-format, BD Biosciences), as described previously. The number of cells migrating through Matrigel inserts are affected by invasiveness through the Matrigel layer itself, as well as by motility through small membrane pores. Invasiveness will be defined as the ratio of the mean number of cells migrating through the Matrigel insert to those migrating through the Transwell membrane.

In situ hybridization with miR probes. In situ hybridization of candidate tsmiRs and oncomiRs will be performed on cryosections of fresh colonic tissue using 5'-end Digoxigenin (DIG)-labeled Locked Nucleic Acid-modified mirCURY specific miR detection probes or a scrambled control probe (Exiqon, Denmark) following the manufacturer's recommendations. Immunofluorescence images will be captured with a Zeiss Axio Imager D1 fluorescence microscope with ApoTome confocal system (Carl Zeiss, Germany).

Immunohistochemistry (IHC). The protein expression levels of candidate genes will be assessed by IHC, using normal, chronically inflamed and IBD neoplastic specimens. Immunohistochemical staining will be performed using a streptavidinperoxidase procedure, following the manufacturer's protocol (Dako Corp., Carpinteria, Calif.).

Western blotting. Protein concentration will be measured using BCA Protein Assay Reagent (Pierce, Rockford, Mass.) 20 ug of protein extracts will be used. Primary and secondary antibodies will be used according to the manufacturer's instructions.

Luciferase reporter assay. Wildtype and mutant 3'-untranslated region (3'-UTR) will be cloned downstream of the firefly luciferase gene in the vector pGL4.13 (Promega). These constructs will be co-transfected with the miRs of interest and their negative controls. Luciferase reporter assays will be performed using a Dual-Glo luciferase assay kit (Promega). Luminescence intensity will be measured by VICTOR2 fluorimetry (Perkin Elmer), and the luminescence intensity of Firefly luciferase will be normalized to that of Renilla luciferase.

qRT-PCR results for our panel of miRs selected for the diagnostic test will be analyzed by employing our linear discriminant function.

Microarray data pre-processing. Pre-processing of raw data, including annotation of bead, global density-based normalization, and generation of average signal intensity of multiple probes corresponding to a target will be performed using BeadStudio software (Illumina Inc., San Diego, Calif.). The steps from RNA amplification to array data pre-processing will be performed at The JHBMC Illumina microarray core facility.

Differential expression analysis. Normalized log2 intensity will be used as the value that represents mRNA expression status of each gene. miR-dependent gene expression status will be assessed by fold difference contrasting miR mimic or inhibitor transfected samples with cells transfected with nonspecific mimic or inhibitor, respectively. A gene will be excluded from the age-dependent differential expression analysis when normalized log2 intensity is not greater than the bottom 5-percentile value for each specimen in all of the specimens.

Our studies identified a unique set of miRs that are able to accurately discriminate IBDN from non-neoplastic colonic mucosae. We will evaluate this miR panel on an independent cohort and anticipate that it will identify the IBDN specimens with a high level of sensitivity and specificity. This panel may become an important clinical tool with impact on the diagnosis, management and ultimate survival of patients with IBD colitis. By identifying targets of such miRs, we may also uncover novel carcinogenetic pathways underlying neoplastic transformation in the setting of IBD. The second aim is sharply focused on mechanisms evaluating the carcinogenic biologic effects and pathways triggered by alterations in miR expression. We expect the proposed research to reveal novel regulatory mechanisms for genes that are functionally and clinically relevant to the unique molecular pathology of IBDN.

Our data suggest that accumulation of abnormal miR expression represent an important molecular event in IBDN. However, there are no studies reporting the carcinogenetic effect of miR alterations occurring uniquely in IBDN. We postulate that a unique set of dysregulated IBDN-miRs exert their carcinogenic effects by altering translation of their cognate target genes. Identification of novel miR targets will reveal additional molecular carcinogenic pathways in IBD that may ultimately serve as targets for future therapeutic or preventive care. Moreover, evaluation of these targets in dysplasia, or nonmalignant colonic mucosa of patients with IBD may lead to the development of early cancer detection biomarkers.

Example 4 miR Dysregulation is Involved in Ulcerative Colitis-Associated Neoplastic Progression.

Primary Inflamed, Dysplastic, Cancerous and Non-Cancerous Colonic Specimens from UC Patients. We have already obtained 79 sets of surgically resected snap-frozen colon cancers or dysplasias (39 UC-cancers and 40 UC-dysplasias), plus their corresponding non-cancerous colonic tissues, from 52 UC patients from the Mount Sinai University School of Medicine (see letter of collaboration from Dr. Noam Harpaz). We have also collected 46 inflamed non-neoplastic specimens from 34 UC patients lacking dysplasia or cancer, along with non-neoplastic, non-UC normal samples of 145 cecal, 93 transverse colon, and 271 rectal mucosae (649 total NC samples from 318 patients). In addition, we anticipate collecting an additional 25-35 UCNs per year from Mt. Sinai (see letter from Dr. Noam Harpaz) and 50 UCNs per year from JHU (see letter from Dr. Susan Gearhart), plus at least 250 non-neoplastic UC specimens annually from JHU (see letters from Drs. Steven Brant and John Kwon). These specimens and their accompanying clinicopathological data were and will continue to be collected under IRB-approved protocols at the two participating institutions. Relevant clinicopathological and demographic data corresponding to all of these specimens have been and will continue to be obtained. This information includes age, gender, anatomic location of tissue, duration of disease, histology, and clinical grade or stage of dysplasia or cancer. Thus, we have or will have enough UCN, non-neoplastic UC, and normal non-UC colon samples from each anatomic region to distinguish expression changes due to anatomic regional variation.

The present inventors sought to identify tumor-suppressive miRs (ts-miRs) and oncogenic miRs (oncomiRs) that are involved in UCN. More specifically, we seek to identify miRs that are dysregulated at each UC-neoplastic stage using miR microarray-based comparisons of non-neoplastic mucosae from non-UC controls vs. UC-associated non-neoplastic mucosa, dysplasia, and carcinoma.

Laser capture microdissection (LCM). We are performing LCM in order to maximize tumor cell purity within UCN specimens. By doing this, we will optimize our ability to detect miR dysregulation in dysplastic or cancerous epithelial cells. We are utilizing 5 adjacent sections of each lesion to maximize total yield.

MiR array data. As a first step toward studying miRs in UCN, we performed miR microarrays on UC-neoplastic rectal tissues vs. control normal rectum (NR). The NR tissues were harvested from patients with no UC or G1 neoplasia history. We hybridized RNAs from 4 UC-tumors and 4 normals to Agilent Human miR Microarrays. Agilent's miR microarray format is 8-plex, allowing for the hybridization of 8 different individual RNAs on a single glass slide. After filtering out miRs that were expressed below background intensity level in all specimens, results were analyzed by significance analysis of microarray data (SAM). Representative results of these comparisons are displayed below:

TABLE 5

Partial list of miRs down- or up-regulated in UC-neoplasias vs. normal rectum

| Downregulated miRs in UCNs vs. NR | | | Upregulated miRs in UCNs vs. NR | | |
|---|---|---|---|---|---|
| Gene ID | SAM Score (d) | Fold Change (NR/UCN) | Gene ID | SAM Score (d) | Fold Change (UCN/NR) |
| hsa-miR-378 | −3.32 | 12.98 | hsa-mir-31* | 1.34 | 456.25 |
| hsa-miR-422b | −4.29 | 4.40 | hsa-miR-552 | 1.48 | 248.66 |
| hsa-miR-338 | −2.05 | 3.81 | hsa-miR-224 | 1.29 | 41.02 |
| hsa-miR-375 | −3.43 | 3.71 | hsa-miR-424 | 1.63 | 21.63 |
| hsa-miR-497 | −2.89 | 3.48 | hsa-miR-182 | 2.15 | 15.07 |
| hsa-miR-192* | −2.83 | 2.95 | hsa-miR-21* | 2.52 | 3.45 |
| hsa-miR-195 | −2.45 | 2.81 | hsa-miR-214* | 1.53 | 2.86 |
| hsa-miR-650 | −1.60 | 2.71 | hsa-miR-93* | 2.16 | 2.08 |
| hsa-miR-215 | −2.55 | 2.68 | hsa-miR-25* | 1.76 | 1.99 |
| hsa-miR-30e-5p | −2.59 | 2.54 | hsa-miR-106b* | 1.24 | 1.43 |

Figure 18:
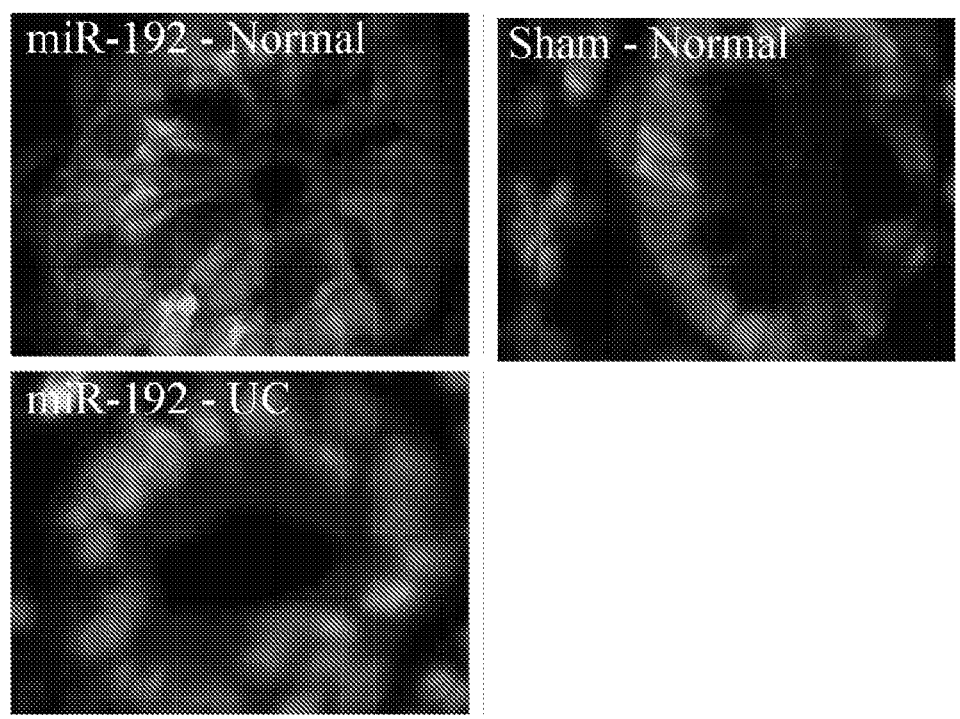
FIG. 18. Localization of miR expression in UC vs. non-UC normal colonic mucosae (NC). In situ hybridization of miR-192 in colonic epithelial cells from NC and UC. Green signal is weaker in UC than in NC. Green=FITC-labeled miR; Red=Hoechst nuclear staining; magnification=×2000. Scrambled (sham) miR probe demonstrated no epithelial localization.

*signifies miRs whose differential expression was individually verified by real-time quantitative RT-PCR (FIG. 18).
NR, normal rectum.
UCNs, UC-associated colorectal neoplasms.
Score (d), SAM index reflecting both the consistency and magnitude of differences between UCNs and NRs.
Negative or positive SAM scores indicate miRs downregulated or upregulated in UCNs vs. NRs, respectively.

A large number of miRs were dysregulated in UCNs vs. control NR. We posit that miRs upregulated in UCNs, the so-called oncomiRs, should downregulate tumor suppressor genes. These oncomiRs per se can ultimately be developed into molecular targets for tumor intervention or prevention by downregulating or blocking their expression.

Furthermore, we seek to confirm dysregulation and epithelial cell localization of prioritized significantly upregulated and downregulated miRs at each UC-neoplastic stage, using qRT-PCR in a larger sample cohort and in situ hybridization assays.

Next, as a proof-of-principle pilot study, we validated our miR microarray results individually for 6 miRs that were significantly upregulated, and 1 that was significantly downregulated, in UCNs vs. noncancerous NR mucosae (hsa-miRs -31, -21, -214, -93, -25, -106b, and hsa-miR-192, respectively; * in Table 5). Using real-time quantitative RT-PCR (qRT-PCR; TaqMan MicroRNA Assays, Human, Applied Biosystems), we analyzed the same UCN and noncancerous UC specimens that we had studied by miR microarray assays. Five-fold serial dilutions of UCCA3 cell line total RNA were used to generate a standard curve for each miR, and values were normalized to U6 small nuclear RNA expression. MiR-31 was at the top of the list of miRs upregulated in UCNs (Table 5) but manifested very low-level expression in all NR samples. Results of these confirmatory qRT-PCRs are displayed in FIG. 17.

Figure 17A:
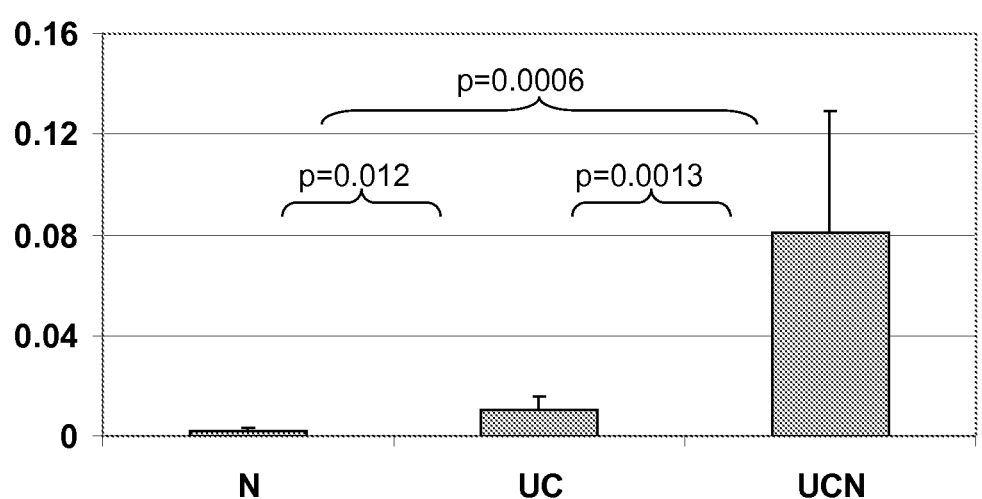
FIG. 17. Quantitative RT-PCR (qRT-PCR) validation of miRs up- or down-regulated in UCNs vs. NRs. TaqMan MicroRNA Assays, Human (Applied Biosystems) were used to confirm miR expression changes identified on miR microarrays between non-UC NR and UC-neoplastic rectal tissues. (a) RT-PCR results for miR-31, according to tissue type (N=normal rectum, UC=inflamed non-neoplastic UC, UCN=UC-associated neoplasia). (b) RT-PCR and miR array for miRs -31, 21, -25, -93, -106b, and -192. Results are relative to NR specimen N1.

RT-PCR performed on the 8 specimens studied by microarray, as well as on 9 additional specimens (6 UCNs and 3 NR biopsies), confirmed microarray results for miR-31, with upregulation averaging 46.31-fold in UCNs vs. control NRs (p=0.0006) (FIG. 17a). We also assessed miR-31 expression in 5 non-neoplastic UC rectal biopsies. UC-neoplasia showed upregulation averaging 7.89-fold (p=0.0012), suggesting that miR-31 upregulation represent a carcinogenesis-specific event.

MiRs -25, -93 and 106b belong to a single miR cluster located on chromosome 7q22, and all three were overexpressed in UCNs on our miR arrays (Table 5, FIG. 17). Moreover, miR-21 was also markedly upregulated in UCNs vs. NRs on arrays (Table 5). qRT-PCR analyses of miRs -31, -21, -25, -93, -106b, -214, and -192 confirmed microarray results (Table 5 and FIG. 17b). Taken together, these qRT-PCR results establish the feasibility and reliability of our miR microarray-based discovery approach.

Levels of some miRs, such as miR-192, were diminished in UC vs. NR (Table 5, FIG. 17b). To determine which specific cell types expressed dysregulated miRs, in situ hybridization of miR-192 was performed on colonic biopsies. Results demonstrated that miR-192 was predominantly localized to normal colonic epithelial cells, but reduced or absent in cells of UC epithelium (FIG. 18).

Next, we sought to determine the biologic impacts of prioritized candidate ts-miRs and oncomiRs in UC-associated neoplastic progression in vitro and in vivo. More specifically, we test the biologic impacts of prioritized dysregulated miRs in vitro by transfecting either miR-mimics (for ts-miRs) or antagomiRs (for oncomiRs) into UCN-derived cell lines, followed by growth, proliferation, cell cycle, and apoptosis assays.

Based on the above RT-PCR and in situ hybridization preliminary data, we selected miRs -25 and -93 for further biologic impact studies, namely, to determine the biologic impacts of prioritized candidate ts-miRs and oncomiRs in UC-associated neoplastic progression in vitro and in vivo.

Figure 19:
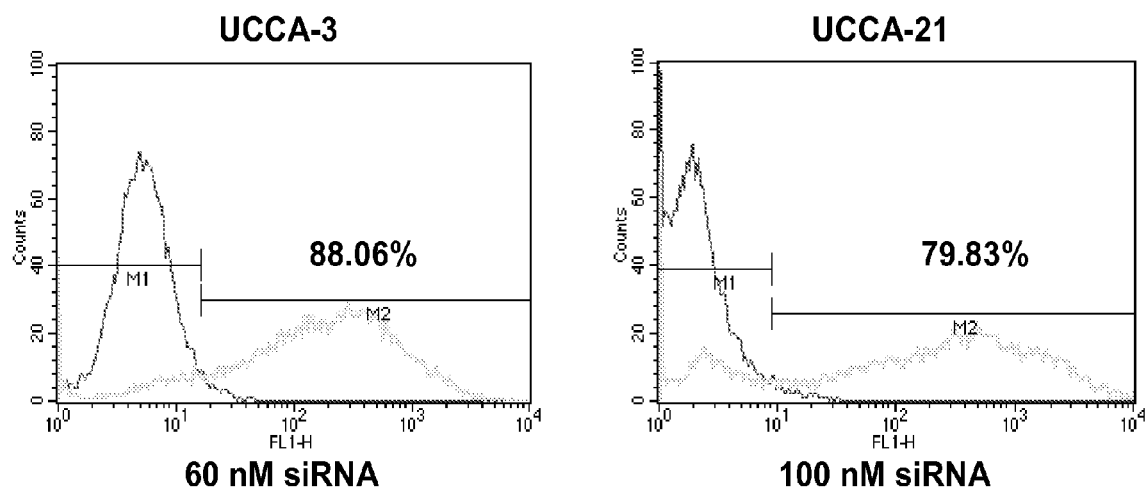
FIG. 19. Transfection efficiencies of a FAM-labeled control siRNA in UCCA-3 and UCCA-21 cell lines. Two representative concentrations (60 nM and 100 nM) of control siRNA are shown. A FAM-labeled control siRNA was transfected at four different concentrations (0, 20, 60 and 100 nM) into UCCA-3 and UCCA-21 cells. Fluorescence intensities in untransfected (blue line) and transfected (green line) cells were measured by flow cytometry. The M1 gate represents the proportion of cells with background fluorescence intensity levels. The M2 gate represents the proportion of cells with higher than background fluorescence intensity levels.

Prior to evaluating any candidate oncomiRs or ts-miRs, one of the key variables potentially affecting our results was anticipated to be transfection efficiency. Therefore, to assess transfection efficiency and to optimize miR-mimic or antagomiR concentrations, we tested 4 different concentrations (0, 20, 60 and 100 nM) of a FAM-labeled control siRNA (siGLO Green, Thermo Fisher Scientific, Inc.) for transfection into the UCN-derived cell lines, UCCA-3 and UCCA-21. Efficiencies of 88% were achieved with 60 nM siRNA in UCCA-3 cells and of 79.8% with 100 nM siRNA in UCCA-21 cells (FIG. 19).

Figure 20:
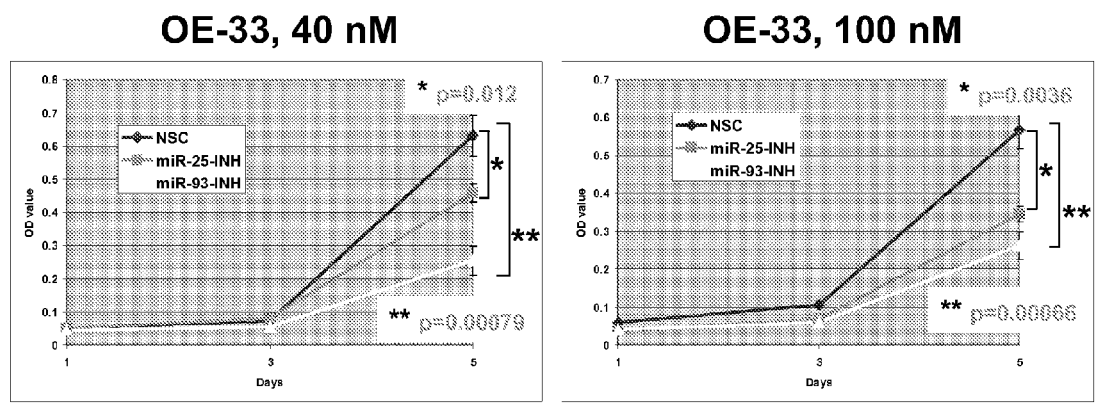
FIG. 20. Cell proliferation assessed by WST-1 assay after miR-25 or miR-93 inhibitor transfection. 1000 OE-33 cells/well (in 96-well plates) were plated on day 0 and transfected singly with either NSC, miR-25 inhibitor, or miR-93 inhibitor. At days 1, 3 and 5, absorbance ($OD_{450}$ nm) was measured after 1 h incubation with WST-1 reagent (Roche, Mannheim, Germany). P-values were calculated by Student's t test. NSC: nonspecific control miR; INH: inhibitor.

Growth inhibition in vitro. We transfected inhibitors (antagomiRs) of native upregulated candidate oncomiRs into OE-33 cancer cells. Native miRs -25 and -93 had been found to be overexpressed in UCN cells (Table 5) and in OE-33 cells (data not shown), so these miRs were selected for inhibition experiments. Indeed, inhibition of miRs -25 and -93 induced highly significant decreases in growth rate (FIG. 20, violet and yellow tracings).

Figure 21:
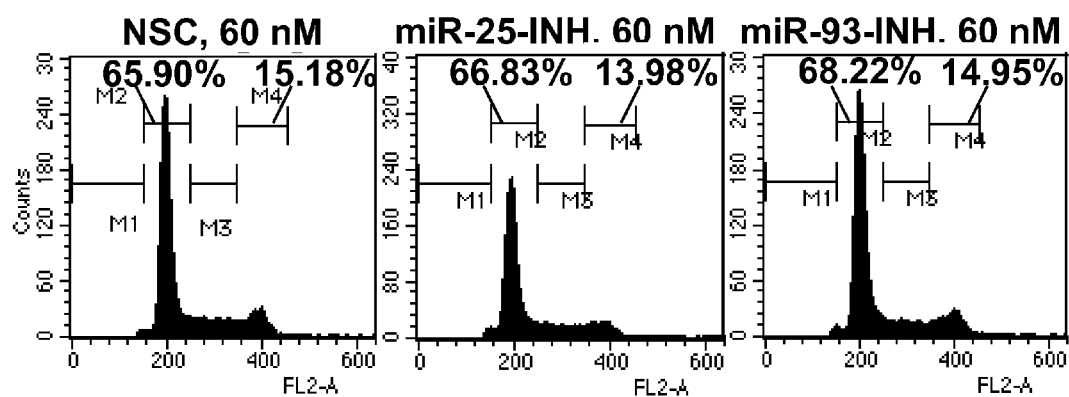
FIG. 21. Effects of miR-25 and miR-93 inhibition on cell cycle progression assessed by propidium iodide (PI) staining $5\times10^5$ cells were transfected with 60 nM NSC, miR-25-INH and 93-INH. After 48 hours, cells were stained with PI and fluorescence intensity was measured using a flow cytometer to assess DNA content. Assays were performed 4 times and p values were calculated by Student's t test. M1, sub-G1 phase; M2, G1 phase; M3, M phase; M4, G2 phase. NSC: nonspecific control miR; INH: inhibitor.

Cell cycle analysis. We performed cell cycle analyses after miR transfection to elucidate the biologic effects caused by inhibiting candidate oncomiRs -25 and -93. In OE-33 cells, miR-25 and -93 inhibitors increased the proportion of cells in G1 and decreased the proportion in G2 phase (i.e., from a control level of 65.90% up to 66.83% (p=0.011) or 68.22% (p=0.0028) respectively in G1, and from 15.18% down to 13.98% (p=0.0027) or 14.95% (p=0.217) respectively in G2 following miR transfection; FIG. 21).

Figure 22:
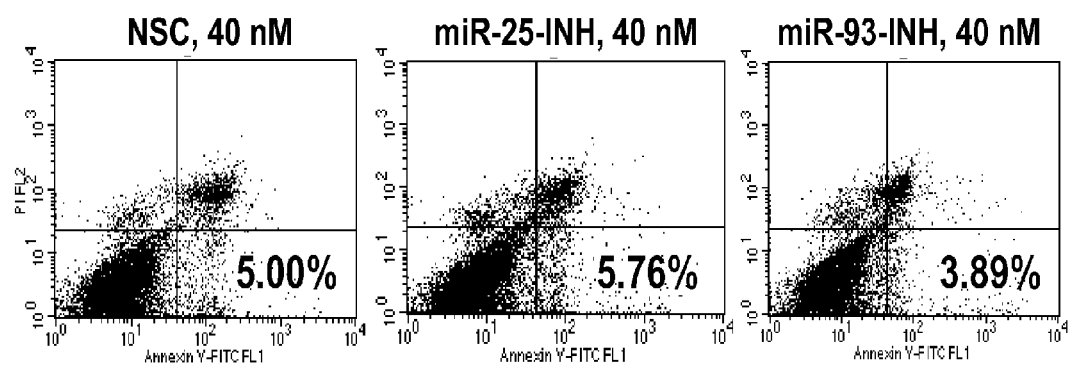
FIG. 22. Effects of inhibiting candidate oncomiRs -25 or miR-93 on apoptosis, assessed by annexin-V assays. $5\times10^5$ cells were transfected with 40 nM NSC, miR-25-INH, or 93-INH. After 48 hours, cells were doubly stained with PI and annexin-V. Fluorescence intensity was measured using a flow cytometer to assess early apoptotic cells, defined as those staining only with annexin-V (lower right window). Percentages designate the proportions of cells in early apoptosis.

Apoptosis assays. We also performed assays of apoptosis due to candidate oncomiR inhibition by transfecting inhibitors of miRs -25 and -93. Examples of apoptosis results obtained with NSC, miR-25 and -93 inhibitors in OE-33 cancer cells are displayed in FIG. 22. Under these conditions, significant changes in apoptosis were not observed. Therefore, we decided to refine our conditions and to perform annexin-V assays at multiple timepoints.

We next sough to test the biologic effects of in vitro effective miRs in vivo by transfecting miR-mimics or antagomiRs into UCN cells and implanting the cells in nude mice.

Figure 23:
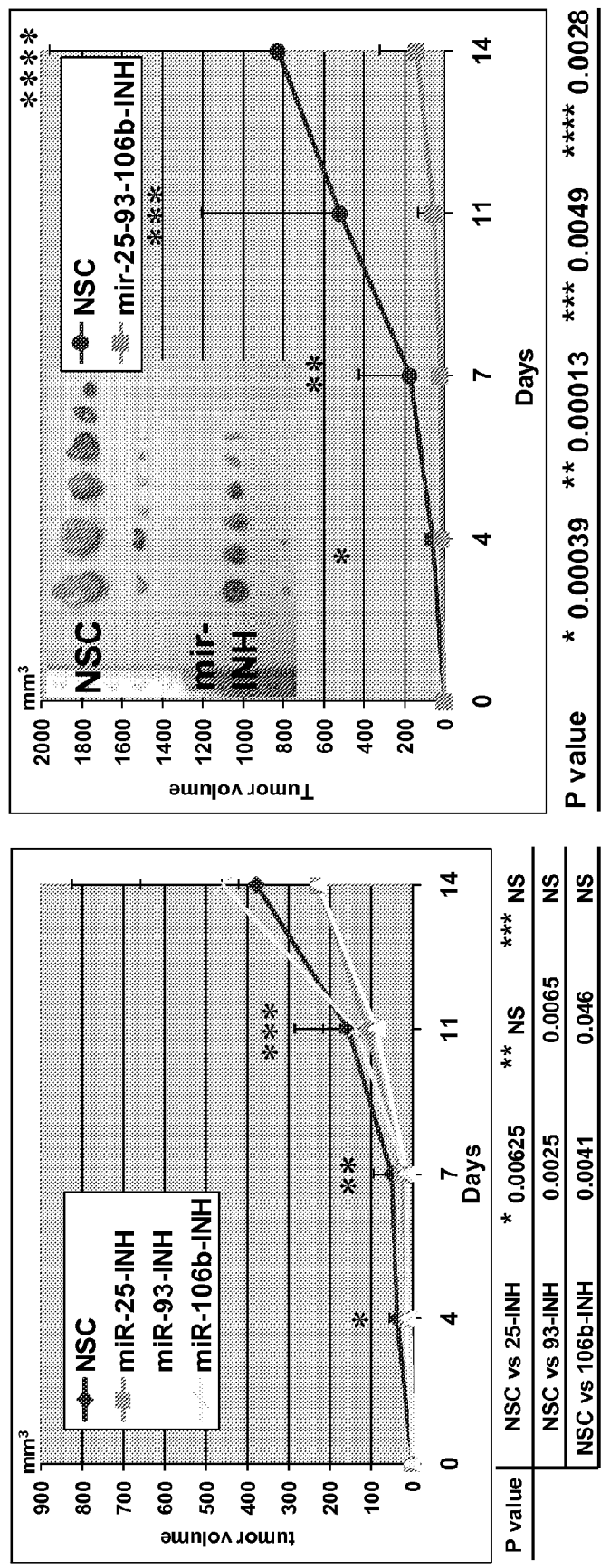
FIG. 23. Effects of candidate oncomiRs -25, -93 and -106b inhibition on tumor growth in vivo. $1.5\times10^6$ SEG-1 cells were transfected with miRs -25, -93 and -106b inhibitors, then implanted 24 hours later into the flanks of nude mice. Tumorigenesis was assessed at days 4, 7, 11 and 14, and tumor size was estimated by the following formula: size=(length)×½× width. P-values were calculated by the Mann-Whitney U-test. (a) (Left panel): 60 nM singly of NSC, miR-25-INH, 93-INH and 106b-INH was transfected (N=6). (b) (Right panel): A combined inhibitor mixture containing 30 nM each of candidate oncomiRs -25, -93, and -106b, or 90 nM NSC alone, were employed (N=12). This antagomiR "cocktail" produced marked inhibition of tumor cell growth in athymic nude mice.
Figure 24:
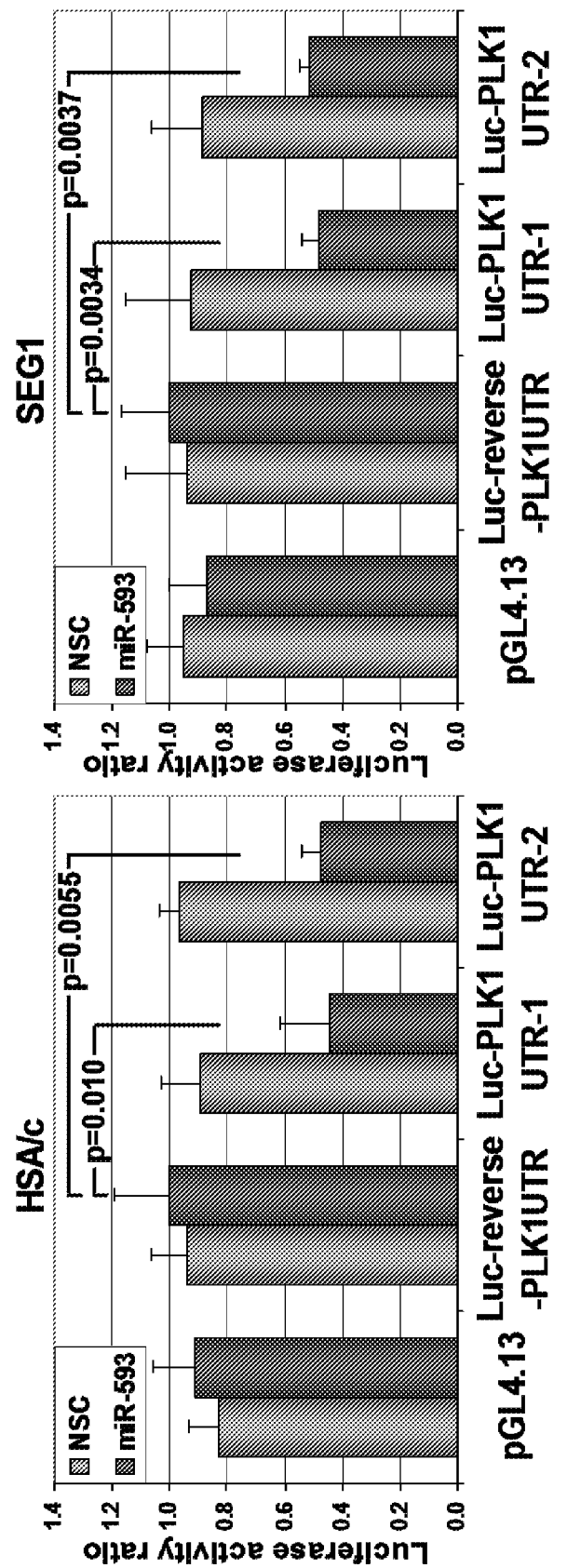
FIG. 24. Luciferase reporter assay after miR-593 transfection in HSA/c and SEG1 cells. Luc-PLK1UTRs (−1 and −2) and Luc-reverse-PLK1UTR are luciferase reporter constructs (pGL4.13) containing full-length PLK1 3'-UTR in correct and reverse orientations, respectively. These constructs were transfected into HSA/c and SEG1 cells 24 h after NSC or miR-593 transfection, and luciferase activities were measured 48 h after miR transfection. Y-axis ratio represents luciferase activity relative to Luc-reverse-PLK1-UTR+miR-593 transfection.

In vivo tumorigenesis. In addition, we showed that antagomiRs to candidate oncomiRs-25, -93, and 106b, all of which were overexpressed in UCNs (Table 5, FIG. 17) exerted inhibitory effects on in vivo tumorigenesis in nude mice (FIG. 23). Synthetic miR-mimics and antagomiRs are effective for up to one week post-transfection. Thus, we expected to obtain more significant results at days 4 and 7 than at days 11 and 14. Interestingly, however, when we used a mixture of antagomiRs, cell growth was markedly inhibited even beyond 7 days, although p-values increased somewhat after this time interval (FIG. 23b).

Using a two-pronged approach, we sought to discover and investigate pathways involving UCN-miRs and their putative cognate UCN-gene transcripts. Starting from candidate miRs, we seek to discover their target gene transcripts by performing mass spectrometric screening of iTRAQ-labeled proteins extracted from UCN cells that have been transfected with candidate miR-mimics or antagomiRs.

iTRAQ data. As an offshoot of our central unifying hypothesis, we postulate that a unique set of dysregulated UCN-miRs exert their carcinogenic effects by altering translation of their cognate target genes (for UCN-oncomiRs, via increased translational silencing of target tumor suppressor mRNAs; for UCN-is-miRs, by decreased translational silencing of oncogene mRNAs). As a proof-of-principle study, we assayed candidate UCN-miRs in OE-33 cancer cells. After transfecting these cells with an inhibitor (antagomiR) of miR-93 (overexpressed in UCNs: Table 5, FIG. 17), we performed iTRAQ to discover downstream mRNA translational regulatory targets of candidate oncomiRs. Since numerous mRNAs are targeted for translational inhibition by each miR, we reasoned that it would be arbitrary, limited, and inefficient to evaluate only one putative target mRNA per candidate UCN-miR. By searching comprehensively for downstream effects of candidate UCN-miRs, rather than focusing on one candidate target mRNA chosen (somewhat arbitrarily) from an in silico miRBASE or TargetScan search, we strove to construct a much more complete and accurate picture of the downstream cellular consequences of candidate UCN-miR dysregulation. iTRAQ assays detected 939 unique proteins induced by antagomiR-93 transfection into OE-33 cells. Most proteins did not change their levels significantly in miR-93 inhibitor (miR-93-INH)-transfected vs. NSC-transfected cells. Proteins upregulated after miR-93-INH transfection were more numerous than downregulated proteins, suggesting that miR-93 inhibition was successful in countering the silencing effect of native miR-93, leading predominantly to gene upregulation, and that at least some of the proteins on this list represented direct miR-93 target mRNAs. Representative results of these experiments are displayed in Table 6.

TABLE 6 iTRAQ analysis of antagomiR-93-transfected tumor cells

| Unused | % Cov | Protein Name | 93-INH/NSC | Gene Name |
|---|---|---|---|---|
| Upregulated proteins | | | | |
| 11.08 | 38.89 | GTPB9_HUMAN | 1.30 | OLA1, GTPBP9, PTD004, PRO2455 |
| 7.52 | 21.68 | K6PP_HUMAN | 1.37 | PFKP, PFKF |
| 5.15 | 12.44 | RL10A_HUMAN | 1.23 | RPL10A, NEDD6 |
| 4.16 | 52.00 | TR112_HUMAN | 1.67 | AD-001, HSPC152, HSPC170 |
| 4.02 | 13.08 | PTRF_HUMAN | 1.26 | PTRF, FKSG13 |
| 4.00 | 11.68 | UBE2T_HUMAN | 1.22 | UBE2T, HSPC150 |
| Downregulated proteins | | | | |
| 4.68 | 15.57 | THIK_HUMAN | 0.80 | ACAA1, ACAA, PTHIO |
| 4.02 | 21.02 | PRS7_HUMAN | 0.72 | PSMC2, MSS1 |
| 4.00 | 14.05 | PEX19_HUMAN | 0.78 | PEX19, HK33, PXF |

MiR-93 was selected for this experiment because of 1) its overexpression in UCNs (Table 5, FIG. 17); 2) its in vitro effects on tumor cell growth (FIG. 20), cell cycle progression (FIG. 21), and apoptosis (FIG. 22); and 3) its inhibition of tumor growth in vivo (FIG. 23). Unused indicates the reliability of protein identifications predicted by homology searches of the SWISS-Plot protein database. In general, values above 2 are considered reliable. % Cov represents what proportion of each identified protein is "covered" by peptide fragments in the protein prediction formula, with higher percentages also suggesting greater reliability of protein identification. 93-INH/NSC, ratio of protein expression in antagomiR-93-transfected vs. nonspecific control miR-transfected cells.

Starting from previously established UCN-related gene transcripts, we document binding of their 3'-UTRs to putative cognate in silico-selected miRs that are also dysregulated in UCNs, using luciferase expression vectors and Western blotting.

Selection of putative UCN-related gene transcripts. We realized that miRs usually downregulate their target genes by binding to mRNA and inhibiting translation. For our definitive miR-mRNA interaction experiments, we will apply iTRAQ and luciferase assays to establish miR-mRNA antecorrelating interactor pairs. Nevertheless, for the purposes of this preliminary miR-mRNA interaction evaluation, we assumed that many of the mRNAs over- or underexpressed in IBDNs vs. NCs would also be similarly dysregulated at the protein level. We therefore consulted our own previous mRNA expression array studies of UCNs, in which we identified a group of genes that was significantly and uniquely dysregulated in this type of neoplasm.

From this preliminary compilation of mRNAs dysregulated in UCNs vs. NCs, we scanned online databases for miRs listing these genes as putative cognate targets. We then cross-referenced all miRs meeting this in silico criterion with our own miR expression array data. MiRs that were counter-regulated relative to their putative cognate UCN-gene targets (upregulated miRs for downregulated UCN-genes; downregulated miRs for upregulated UCN-genes) were interpreted as representing candidate UCN-mRNA binding/interactors.

Targetscan calculated the context score and the context score percentile, which take into account factors beyond complementarity (i.e., site-type contribution, 3' pairing contribution, local AU contribution, position contribution, and sequence conservation across species. Generally speaking, the lower the context score and the higher the context percentile, the higher the likelihood that interaction prediction is correct. This correlation yielded some preliminary predictions of which miRs interact with known or putative UCN-related genes. Genes from these studies showing a greater than 2-fold or a less than 0.5-fold expression ratio in UCNs vs. NCs, sorted in descending order of number of cancer citations, and also showing a t-test p-value for differences between groups of <0.001, are displayed in Table 7.

TABLE 7

Genes significantly and uniquely dysregulated in UCNs, with cognate inversely-regulated miRs.

| candidate UCN gene | | | | | miRs targeting UCN gene | | | |
|---|---|---|---|---|---|---|---|---|
| Symbol | Name- | Refs. | UCN/NC (mRNA) | p value t-test | miR name | context score | context score percentile | UCN/NC (miR) |
| SLC26A2 | solute carrier family 26 member 2 | 3 | 0.01 | 7.7E−05 | miR-31 | −0.21 | 78 | 456.25 |
| | | | | | miR-329 | −0.36 | 98 | 159.74 |
| | | | | | miR-636 | −0.11 | 49 | 90.95 |
| | | | | | miR-382 | −0.14 | 38 | 89.98 |
| | | | | | miR-432 | −0.36 | 97 | 71.18 |
| | | | | | miR-424 | −0.19 | 73 | 21.63 |
| | | | | | miR-21 | 0.01 | 2 | 3.45 |
| FABP1 | fatty acid binding protein 1, liver | 43 | 0.01 | 0.00028 | miR-329 | −0.28 | 94 | 159.74 |
| SLC36A1 | Solute carrier family 36 | 7 | 0.25 | 0.00029 | miR-106a | −0.2 | 71 | 2.07 |
| | | | | | miR-17-5p | −0.2 | 71 | 2.05 |
| | | | | | miR-106b | −0.2 | 71 | 1.43 |
| ARSD | Arylsulfatase D | 39 | 0.33 | 0.00021 | miR-552 | −0.21 | 76 | 248.66 |
| | | | | | miR-659 | −0.26 | 88 | 128.85 |
| | | | | | miR-432 | −0.26 | 90 | 71.18 |
| LRRC4 | Leucine rich repeat containing 4 | 9 | 0.39 | 0.00049 | miR-33 | −0.18 | 69 | 2.23 |
| CDC42BPA | CDC42 binding protein kinase alpha (DMPK-like) | 4 | 0.43 | 8E-06 | miR-181c | −0.36 | 92 | 1.97 |
| | | | | | miR-181a | −0.36 | 92 | 1.63 |
| | | | | | miR-181b | −0.36 | 92 | 1.60 |
| | | | | | miR-181d | −0.36 | 92 | 1.22 |
| MAP3K7IP2 | Mitogen-activated protein kinase kinase kinase 7 interacting protein 2 | 9 | 0.45 | 0.00073 | let-71 | −0.18 | 70 | 1.78 |
| CARD8 | caspase recruitment domain family, member 8 | 6 | 7.87 | 0.00047 | miR-338 | −0.1 | 48 | 0.26 |
| | | | | | miR-650 | −0.05 | 39 | 0.37 |
| | | | | | miR-194 | −0.06 | 11 | 0.49 |
| FBLN1 | fibulin 1 | 34 | 10.46 | 0.00059 | miR-650 | −0.21 | 89 | 0.37 |
| ALDH1A1 | aldehyde dehydrogenase 1, soluble | 16 | 11.34 | 0.00021 | miR-429 | −0.2 | 58 | 0.62 |
| CFB | Complement factor B | 22 | 42.07 | 0.00078 | miR-338 | NA | too close to ORF | 0.26 |

Orange highlighting, mRNAs downregulated in UCNs vs. NCs;
teal highlighting, mRNAs upregulated in UCNs vs. NCs;
Refs., number of articles identified by PubMed search using Boolean operator key words "gene name (or alias)" AND "cancer;" t-test, significance of mRNA expression difference between UCNs and NCs. These putative binding miRs were counter-regulated vs. their cognate UCN-mRNAs.

Preliminary studies of miR downstream pathways. In a proof-of-principle study, we identified miR-593 as a candidate ts-miR (i.e., downregulated) in another experimental system, esophageal cancer cells. We therefore transfected a miR-593 mimic into HSA/c and SEG1, two esophageal cancer cell lines. We determined in silico that the putative oncogene polo-like kinase 1 (PLK1) (33-35) was a predicted cognate target of miR-593. We then established plasmid vectors containing the 3'-untranslated region (UTR) of PLK1, subcloned immediately downstream of the luciferase gene, in order to examine the interaction between miR-593 and the PLK1 3'-UTR. Constructs containing the PLK1 3'-UTR demonstrated 53.9% and 50.2% less luciferase activity than did control constructs in miR 593-expressing

Example 5

Dynamic Changes in the Expression of MicroRna-31 During Inflammatory Bowel Disease-associated Neoplastic Transformation.

Patients with inflammatory bowel disease (IBD) are at increased risk of developing colorectal cancer. Aberrant microRNA (miR) expression has been linked to carcinogenesis; however, no reports document a relationship between IBD-related neoplasia (IBDN) and altered miR expression. In the current study we sought to identify specific miR dysregulation along the normal-inflammation-cancer axis.

miR microarrays and quantitative reverse-transcriptase polymerase chain reaction (RT-PCR) were used to detect dysregulated miRs. Receiver operating characteristic curve analysis was employed to test for potential usefulness of miR-31 as a disease marker of IBDNs. In silico prediction analysis, Western blot, and luciferase activity measurement were employed for target identification.

Several dysregulated miRs were identified between chronically inflamed mucosae and dysplasia arising in IBD. MiR-31 expression increases in a stepwise fashion during progression from normal to IBD to IBDN and accurately discriminated IBDNs from normal or chronically inflamed tissues in IBD patients. Finally, we identified factor inhibiting hypoxia inducible factor I as a direct target of miR-31.

Our study reveals specific miR dysregulation as chronic inflammation progresses to dysplasia. MiR-31 expression levels increase with disease progression and accurately discriminates between distinct pathological entities that coexist in IBD patients. The novel effect of miR-31 on regulating factor inhibiting hypoxia inducible factor 1 expression provides a new insight on the pathogenesis of IBDN.

Materials and Methods

Specimen Collection. Through multicenter collaborations, we established a cohort of 175 fresh-frozen specimens consisting of 55 normal colonic specimens from 14 patients without a history of IBD or cancer, 35 chronically inflamed and 22 noninflamed matched specimens from 35 IBD patients, 11 IBD dysplasias, 37 IBD-cancers, and 15 sporadic colorectal cancers. All specimens were obtained under approved Institutional Review Board (IRB) protocols at the Johns Hopkins University, University of Maryland, and Mount Sinai School of Medicine. Normal tissues were collected from patients with no IBD or gastrointestinal (GI) cancer history. The summary of clinical data for each disease group is illustrated in Table 8. Detailed clinical data for the neoplastic specimens is shown in Table 4.

TABLE 8

Summary of Clinical Data for Individual Disease Groups

|  | IBD-C | IBD-Dys | IBD | N-IBD | N | SCRC |
| --- | --- | --- | --- | --- | --- | --- |
| Age | 49.4 | 57.4 | 46.2 | 48.8 | 60.6 | 68.9 |
| SexM/F | 21/16 | 6/5 | 24/11 | 16/6 | 12/2 | 7/8 |
| IBD type UC/CD/IC | 30/5/2 | 9/2 | 24/11/0 | 15/7/0 | N/A | N/A |
| Location right/left | 12/25 | 5/6 | 5/30 | 18/4 | 26/29 | 3/12 |

N, normal from patients without IBD or colorectal cancer history;
N-IBD, normal "unaffected" specimens from IBD patients;
IBD, "affected" chronically inflamed specimens from IBD patients;
IBD-Dys, dysplastic specimens from IBD patients;
IBD-C, cancer specimens from IBD patients;
SCRC, sporadic colorectal specimens from patients without any history of IBD.

IBD-Dys, dysplastic specimens from IBD patients; IBD-C, cancer specimens from IBD patients; SCRC, sporadic colorectal specimens from patients without any history of IBD; WD, well differentiated; MD, moderate differentiated; PD, poorly differentiated; LGD, low grade dysplasia; HGD, high grade dysplasia; DALM, dysplasia associated lesion or mass.

RNA Extraction. TRIzol reagent (Invitrogen, Carlsbad, Calif.) was used to extract total RNA. One hundred nanograms of total RNA was used for each microarray and 10 ng for each individual miR-RT-PCR analysis.

MiR Microarrays. Microarray assays were performed on eight chronically inflamed and eight IBD-dysplastic specimens using miR Labeling Reagent and Hybridization Kits (Agilent Technologies, Palo Alto, Calif.) and Human miR Microarray Kits (Agilent Technologies). The 100 ng of total RNA from each sample was phosphatase-treated and then labeled with Cyanine 3-pCp. The labeled RNA was purified using Micro Bio-spin columns (Bio-Rad, Hercules, Calif.) and subsequently hybridized to a human miR microarray slide at 55 C for 20 hours. After hybridization the slides were washed with Gene Expression Wash Buffer (Agilent Technologies) and scanned on an Agilent Microarray Scanner using Agilent's Scan Control v. A.7.0.1 software. Raw hybridization intensities were obtained using feature extraction software.

Quantitative Reverse Transcription Polymerase Chain Reaction (qRT-PCR). MiR array results were validated via qRT-PCR using TaqMan MiR Assays (Applied Biosystems, Foster City, Calif.). U6 small nuclear RNA was used for normalization. Quantitative PCR was carried out in duplicate for each sample for both the RNU6B control and each miR.

Statistics. For MiR microarray data, transformation was applied to set all negative raw values at 0.1, A filter on low gene expression was used so that only probes expressed (flagged as present) in at least one sample were kept. Samples were grouped in accordance with their status and compared using Significance Analysis of Microarrays (SAM) using as threshold a minimum of 2-fold difference. qRT-PCR data was analyzed by average fold-change analysis in combination with Student's t-test. Associations between miR expression levels and other tissue demographic parameters (IBD type, IBD disease length and activity, cancer grade or stage, anatomic location, age, and gender) were evaluated using Student's test. We used the area under the empirical receiver operating characteristic (ROC) curve to summarize the ability of hsa-miR-31 qRT-PCR test result to discriminate patients with IBD-related colon cancer or dysplasia from a normal patient or from a noninflamed or chronically inflamed normeoplastic IBD patient specimen. We used bootstrapping with 500 iterations to estimate the 95% confidence interval for the area under the ROC curve.

Transfection of miR Mimic. HCT-116 colon cancer cell lines were used for miR transfections. Synthesized RNA duplexes of miR mimics (agomiRs) were purchased from Dharmacon (Lafayette, Colo.); 30-50% confluent cells were transfected with 60 nM of each miR mimic using Lipofectamine RNAi MAX (Invitrogen, Carlsbad, Calif.). RNA and protein were harvested after 72 hours of transfection. Nonspecific controls for mimics were used as negative controls.

Western Blotting. Cells were lysed in Laemmli sample buffer (Bio-Rad) with a protease inhibitor, (Roche, Basel, Switzerland). Protein concentration was estimated using a BCA Protein Assay kit (Pierce, Rockford, Ill.). Cell lysates (20 ng) were electrophoresed on 10% polyacrylamide gels (Bio-Rad) and transferred to Immobilon-PSQ polyvinylidene difluoride membranes (Millipore, Bedford, Mass.). The membranes were blocked with TBS containing 5% skim milk and 0.1% Tween-20, then incubated with FIH-1 primary antibody from SantaCruz Biotechnology (Santa Cruz, Calif.; Cat. No. sc-26219) For loading control, mouse anti-beta actin monoclonal antibody from Sigma-Aldrich (St. Louis, Mo.; Cat. No. A3854) was used. After washing, the membranes were incubated with the secondary antibody, horseradish peroxidase (HRP)-conjugated donkey antigoat IgG (Santa-Cruz; Cat. No. sc-2056) and analyzed using enhanced chemiluminescence-plus reagent (GE Healthcare, Buckinghamshire, UK). For Western blot quantification, densitometry was carried out using the ImageJ software (National Institutes of Health, Bethesda, Md.).

Luciferase Reporter Assay. A fragment of FIH-1 30-untranslated region (30-UTR) containing two miR-31 predicted binding sites at 105 bp and 767 bp distance from the 50 end of the 30-UTR was amplified from genomic DNA. The primers were designed to contain Nhe 1 and XbaI restriction sites, at the 50 and 30 ends, respectively (ACAGCTAGCCTGCCAGGGGTCAA (SEQ ID NO:1) and TGCCATCTAGAACTACAGCTTCA (SEQ ID NO:2)). The amplicons were cloned downstream of the firefly luciferase structural gene into vector pGL3 (Promega, Madison, Wis.). After ligation, recombinant clones with both orientations were obtained. Plasmid clones with the insert in reverse orientation were used as universal negative controls for the assay. A total of 8000 cells per well were seeded onto 96-well plates on the day prior to transfection, then transfected with miR mimics or inhibitors as described above. The constructed pGL3 vector and an internal control pRL-CMV (Renilla luciferase) vector (Promega) were cotransfected 24 hours after miR mimic transfection using Lipofectamine 2000 (Invitrogen). Twenty-four hours after plasmid vector transfection, the luciferase reporter assay was performed using a Dual-Glo luciferase assay kit (Promega). Luminescence intensity was measured by VICTOR2 fluorometry (Perkin Elmer, Waltham, Mass.), and the luminescence intensity of firefly luciferase was normalized to that of Renilla luciferase. Each treatment condition was performed in four replicates.

Ethical Considerations. Informed consent was obtained from the patients and all specimens were collected under approved IRB protocols at the Johns Hopkins University, University of Maryland, and Mount Sinai School of Medicine.

Results

MiR Microarrays Identify Global miR Alterations. We hypothesized that neoplastic changes in IBD mucosae represent a continuum that culminates with frank colorectal cancer. Furthermore, we hypothesized that the neoplastic progression displays miR signatures unique to each step along the continuum. To identify the earliest changes indicative of neoplastic transformation, we performed miR microarray analyses on eight chronically inflamed and eight IBD-associated dysplastic rectal tissues. After filtering out miRs expressed below background intensity and setting a fold-threshold of 2, we identified 32 miR species that are differentially expressed between inflamed colonic tissue and dysplastic colonic tissue in background of IBD (Table 9). Twenty-two miRs were found to be upregulated and 10 were downregulated in IBD-dysplasia versus inflamed colonic tissues.

TABLE 9

Dysregulated mIRs at the Transition Point from IBD to IBD-related Dysplasia

| Gene ID | Fold Change | Direction of Change | Genomic Location |
| --- | --- | --- | --- |
| hsa-miR-552 | 15.60 | up in IBD Dysplasia | Chromosome: 1; Location: 1p34.3 |
| hsa-miR-31 | 4.60 | up in IBD Dysplasia | Chromosome: 9; Location: 9p21.3 |
| hsa-miR-31* | 4.45 | up in IBD Dysplasia | Chromosome: 9; Location: 9p21.4 |
| hsa-miR-203 | 4.20 | up in IBD Dysplasia | Chromosome: 14; Location: 14q32.33 |
| hsa-miR-215 | 3.81 | up in IBD Dysplasia | Chromosome: 1; Location: 1q41 |
| hsa-miR-135b | 3.55 | up in IBD Dysplasia | Chromosome: 1; Location: 1q32.1 |
| lisa-miR-200b* | 3.46 | up in IBD Dysplasia | Chromosome: 1; Location: 1p36.33 |
| hsa-miR-200a | 3.38 | up in IBD Dysplasia | Chromosome: 1; Location: 1p36.33 |
| hsa-miR-200c | 3.35 | up in IBD Dysplasia | Chromosome: 12; Location: 12p13.31 |
| hsa-miR-194 | 3.33 | up in IBD Dysplasia | Chromosome: 1; Location: 1q41 Chromosome: 11; Location: 11q13.1 |
| hsa-miR-200b | 3.16 | up in IBD Dysplasia | Chromosome: 1; Location: 1p36.33 |
| hsa-miR-192 | 2.98 | up in IBD Dysplasia | Chromosome: 11; Location: 11q13.1 |
| hsa-miR-192* | 2.95 | up in IBD Dysplasia | Chromosome: 11; Location: 11q13.2 |
| hsa-miR-141 | 2.71 | up in IBD Dysplasia | Chromosome: 12; Location: 12p13.31 |
| hsa-miR-96 | 2.65 | up in IBD Dysplasia | Chromosome: 7; Location: 7q32.2 |
| hsa-miR-194* | 2.61 | up in IBD Dysplasia | Chromosome: 1; Location: 1q41/ Chromosome: 11; Location: 11q13.2 |
| hsa-miR-200a* | 2.36 | up in IBD Dysplasia | Chromosome: 1; Location: 1p36.33 |
| hsa-miR-429 | 9:75 | up in IBD Dysplasia | Chromosome: 1; Location: 1p36.33 |
| hsa-miR-375 | 2.24 | up in IBD Dysplasia | Chromosome: 2; Location: 2q35 |
| hsa-miR-424* | 2.16 | up in IBD Dysplasia | Chromosome: X; Location: Xq26.3 |
| hsa-miR-183 | 2.15 | up in IBD Dysplasia | Chromosome: 7; Location: 7q32.2 |

TABLE 9-continued

Dysregulated mIRs at the Transition Point from IBD to IBD-related Dysplasia

| Gene ID | Fold Change | Direction of Change | Genomic Location |
|---|---|---|---|
| hsa-miR-224 | 2.09 | up in IBD Dysplasia | Chromosome: X; Location: Xq28 |
| hsa-miR-892b | 3.64 | down in IBD Dysplasia | Chromosome: X; Location: Xq27.3 |
| hsa-miR-122 | 2.61 | down in IBD Dysplasia | Chromosome: 18; Location: 18q21.31 |
| hsa-miR-223 | 2.53 | down in IBD Dysplasia | Chromosome: X; Location: Xq12 |
| hsa-miR-501-5p | 2.33 | down in IBD Dysplasia | Chromosome: X; Location: Xp11.23 |
| hsa-miR-146b-5p | 2.31 | down in IBD Dysplasia | Chromosome: 10; Location: 10q24.32 |
| hsa-miR-142-3p | 2.31 | down in IBD Dysplasia | Chromosome: 17; Location: 17q22 |
| hsa-miR-139-5p | 2.10 | down in IBD Dysplasia | Chromosome: 11; Location: 11q13.4 |
| hsa-miR-155 | 2.08 | down in IBD Dysplasia | Chromosome: 21; Location: 21q21.3 |
| hsa-miR-1288 | 2.04 | down in TBD Dysplasia | Chromosome: 17; Location: 15788702-15788776 |
| hsa-miR-490-3p | 2.02 | down in IBD Dysplasia | Chromosome: 7; Location: 7q33 |

Samples were grouped in accordance with their pathological status and compared using SAM software. A threshold of minimum 2-fold difference was used as exclusion criteria.

Figure 25:
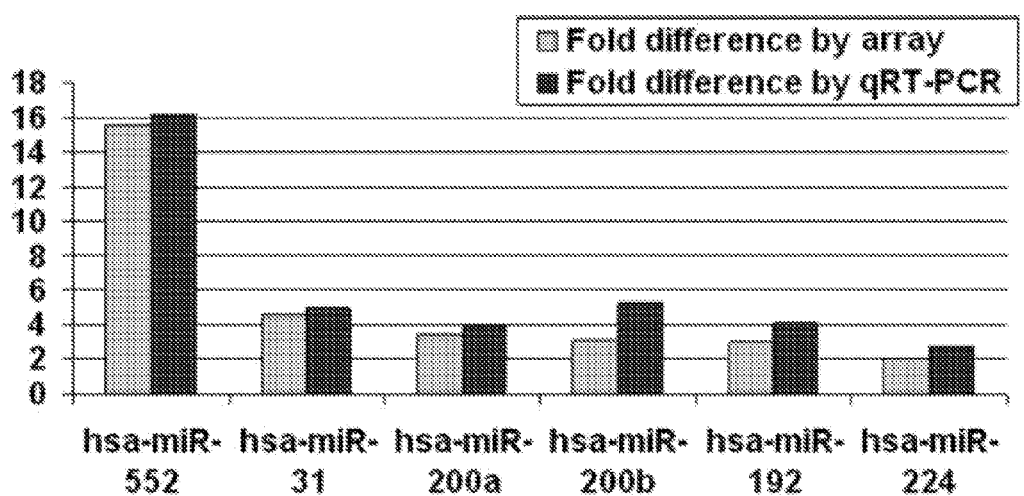
FIG. 25. Validation of miRNA array results by qRT-PCR. RNA from the same samples used for miRNA array analyses was used as a template for qRT-PCR. Signal obtained for qRT-PCR and miRNA array was averaged for the ulcerative colitis and ulcerative colitis-associated dysplasia groups. Fold difference between the two groups is displayed.
Figure 26:
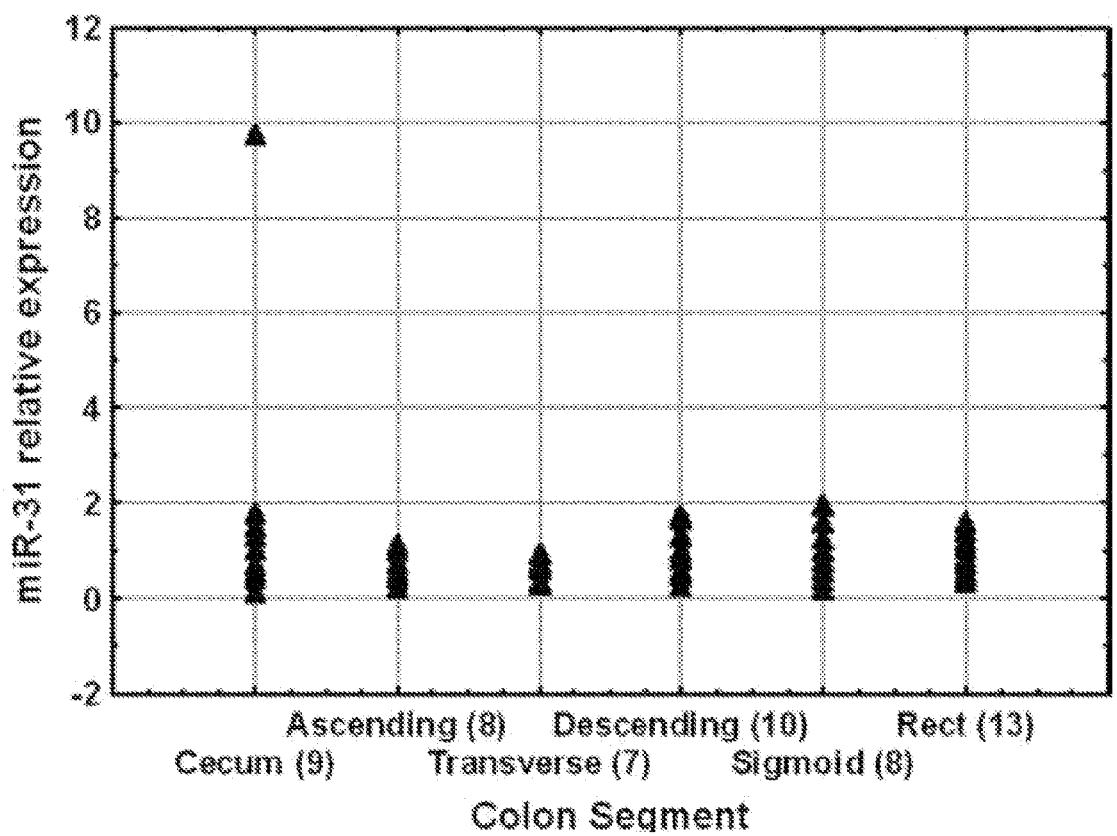
FIG. 26. MiR-31 relative expression levels along the normal colon. RNA was extracted from 55 normal specimens collected from patients without any history of IBD or colon cancer. qRT-PCR was performed and signal average for normal specimens was calculated. Values displayed are relative to normal average value. The numbers of specimens for each colon segment are shown in brackets.

Real-time Quantitative PCR Validates Microarray Data. We chose six miR species with differential expression between IBD and IBD-dysplasia specimens and validated their expression by real-time RT-PCR. Furthermore, we assessed the correlation between the fold-differences reported by arrays versus real time RT-PCR. FIG. 25 shows that real-time RT-PCR data confirmed the differential expression for all six miRs. In addition, the fold difference reported by both methods was identical. These data establish both the feasibility and the reliability of our miR microarray-based screening strategy.

miR Expression is Independent of Colonic Segment. There are significant genetic differences between right- and left-sided normal mucosae as well as between sporadic colorectal tumors arising in different colonic regions, suggestive of a different biologic predisposition to neoplastic transformation. 14 In order to establish a baseline miR expression level throughout the colon, we evaluated the expression level of miR-31 in several colonic segments. We hypothesized that miRs do not change in normal colonic mucosae and, therefore, altered miR expression will likely reflect a diseased state, rather than location bias. Alternatively, if miR expression changes from one normal colonic segment to another, then miR level in a diseased state needs to be compared to the level of miR in normal colon from the same segment. RNA from 55 specimens obtained from 14 patients with no history of IBD or GI cancer was used to perform real-time RT-PCR for miR-31. FIG. 26 demonstrates that the expression level of miR-31 was similar between normal mucosace specimens from cecum, ascending, transverse, descending, sigmoid colon, and rectum. No statistical differences among the six anatomic location groups were observed.

Figures 27A, 27B:
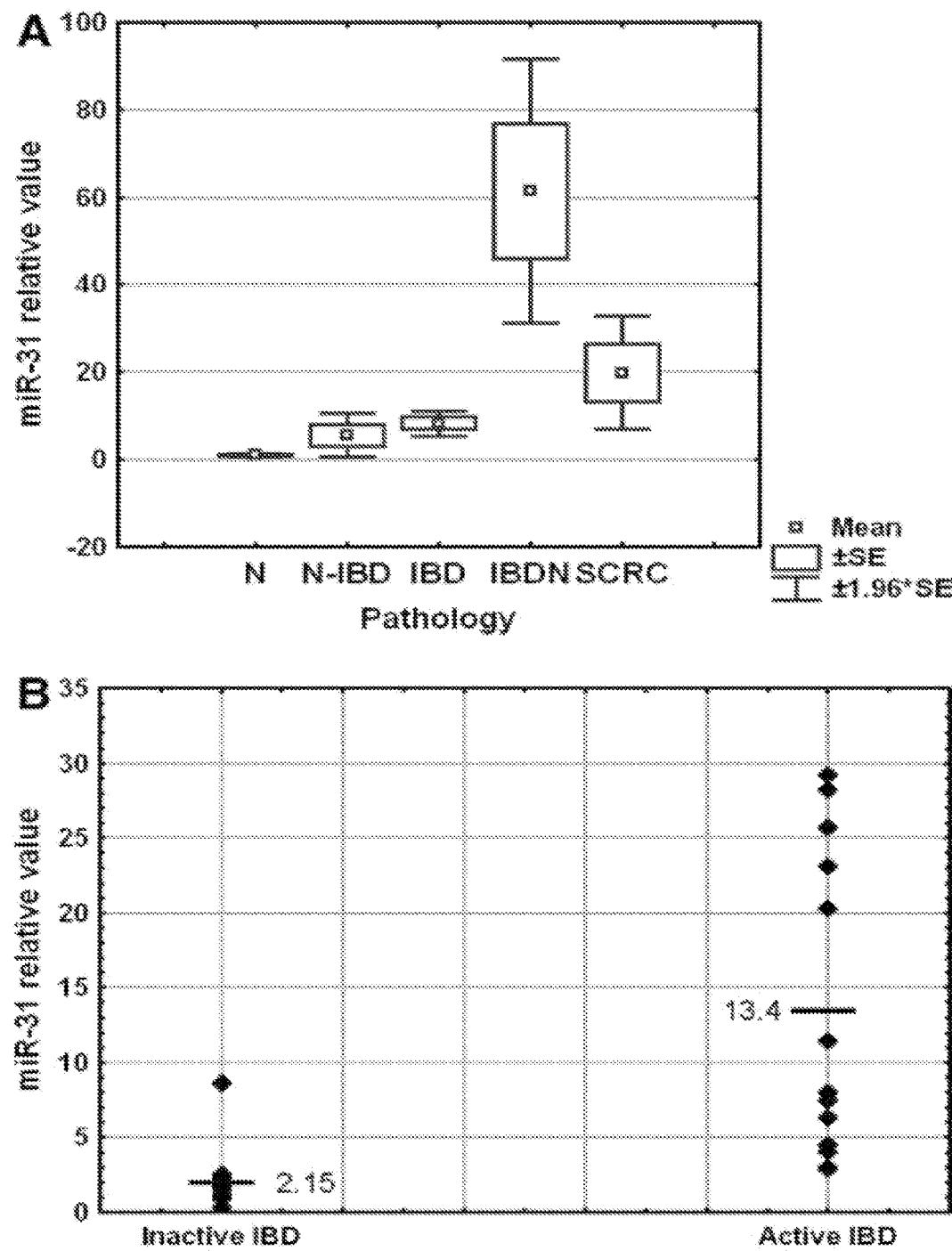
FIG. 27. (A) Dynamic changes of miR-31 expression levels during IBD-related neoplastic transformation. qRT-PCR was performed using as template total RNA extracted from 175 patient specimens. Samples were grouped according to their pathologic status and the average value for each group was calculated. N ¼ normal from patients without IBD or colorectal cancer history; N-IBD ¼ normal 'unaffected' specimens from IBD patients; IBD ¼ 'affected' chronically inflamed specimens from IBD patients; IBDN ¼ neoplastic specimens from IBD patients; SCRC ¼ sporadic colorectal cancer specimens from patients with no history of IBD. Fold differences relative to the average for normal specimens group are displayed. Error bars represent standard error of the mean. (B) Comparison of miR-31 status with respect to disease activity. Individual miR-31qRT-PCR levels were grouped according to their pathology. The average value for each group was calculated relative to the average miR-31 level for healthy colon mucosae.
Figure 30A:
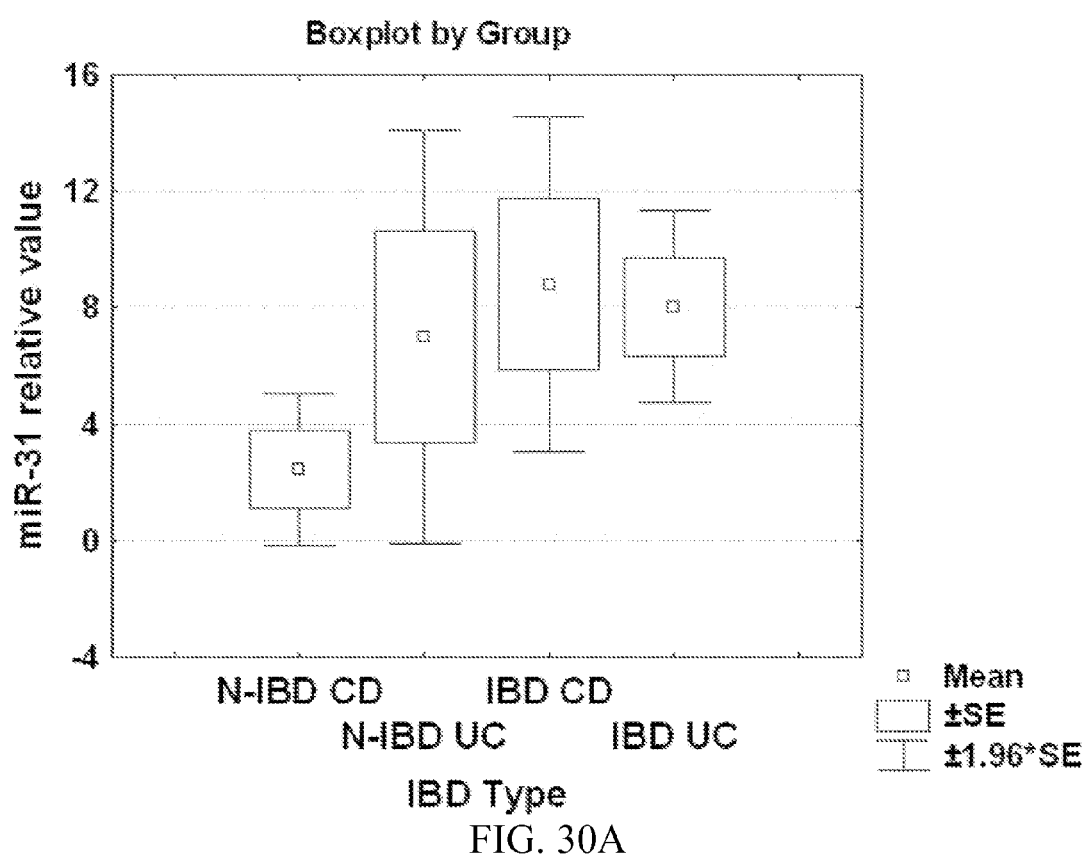
FIG. 30. (A) Comparison of miR-31 status in patients with Crohn's disease vs. ulcerative colitis. N-IBD UC=normal "unaffected" specimens from patients with ulcerative colitis; N-IBD CD=normal "unaffected" specimens from patients with Crohn's disease; IBD UC= chronically inflamed specimens from patients with ulcerative colitis; IBD CD=chronically inflamed specimens from patients with Crohn's disease. (B) Comparison of miR-31 status with respect to disease duration.
Figure 30B:
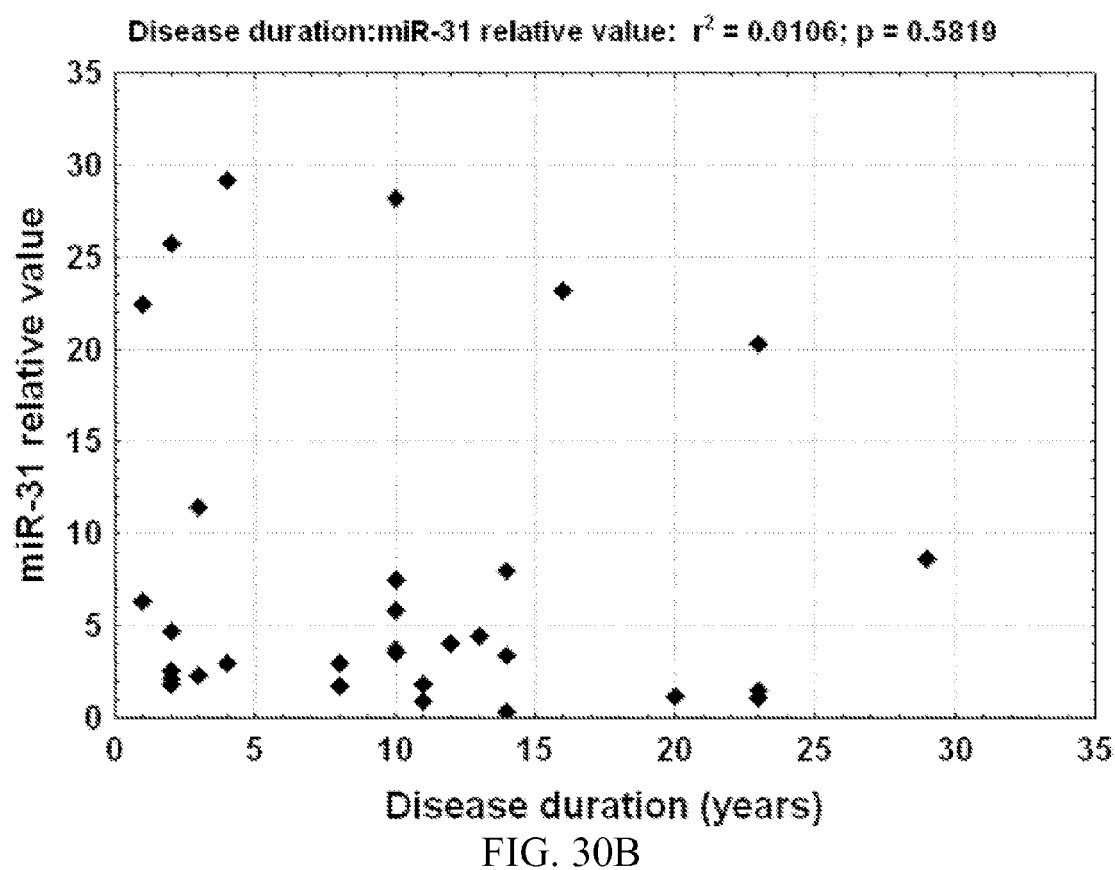

Mir-31 Expression Parallels the Cancerous Progression in IBD. The miRNA array data demonstrated that the expression level of miR-31 increases in the progression from inflamed IBD colonic tissue to dysplasia within IBD colonic tissue. The next question that we addressed was if miR-31 changes at any other transition point in the continuum from noninflamed to inflamed to dysplastic to cancerous colonic tissue from patients with IBD. First, we compared colonic tissue from patients without IBD (N) with normal, unaffected colonic tissue from patients with IBD (N-IBD). MiR-31 was on average 5.5-fold higher in N-IBD versus N (FIG. 27A), although the difference was only marginally significant (P ¼ 0.08, Student's t-test). The difference between N and N-IBD specimens suggests that the harbingers of neoplasia may already be present even in noninflamed colonic tissue from patients with IBD. To further investigate this hypothesis, we compared inflamed colonic tissues from patients with IBD to N. We found that miR-31 is 8.2-fold higher in IBD versus N. This comparison reaches statistical significance (P<0.001, Student's t-test). We further dissected any potential correlations between miR-31 and clinicopathologic data. We obtained information regarding disease activity for 25 IBD patients. In patients with active IBD, miR-31 exhibited a 6.23-fold increase over the quiescent disease group (P ¼ 0.002, Student's t-test; FIG. 27B). No statistically significant correlations with age, sex, duration of disease, or IBD type were found (FIG. 30A, B, and data not shown).

Figure 31A:
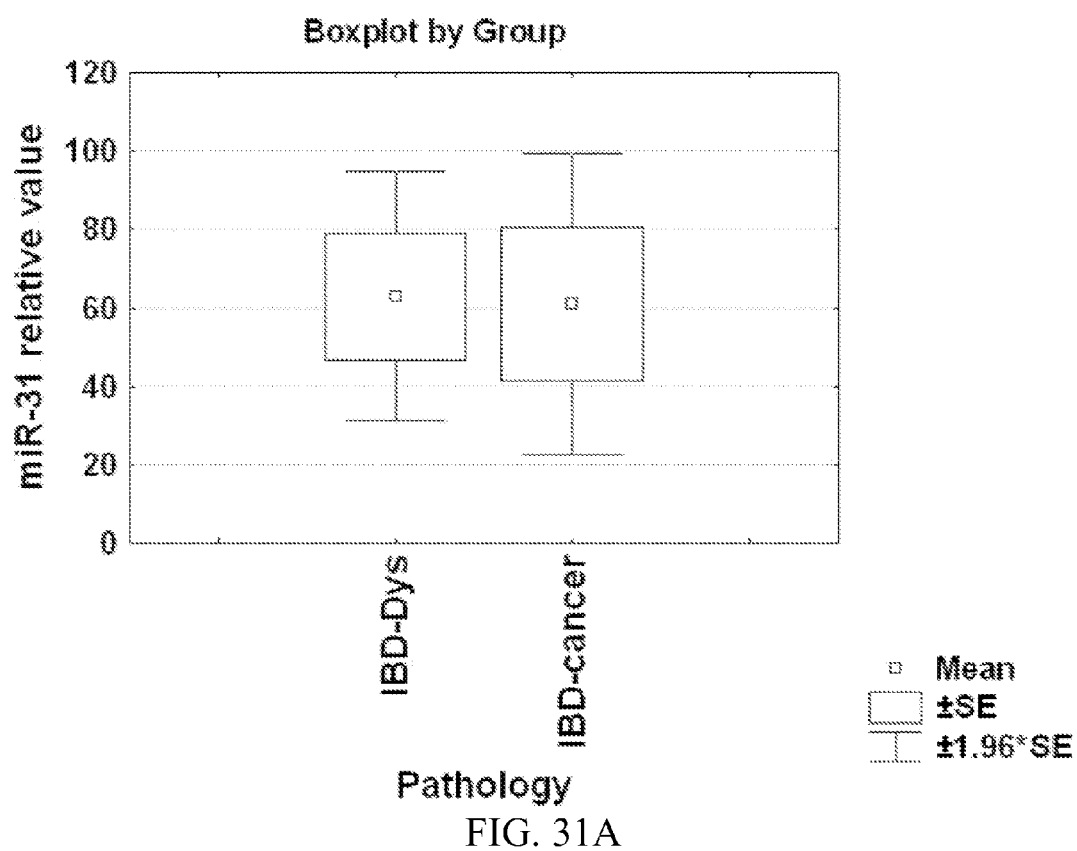
FIG. 31. (A) Comparison of miR-31 status in dysplastic vs. cancerous specimens from patients with IBD. IBD-Dys=dysplastic specimens from IBD patients. Error bars represent standard error of the mean. (B) Comparison of miR-31 status in neoplastic specimens from patients with underlying Crohn's disease vs. ulcerative colitis. IBDN UC=neoplastic specimens from patients with ulcerative colitis. IBDN CD=neoplastic specimens from patients with Crohn's disease. Error bars represent standard error of the mean.
Figure 31B:
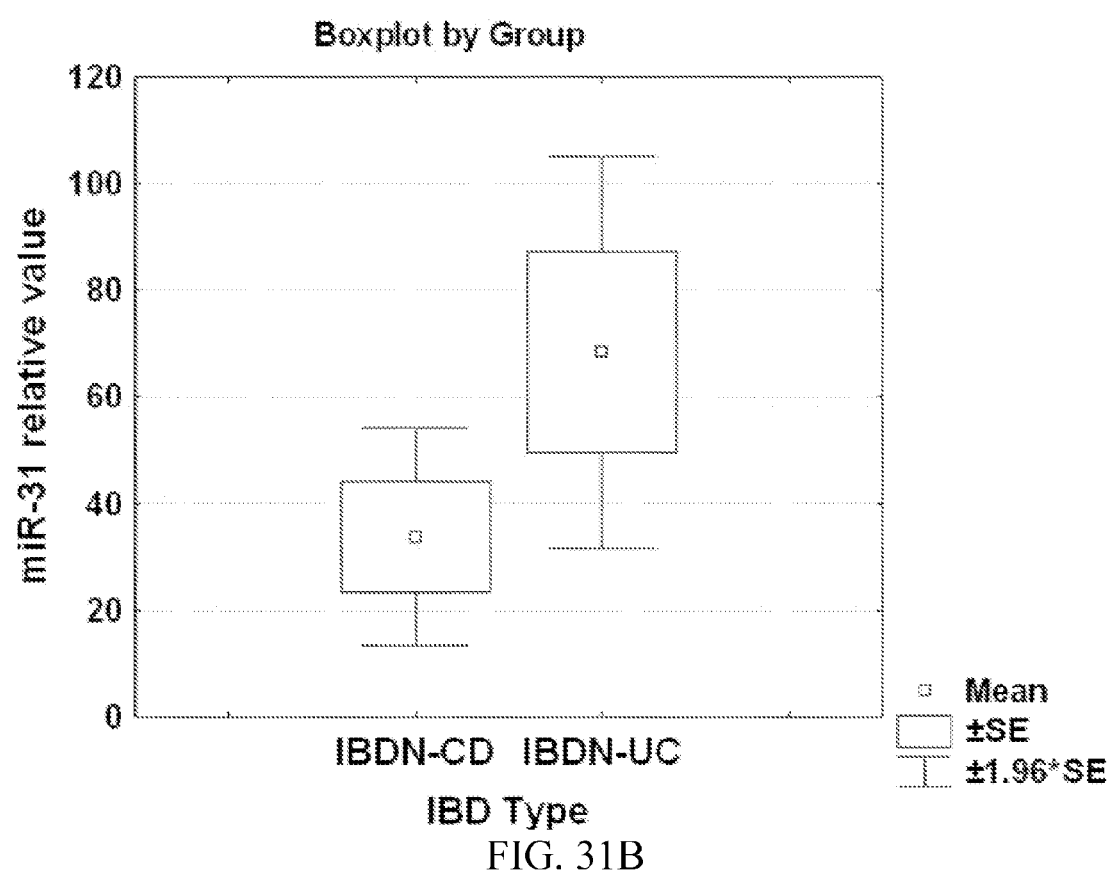

Next, we assessed miR-31 expression in a cohort of specimens with dysplasia and frank colon cancer arising in IBD. No difference in miR-31 expression was noted between the IBD-dysplasia and IBD-carcinoma (FIG. 31A). This finding suggests that miR-31 upregulation is an early event in the neoplastic transformation. From this point on we grouped all neoplastic tissues together. Within the IBDN group no correlation was observed between miR-31 level and age, sex, or underlying IBD type (FIG. 31B, and data not shown). Overall, miR-31 was 61.38-fold higher in IBDN (P<0.001, Student's t-test) compared with normal colon specimens from healthy patients and 11 times higher in IBDN versus IBD (P<0.001, Student's t-test; FIG. 27A). Taken together, these results suggest that miR-31 exhibits a stepwise progression from normal to chronic inflammation to neoplasia.

MiR-31 Accurately Differentiates Sporadic from IBD-associated Colon Cancer. The pathogenesis and multistep progression of IBD-induced colon carcinogenesis differ from that of sporadic colorectal cancer. 15-17 In agreement with our findings demonstrating elevated levels of miR-31 in IBDN, miR-31 was reported to be overexpressed in sporadic colorectal cancer versus normal colonic specimen. Nevertheless, while miR-31 overexpression appears to represent a common event in colorectal carcinogenesis, regardless of its pathogenesis (i.e., sporadic versus IBD-associated), no published studies have yet directly addressed miR-31 in IBDNs versus sporadic colorectal cancers. Therefore, we first determined miR-31 expression levels in 15 sporadic colorectal cancers specimens. We confirmed that miR-31 expression is significantly increased in sporadic colorectal cancers compared to normal specimens (19.8-fold difference; P ¼ 0.013, Student's t-test; FIG. 27A). Next, we compared expression levels of miR-31 in IBDNs directly with levels in sporadic colorectal cancers. MiR-31 expression was significantly higher in IBDNs than in sporadic colorectal cancers (3-fold difference; P ¼ 0.016, Student's t-test).

Figure 28:
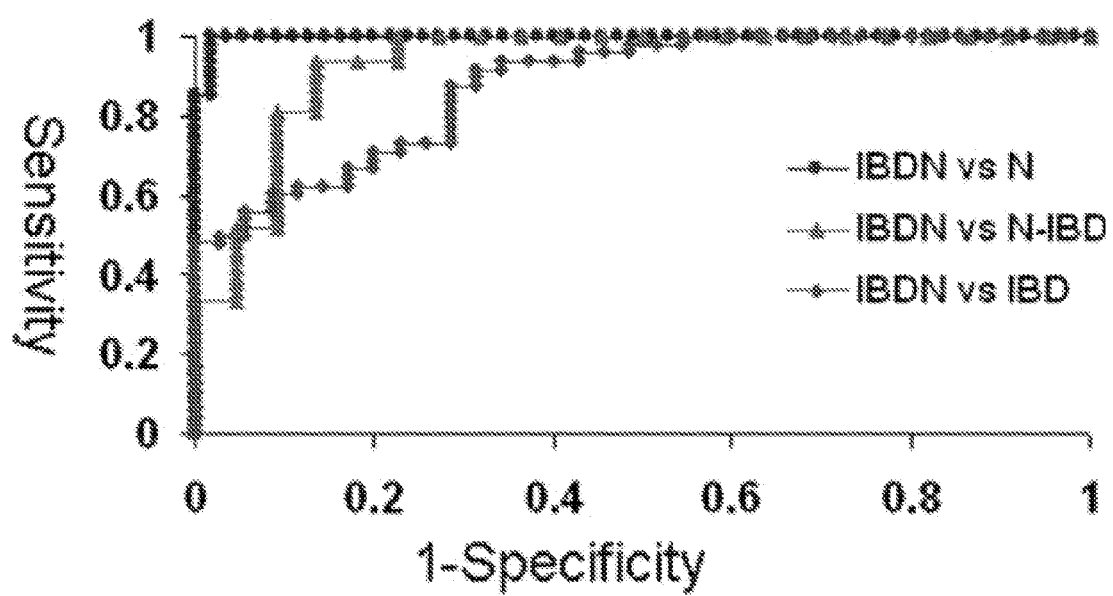
FIG. 28. ROC curve analysis of miR-31 expression levels determined by qRT-PCR. Individual miR-31 qRT-PCR levels were grouped according to their pathology. N ¼ normal from patients without IBD or colorectal cancer history; NIBD ¼ normal 'unaffected' specimens from IBD patients; IBD ¼ 'affected' chronically inflamed specimens from IBD patients; IBDN ¼ neoplastic specimens from IBD patients. Area under the ROC curve and optimal sensitivity and specificity for each comparison are shown.

MiR-31 is a Marker of Cancerous Transformation in IBD. Next, we evaluated the potential clinical utility of miR-31 expression as a disease marker for neoplasia in IBD (FIG. 28). MiR-31 sharply differentiated IBDNs from completely normal colonic mucosae (Ns), as demonstrated by an area under the ROC curve (AUROC) of 0.997 (sensitivity 100%, specificity 98.2% at the point on the curve closest to the origin) for miR-31 qRT-PCR. In our comparison of IBDNs versus "unaffected" normeoplastic IBD (N-IBDs), the AUROC was 0.933 (sensitivity 100%; specificity 77.3% at the point on the curve closest to the origin) for miR-31 qRT-PCR; while in our comparison of IBDNs versus inflamed but normeoplastic IBD (IBDs), the AUROC was 0.877 (sensitivity 87.5%, specificity 71.4 at the point on the curve closest to the origin). These findings further demonstrate the strict correlation between miR-31 expression and step-wise progression from normal to inflammation to cancer in IBD. They also suggest potential usage of miR-31 as a biomarker of inflammatory-neoplastic progression in IBD.

Figure 29:
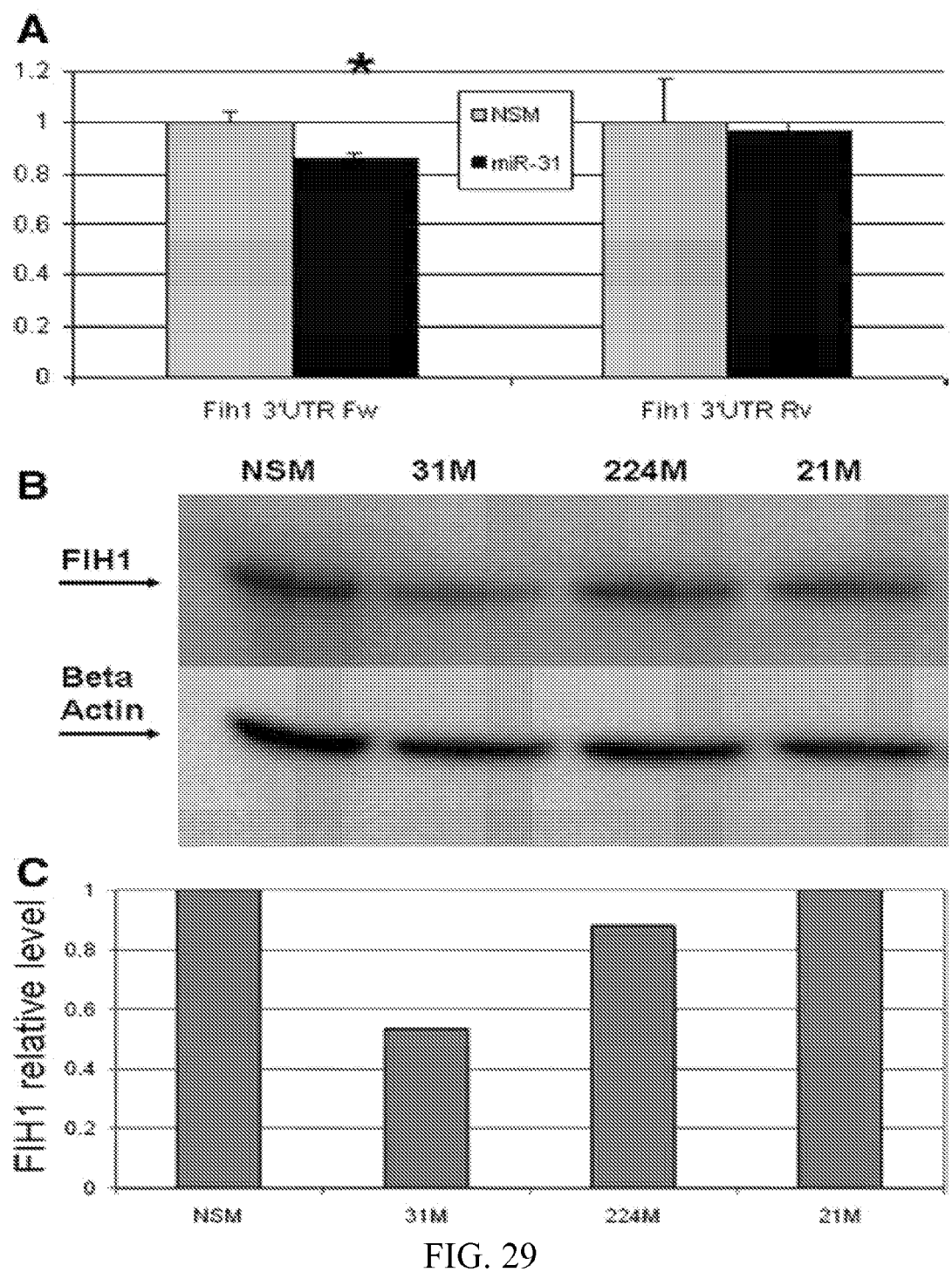
FIG. 29. (A) Interaction of miR-31 with FIH-1 30-UTR. HCT-116 colon cancer cells were transfected with miR-31 mimic or a nonspecific control mimic (NSM). After 24 hours, cells were cotransfected with a construct containing a truncated FIH-1 30-UTR containing two miR-31 putative binding sites fused to the firefly luciferase gene. As a negative control, the 30-UTR was cloned in reverse orientation. When FIH-1 30-UTR forward orientation was used, a moderate but statistically significant difference was observed in miR-31-transfected cells compared to the nonspecific mimic. This inhibitory effect disappeared with inversion of the FIH-1 30-UTR. (B) Effect of miR-31 on FIH-1 protein levels. Western blotting was performed on cells transfected with miR-31. As a negative control, cells were transfected with either 1) a nonspecific mimic; 2) miR-21 (which has no predicted binding site in the 30-UTR of FIH-1); or 3) miR-224 (which does have one predicted binding site within the FIH-1 30-UTR). (C) Quantification of FIH-1 protein levels. Densitometry of Western blots was carried out using ImageJ software.

FIH-1 is a Direct Target of miR-31. MiRs negatively regulate gene expression by binding to complementary sequences within the 30-UTRs of their targets and inhibiting protein translation.5 In silico analysis of multiple independent databases using algorithms to predict miR biological targets identified factor inhibiting hypoxia inducible factor 1 (FIH-1) as a candidate target of miR-31. We sought to determine whether miR-31 interacts with the 30-UTR of FIH-1 (FIG. 29A). Compared to nonspecific negative control, miR-31-transfected HCT116 colon cancer cells demonstrated significantly lower FIH-1 30-UTR luciferase activity (14.03%, P ¼ 0.001, Student's t-test). Reversing orientation of the FIH-1 30-UTR did not altered the luciferase activity, confirming the direct nature of the interaction between miR-31 and the 30-UTR of FIH-1 mRNA. To validate the modulating effect of miR-31 on FIH-1 expression, we determined FIH-1 protein levels by Western blotting (FIG. 29B, C). In cells transfected with miR-31, FIH-1 was substantially reduced (46.63%) compared to cells transfected with a nonspecific control miR or with mimics of miR-21 (an miR with no predicted binding site within the 30-UTR of FIH-1) and miR-224 (an miR that does have one predicted binding site within the FIH-1 30-UTR) (FIG. 29B, C). Thus, after determining that miR-31 downregulates FIH-1 protein levels by directly interacting with its 30-UTR, we concluded that FIH-1 represents a direct target of miR-31 in colon cancer cells.

Example 6

MicroRNA-224 Negatively Regulates p21 Expression During Late Neoplastic Progression in Inflammatory Bowel Disease. The development of colon cancer represents a major complication in patients with inflammatory bowel disease (IBD). The importance of microRNAs (miRs) in carcinogenesis is becoming clearer because miRs have been implicated in the regulation of cancer-related cellular processes to include apoptosis, differentiation, cell cycle progression, and immune function. In the current study, we sought to identify miR dysregulation specific to progression along the normal-inflammation-cancer axis in colonic specimens from patients with IBD.

MiR microarrays and quantitative reverse transcription PCR were used to detect and confirm dysregulated miRs. Receiver operating characteristic curve analysis was applied to evaluate the potential use of miR-224 as a neoplastic disease marker in IBD. For miR-224 target messenger RNA (mRNA) identification, mRNA microarrays were employed in combination with bioinformatic analyses, Western blotting, and luciferase activity measurements.

We identified 30 miRs that were differentially expressed between chronically inflamed mucosae and cancers arising from IBD tissues. MiR-224 levels increased successively at each stage of IBD progression and accurately discriminated cancers from normal or chronically inflamed IBD tissues. Moreover, mRNA arrays combined with bioinformatic analyses suggested the participation of miR-224 in cell cycle regulation. Subsequently, cell cycle experiments indicated that miR-224 regulates the G1-S checkpoint. Finally, in silico prediction analyses, confirmed by Western blotting and luciferase assays, identified p21 as a specific direct mRNA target of miR-224.

These findings reveal miR dysregulation specific to IBD-associated colorectal carcinoma. MiR-224 is overexpressed in IBD cancers and targets p21, a key cell cycle regulator. Moreover, these results establish the participation of miR-224 in IBD carcinogenesis.

Materials and Methods

Human Specimens. We evaluated an existing cohort of 162 specimens consisting of 55 normal colonic epithelial specimens from 14 patients without any history of IBD or cancer, 35 chronically inflamed and 23 noninflamed "matched" specimens from patients with IBD, 11 IBD-associated dysplasia specimens, and 38 frank IBD cancer specimens. Relevant clinical and pathologic information for these specimens is available in Tables 4 and 5. All specimens were obtained under protocols approved by the Institutional Review Board at the Johns Hopkins University School of Medicine, the University Of Maryland School Of Medicine, or the Mount Sinai School of Medicine.

RNA Extraction. TRIzol reagent (Invitrogen, Carlsbad, Calif.) was used to extract total RNA. One hundred nanograms of total RNA were used for each microarray, whereas 10 ng of RNA was consumed for each individual miR reverse transcription PCR assay.

MiR Microarrays. Microarray assays were performed on 8 nonneoplastic and 8 IBD-associated cancer specimens using MiR Labeling Reagent and Hybridization kits (Agilent Technologies, Palo Alto, Calif.) and Human miR Microarray kits (Agilent Technologies). One hundred nanograms of total RNA from each sample was phosphatase-treated and then labeled with Cyanine 3-pCp. The labeled RNA was purified using Micro Bio-spin columns (Bio-Rad, Hercules, Calif.) and subsequently hybridized to a human miR. microarray slide at 55° C. for 20 hours. After hybridization, the slides were washed with Gene Expression Wash Buffer (Agilent Technologies) and scanned on an Agilent Microarray Scanner using Agilent's Scan Control version A.7.0.1 software. Raw hybridization intensities were obtained using Agilent's feature extraction software.

Quantitative RT-PCR. MiR array results were validated via quantitative RT-PCR (qRT-PCR) using TaqMan MicroRNA Assays (Applied Biosystems, Foster City, Calif.). RNU6B small nuclear RNA was used as an internal control for normalization, as previously described (34). RNA was diluted to 2 ng/µL, and 10 ng was used as template in each reverse transcription reaction. Quantitative PCR was performed in duplicate for each sample for both the RNU6B control and each miR.

mRNA Microarrays. The Illumina mRNA microarray platform was used for mRNA microarray assays. HCT-116 Dicer-KO cells, a generous gift from Dr. Bert Vogelstein, were treated with miR-224 or nonspecific mimic (NSM). After 24 hours, these cells were treated with doxorubicin (1 μg/mL), and after 48 hours, the cells were harvested, and RNA was extracted. Array assays were performed at the Johns Hopkins Bayview Genomics CORES Facility, as per the manufacturer's protocol.

Transfection of miR Mimics and Inhibitors. Synthesized RNA duplexes of miR mimics were purchased from Dharmacon (Lafayette, Colo.). 30% to 50% confluent cells were transfected with 60 nM of each miR mimic using Lipofectamine RNAi MAX (Invitrogen). RNA and protein were harvested after 72 hours of transfection. Nonspecific controls for mimics, miR-31, and miR-21 species were used as negative controls.

Western Blotting. Cells were lysed in Laemmli sample buffer (Bio-Rad) with a protease inhibitor (PI), Complete, EDTA-free (Roche Diagnostics, Indianapolis, Ind.). Protein concentration was estimated using a BCA Protein Assay kit (Pierce, Rockford, Mass.). Cell lysates (20 ng) were electrophoresed on 10% polyacrylamide gels (Bio-Rad) and transferred to Immobilon-PSQ polyvinylidene difluoride membranes (Millipore, Bedford, Mass.). The membranes were blocked with TRIS-buffered saline containing 5% skim milk and 0.1% Tween-20 and then, incubated with p21 primary antibody (catalog No 337000; Invitrogen). As an internal control, mouse anti-[beta]-actin monoclonal antibody from Sigma-Aldrich Inc. (catalog No. A3854; St Louis, Mo.) was used. After washing, membranes were incubated with the secondary antibody, horseradish peroxidase-conjugated goat anti-mouse IgG (catalog No 626620; Zymed, San Francisco, Calif.) and analyzed using enhanced chemiluminescence-plus reagent (GE Healthcare, Buckinghamshire, UK).

Cell Cycle Analysis by Flow Cytometry. Flow cytometric analysis of DNA content was performed to assess cell cycle phase distribution. After transfection of miRs at day 0, cells were harvested at day 2 and incubated with PI staining buffer (PBS, 0.1 mg/mL; PI, 0.6% NP40) and 2 mg/mL RNase A for 30 minutes on ice (Roche Diagnostics). DNA content was analyzed using FACSCalibur (BD Biosciences, San Jose, Calif.), and Cell Quest software (BD Biosciences, Md.) was used for histographical analysis.

Luciferase Reporter Assays. The full-length p21 3'-untranslated region (3'-UTR), containing one miR-224 predicted binding site, was amplified from genomic DNA using linker primers containing XbaI restriction sites. Amplicons were cut by XbaI and nondirectionally cloned into vector pGL4 at an XbaI site just downstream of the firefly luciferase structural gene (Promega, Madison, Wis.). A mutant p21 3'-UTR was constructed by mutating 3 nucleotides within the "seed" sequence of the miR-224 binding site. Plasmid clones that contained the mutated binding site were used as universal negative controls for these assays. Cells were seeded onto 96-well plates on the day before transfection, then transfected with miR mimics. The constructed pGL4 vector and an internal control pRL-CMV (Renilla luciferase) vector (Promega) were cotransfected 24 hours after miR mimic transfection using Lipofectamine 2000 (Invitrogen). After 48 hours of plasmid vector transfection, a luciferase reporter assay was performed using a Dual-Glo luciferase assay kit (Promega). Luminescence intensity was measured by VICTOR2 fluorometry (Perkin Elmer, Waltham, Mass.), and the luminescence intensity of firefly luciferase was normalized to that of luciferase.

Statistical Analyses. For miR microarray data, transformation was applied to set all negative raw values at 0.1, followed by quantile normalization. A filter on low gene expression was used so that only probes expressed (flagged as present) in at least one sample were retained. Then, samples were grouped in accordance with their status and compared using GeneSpring software. A threshold of minimum 2-fold difference was used as an inclusion criterion. For mRNA expression data, candidate genes were filtered as follows: genes with expression levels below 100 units (the array background level) were eliminated from analysis. Next, we eliminated genes that demonstrated less than a 3-fold change on stimulation with miR-224. At the end of the filtering procedure, from the original 24,527 mRNAs, the list of genes was reduced to 807. These genes were input into Ingenuity Pathway Analysis (IPA) to identify pathways in which they were involved. Quantitative RT-PCR data were analyzed by average fold-change analysis in combination with Student t test. Associations between miR expression levels and other tissue or patient demographic parameters (IBD type, grade or stage, anatomical location, age, and gender) were evaluated using Student t test.

We used the area under the empirical receiver operating characteristic (ROC) curve to summarize the ability of the hsa-miR-224 qRT-PCR test result to discriminate an IBD-associated colorectal cancer from normal colonic tissue of a patient without cancer and IBD or from uninflamed or chronically inflamed nonneoplastic IBD colonic tissue. We applied bootstrapping with 500 iterations to estimate the 95% confidence interval for the area under the ROC curve (AUROC).

Ethical Considerations. Informed consent was obtained from the patients, and all specimens were collected under protocols approved by the Institutional Review Board at the Johns Hopkins University, University of Maryland, and Mount Sinai School of Medicine.

Results

Figure 32:
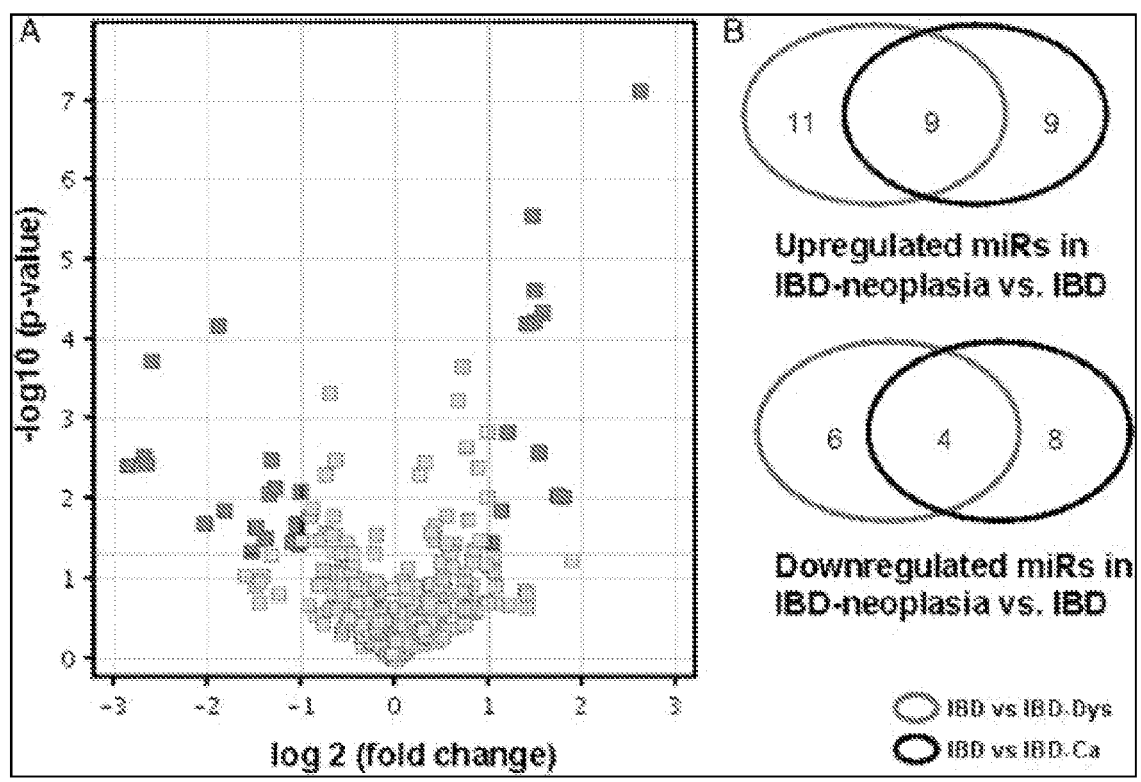
FIG. 32. A, volcano plot illustrating differentially expressed miRs in IBD versus IBD-Ca as determined by miR microarray analysis. Samples were grouped in accordance with their status and compared using GeneSpring software. A threshold of minimum 2-fold difference was used as exclusion criteria. B, Venn diagram showing overlapping of miR dysregulation in IBD-associated dysplasia and IBD cancer. IBD-Ca, cancer specimens from patients with IBD.

MiR Expression Profiles are Altered in IBD-associated Dysplasias and Cancers. To test our hypothesis that miR expression is altered during IBD-associated neoplastic transformation, as well as to identify specific biomarkers of IBD-associated neoplasia, we performed miR microarray analyses on 8 noncancerous IBD tissues and 8 UC-associated cancer tissues. After filtering out miRs expressed below background intensity in all 16 specimens studied, candidate miRs were further prioritized with GeneSpring software, using a P value <0.05 and a >=2-fold change as inclusion criteria. Among the 30 dysregulated miRs selected by these criteria, 18 were upregulated and 12 were downregulated in UC cancers versus nonneoplastic UC specimens. FIG. 32A and Table 10.

TABLE 10

MiRs Dysregulated at the Transition From IBD to IBD-Associated Colorectal Carcinoma

| Systematic Name | P | Fold Difference | Regulation |
| --- | --- | --- | --- |
| hsa-miR-224 | 0.001 | 3.68 | Up in IBD-Ca |
| hsa-miR-135b | 0.002 | 6.05 | Up in IBD-Ca |
| hsa-miR-31* | 0.0028 | 6.40 | Up in IBD-Ca |
| hsa-miR-452 | 0.0032 | 2.51 | Up in IBD-Ca |
| hsa-miR-552 | 0.0036 | 6.26 | Up in IBD-Ca |
| hsa-miR-31 | 0.0037 | 7.22 | Up in IBD-Ca |
| hsa-miR-95 | 0.0073 | 2.44 | Up in IBD-Ca |
| hsa-miR-424* | 0.0080 | 2.02 | Up in IBD-Ca |
| hsa-miR-550* | 0.0085 | 2.55 | Up in IBD-Ca |
| hsa-miR-96 | 0.0135 | 3.52 | Up in IBD-Ca |
| hsa-miR-200a | 0.0196 | 4.06 | Up in IBD-Ca |

TABLE 10-continued

MiRs Dysregulated at the Transition From IBD to
IBD-Associated Colorectal Carcinoma

| Systematic Name | P | Fold Difference | Regulation |
|---|---|---|---|
| hsa-miR-424 | 0.0201 | 2.07 | Up in IBD-Ca |
| hsa-miR-542-3p | 0.0225 | 2.09 | Up in IBD-Ca |
| hsa-miR-7 | 0.0228 | 2.80 | Up in IBD-Ca |
| hsa-miR-214 | 0.0312 | 2.62 | Up in IBD-Ca |
| hsa-miR-335 | 0.0344 | 2.14 | Up in IBD-Ca |
| hsa-miR-1246 | 0.0356 | 2.06 | Up in IBD-Ca |
| hsa-miR-200b* | 0.0453 | 2.90 | Up in IBD-Ca |
| hsa-miR-1288 | <0.0001 | 2.81 | Down in IBD-Ca |
| hsa-miR-1295 | <0.0001 | 2.69 | Down in IBD-Ca |
| hsa-miR-138 | <0.0001 | 2.98 | Down in IBD-Ca |
| hsa-miR-892b | <0.0001 | 6.09 | Down in IBD-Ca |
| hsa-miR-501-5p | 0.0001 | 2.81 | Down in IBD-Ca |
| hsa-miR-760 | 0.0001 | 2.63 | Down in IBD-Ca |
| hsa-miR-1305 | 0.0014 | 2.30 | Down in IBD-Ca |
| hsa-miR-124 | 0.0025 | 2.90 | Down in IBD-Ca |
| hsa-miR-150 | 0.0089 | 3.32 | Down in IBD-Ca |
| hsa-miR-139-5p | 0.0096 | 3.50 | Down in IBD-Ca |
| hsa-miR-146b-5p | 0.0139 | 2.18 | Down in IBD-Ca |
| hsa-miR-122 | 0.0342 | 2.05 | Down in IBD-Ca |

IBD-Ca, cancer specimen from patients with IBD.

In a previous study, we had compared miR expression profiles in IBD dysplastic versus nondysplastic chronically inflamed IBD mucosae. As expected, there was a high degree of overlap between the results of the current and previous comparisons, particularly among miRs with high fold changes (FIG. 32B and Table 15). For example, 6 of the 7 miRs with the highest fold changes in our current study, miR-31, miR-31*, miR-552, miR-135b, miR-200a, and miR-96, were also upregulated in IBD-associated dysplasias versus nonneoplastic IBD samples in our previous study. MiR-892b and miR-139-5p, the 2 most underexpressed miRs in IBD-associated dysplasias in our previous study, were also downregulated in IBD carcinomas versus nonneoplastic IBD specimens in our new data.

Validation of miRs Exhibiting Dysregulation in IBD. We next validated the microarray results by employing qRT-PCR on the same RNA specimens assayed with miR microarrays. For this validation step, we selected the 5 most upregulated miRs in IBD cancer versus IBD, namely, miR-31, miR-552, miR-135b, miR-200a and miR-224. Quantitative RT-PCR results accurately matched microarray results, confirming the upregulation in IBD-related neoplasia for all 5 of these miRs (Table 11).

TABLE 11

Validation of miR Array Results by qRT-PCR

| Systematic Name | IBD-Ca Versus IBD Fold Difference | | P | |
|---|---|---|---|---|
| | qRT-PCR | Array | qRT-PCR | Array |
| miR-224 | 4.76 | 3.68 | 0.0047 | 0.0001 |
| miR-135b | 10.14 | 6.05 | 0.0090 | 0.0002 |
| miR-200a | 2.43 | 4.06 | 0.0260 | 0.0196 |
| miR-31 | 12.24 | 7.22 | 0.1017 | 0.0037 |
| miR-552 | 12.38 | 6.26 | 0.1226 | 0.0036 |

RNA from the same samples used for miR array analyses was used as a template for qRT-PCR.
Signal obtained from qRT-PCR or miR array assays was averaged in the UC and UC-associated cancer groups.
Fold change between the 2 groups is displayed.
IBD-Ca, cancer specimens from patiens with IBD.

Figure 38:
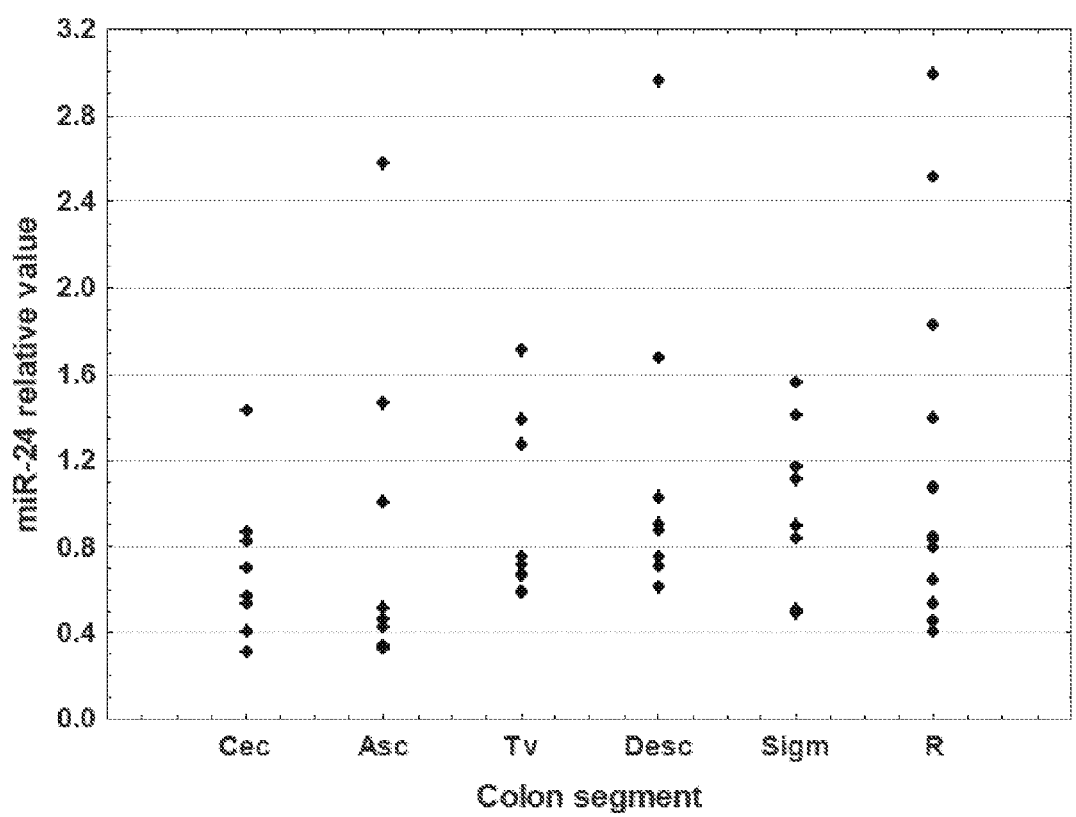
FIG. 38. miR levels throughout normal colon.

MiR-224 Expression is Independent of Anatomical Location. In our miR array screening experiments, miR-224 exhibited the highest statistical significance in discriminating IBD cancers from noncancerous IBD. To verify that miR-224 dysregulation does not reflect sampling error, in the next step, we tested its expression in a larger cohort of colon specimens. This larger cohort included healthy controls as well as IBD, IBD-associated dysplasia, and IBD cancer specimens. As a first step in this analysis, to ensure that anatomical location was not introducing any bias, we evaluated miR-224 expression levels throughout the normal colon. RNA was extracted from 55 specimens obtained from 14 patients who lacked any history of IBD or gastrointestinal cancer. MiR-224 expression was homogeneous in specimens from healthy donors and was independent of anatomical location in the colon. One-way analysis of variance revealed no statistical differences among the 6 anatomical location groups (FIG. 33A and FIG. 38).

Figure 39A:
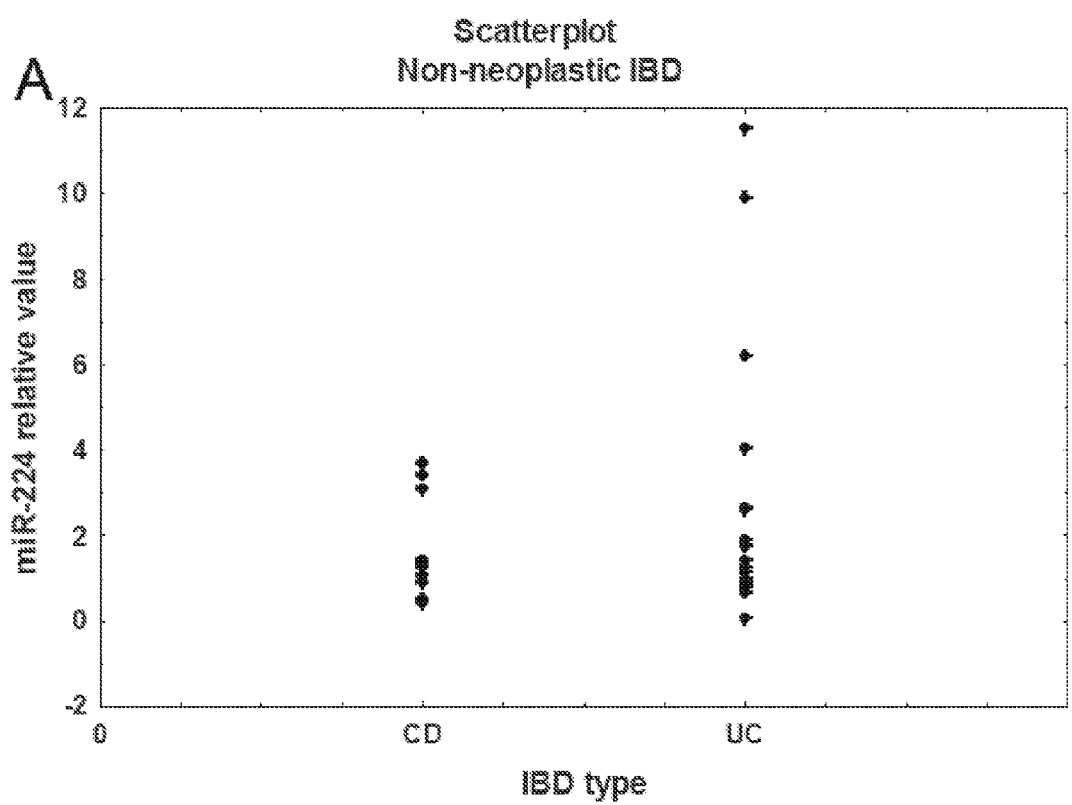
FIG. 39. (A) Comparison of miR-224 status in patients with non-neoplastic CD vs. UC. (B) Comparison of miR-224 status in patients with neoplastic Crohn's disease vs. ulcerative colitis. (C) Comparison of miR-224 status with respect to disease activity. (D) Comparison of miR-224 status with respect to age. UC=ulcerative colitis; CD=Crohn's disease.
Figure 39B:
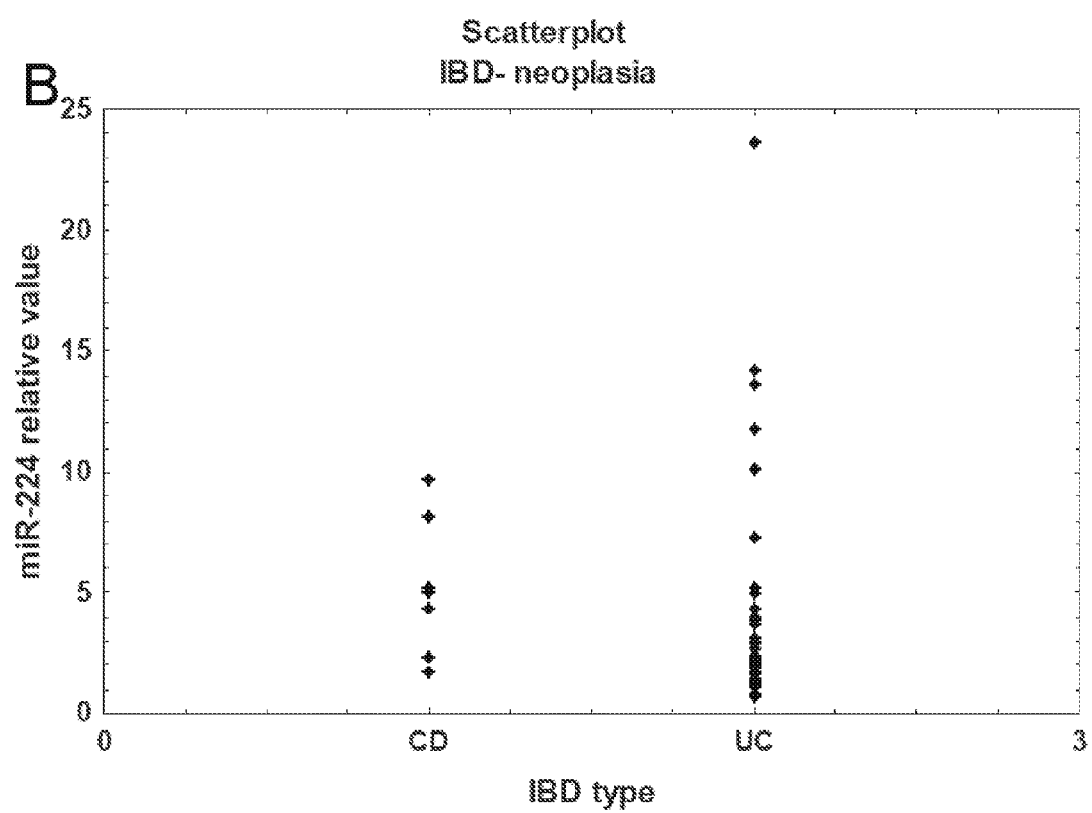

Mir-224 Expression Follows a Stepwise Escalation During Neoplastic Progression. We further determined miR-224 levels in patients with IBD lacking any evidence of neoplasia (FIG. 33B). MiR-224 showed no difference between unaffected colon specimens from patients with IBD and normal colonic mucosa. In chronically inflamed specimens from patients with IBD, miR-224 levels were significantly elevated compared with normal mucosa (2.17-fold change; P=0.008, Student t test) or to unaffected mucosa from patients with IBD (2.01-fold change; P=0.019, Student t test). Within the IBD group, no differences were observed with regard to age, sex, disease activity, or MD type (see FIGS. 39A and B).

Figures 33A, 33B:
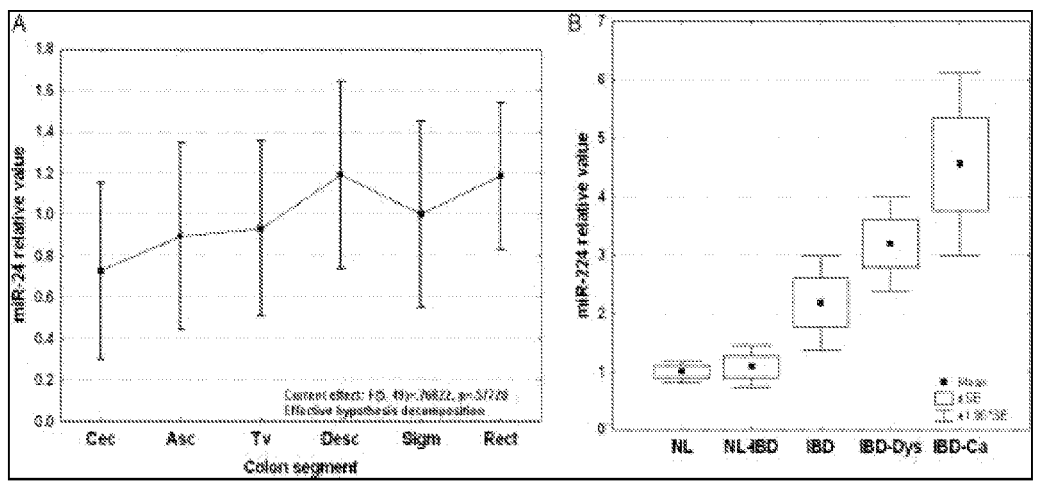
FIG. 33. A, MiR-224 relative expression levels along the normal colon. RNA was extracted from 55 normal specimens collected from patients without any history of IBD or colon cancer. Quantitative RT-PCR was performed, and signal average for normal specimens was calculated. Values displayed are relative to normal average value. The numbers of specimens for each colon segment are shown in brackets. B, Dynamic changes of miR-224 expression levels during IBD-related neoplastic transformation. Quantitative RT-PCR was performed using as template total RNA extracted from 162 patient specimens. Samples were grouped according to their pathologic status, and the average value for each group was calculated. NL, normal specimen from patients without IBD or colorectal cancer history; NL-IBD, normal "unaffected" specimens from patients with IBD; IBD, "affected" chronically inflamed specimens from patients with IBD; IBD-Dys, dysplastic specimens from patients with IBD; IBD-Ca, cancer specimens from patients with IBD. Fold differences relative to the average for normal specimens group are displayed. Error bars represent standard error of the mean.
Figure 39C:
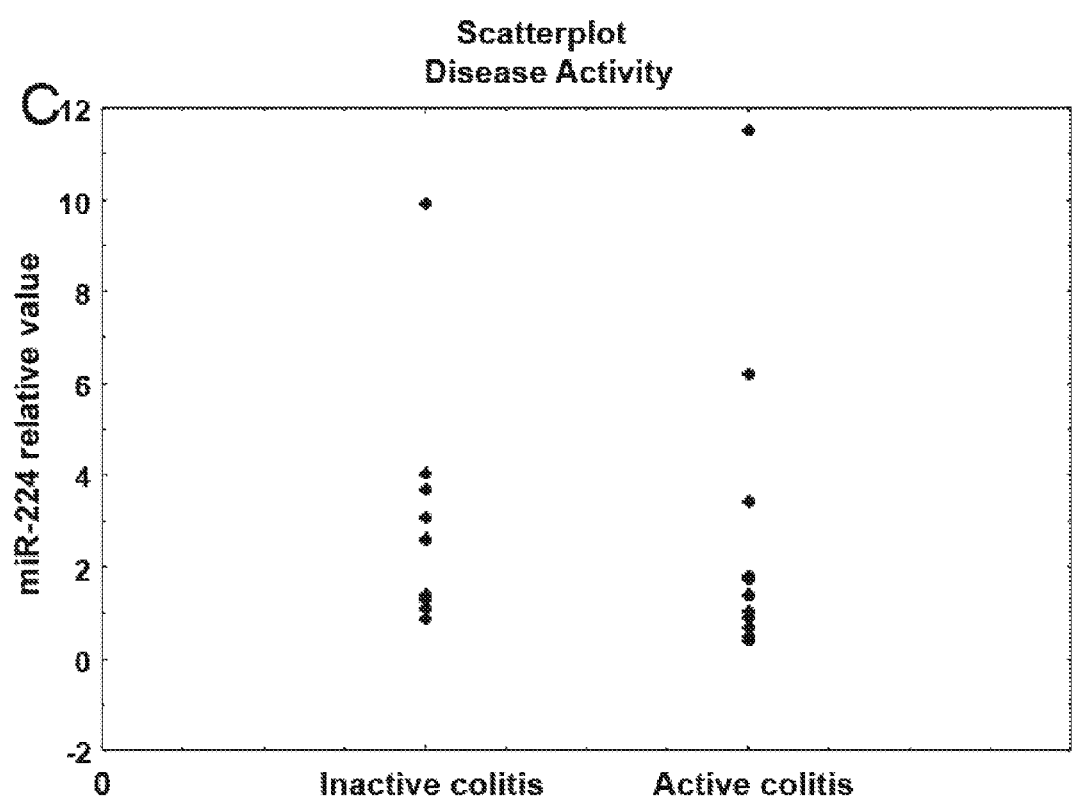
Figure 39D:
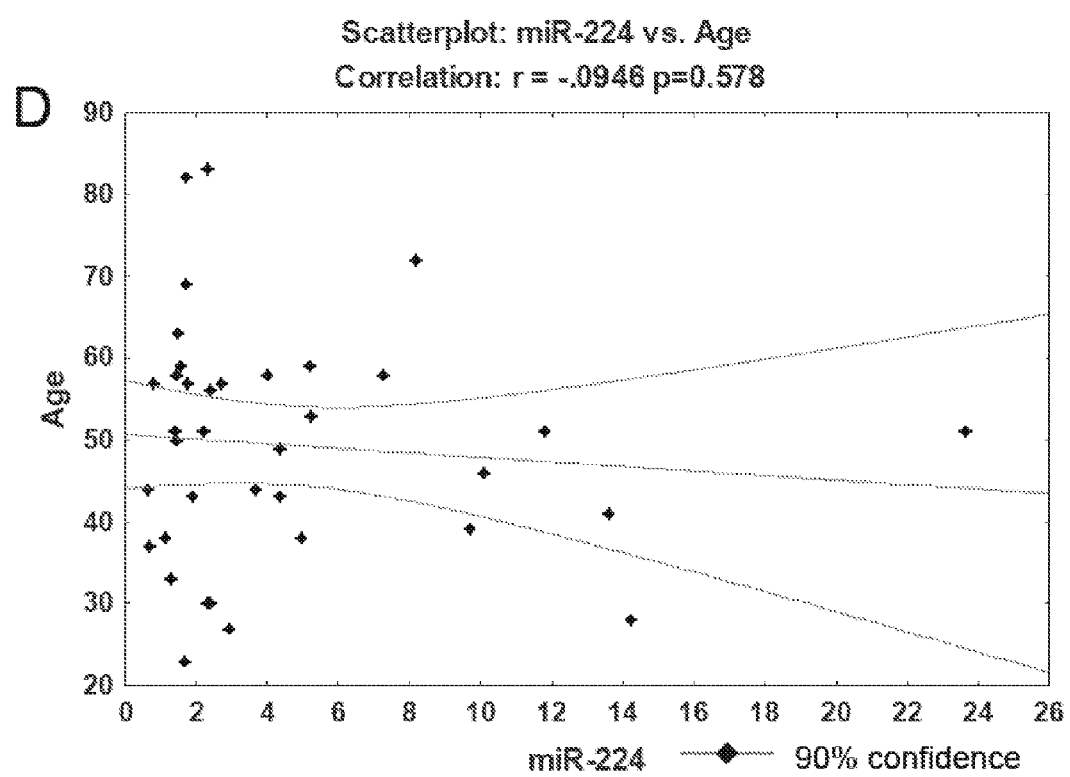

Next, we assessed miR-224 expression by qRT-PCR in a cohort of specimens consisting of 11 IBD-associated dysplasias and 38 frank MD carcinomas (FIG. 33B). In IBD-associated dysplasias, expression of miR-224 was elevated compared with normal-appearing mucosa from healthy or patients with IBD (3.31-fold and 3.06-fold increase, respectively; P<0.001, Student t test). However, no statistically significant change was observed in IBD-associated dysplasias versus chronically inflamed nonneoplastic IBD mucosa. MiR-224 was 4.47-fold higher in IBD cancers (P<0.001, Student t test) than in normal colon from healthy patients. Within the IBD cancer group, no differences were observed with regard to age, sex, disease duration, or underlying IBD type (see FIGS. 39C and D, and data not shown). Importantly, miR-224 was significantly elevated in IBD cancers versus unaffected mucosae (4.13-fold difference, P<0.001, Student t test) and chronically inflamed specimens (2.05-fold difference, P=0.012, Student t test). Taken together, these results suggest that miR-224 expression exhibits a stepwise escalation during progression from normal to chronic inflammation to neoplasia, suggesting the involvement of miR-224 in both chronic inflammation and colonic carcinogenesis.

Figure 34:
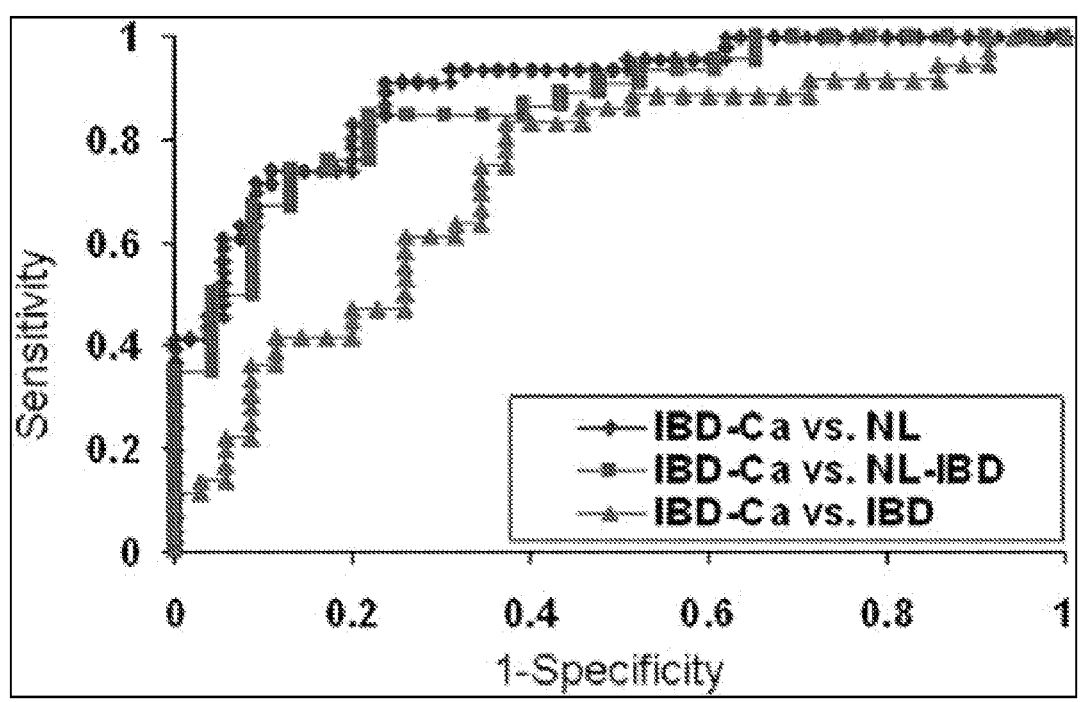
FIG. 34. ROC curve analysis of miR-224 expression levels determined by qRT-PCR. Individual miR-224 qRT-PCR levels were grouped according to their pathology. NL, normal specimen from patients without IBD or colorectal cancer history; NL-IBD, normal "unaffected" specimens from patients with IBD; IBD, "affected" chronically inflamed specimens from patients with IBD; IBD-Ca, cancer specimens from patients with IBD. AUROC for the IBD-Ca versus NL, NL-IBDs, or IBD was 0.896 (95% confidence interval, 0.83-0.95), 0.865 (95% confidence interval, 0.77-0.95), and 0.73 (95% confidence interval, 0.61-0.84), respectively. x axis=1 sensitivity. y axis=specificity.

ROC Curve Analyses. We also evaluated the potential clinical utility of miR-224 expression as a biomarker using ROC curves (FIG. 34). The ROC curves evaluated the diagnostic accuracy of miR-224 for IBD cancers (n=38) versus colonoscopy-assessed normals (n=55), IBD (n=35), or normal unaffected IBD specimens (n=22). For the discrimination between IBD cancers and normal specimens, the area under the curve (AUROC) for the miR-224 qRT-PCR assay was 0.896 (sensitivity 82.6%, specificity 80%). For the ability to distinguish IBD cancers from normal unaffected IBD specimens, the AUROC was 0.865 (sensitivity 84.7%, specificity 78.3%); finally, for the capacity to differentiate between IBD cancers and IBD specimens, the AUROC was 0.73 (sensitivity 83.3%, specificity 62.9%).

Pathways Triggered by Dysregulated miR-224 Expression. MiR-224 has been reported to be overexpressed in a wide variety of solid tumors, including those of the liver, pancreas, thyroid, and kidney, as well as in Wnt signaling-associated medulloblastomas. These studies support a role for miR-224 in tumor initiation or progression; however, to date, only 3 genes have been confirmed as being directly controlled by miR-224. MiRs may exert a broad impact on cellular gene expression programs, either directly or through signaling cascades downstream of their direct target mRNAs. Thus, to identify direct targets of a miR, one strategy is to examine global expression profile changes associated with altered miR expression and to subsequently combine this result with bioinformatic analysis. Although some bona fide miR targets directly regulated by impaired translation may not be identified by this approach, and although some downregulated genes may not be directly regulated by the miR in question, this strategy has successfully identified targets of several mammalian miRs. Therefore, we performed mRNA expression array analyses of HCT Dicer-KO cells transfected with either a miR-224 mimic or a nonspecific mimic. Dicer-KO cells were used to prevent confounding of interpretation as a result of secondary changes in endogenous miR levels, which require Dicer for their production.

In preliminary experiments, miR induction in cancer cells in the absence of stress factors resulted in a modest shift of gene expression, which was difficult to substantiate (Olaru et al. and data not shown). Previous reports have linked miR-224 to cell survival and drug resistance. Therefore, to induce a proapoptotic response and to enhance the magnitude of changes in mRNA levels, cells were then pretreated with doxorubicin before miR-224 transfection. Data were analyzed with IPA software, choosing a 3-fold change in mRNA expression as a threshold. From these results, we deduced that miR-224 appears to regulate a network of genes controlling the cell cycle, cancer, and cellular development, the last of which constituted the most associated network function affected by miR-224 induction. A summary of these analyses is displayed in.

MiR-224 Induces G1-S Release in Colon Cancer Cells. mRNA arrays coupled with IPA analysis suggested that miR-224 exerts its effects via dysregulation of the cell cycle. To verify this hypothesis, we performed cell cycle analyses. In the presence of doxorubicin, G1-S release occurred in HCT-116 Dicer-KO cells (Table 12).

TABLE 12

Flow Cytometric Analysis of the Cell Cycle After Transfection of Colon Cancer Cell Lines With miR-224 or an NSM

| Cell line | G0-G1 | S | G2-M |
|---|---|---|---|
| CACO-2 | | | |
| NSM | 52.70 ± 2.52 | 23.36 ± 6.82 | 22.65 ± 5.62 |
| miR-224 mimic | 46.16 ± 3.16 | 28.26 ± 5.85 | 24.76 ± 3.36 |
| P | 0.049 | 0.432 | 0.653 |
| HCT-116 Dicer -KO doxorubicin | | | |
| NSM | 14.21 ± 1.58 | 62.47 ± 0.83 | 23.31 ± 3.55 |
| miR-224 mimic | 10.02 ± 0.62 | 66.38 ± 2.59 | 23.58 ± 2.82 |
| P | 0.013 | 0.068 | 0.923 |

Figures 35A, 35B:
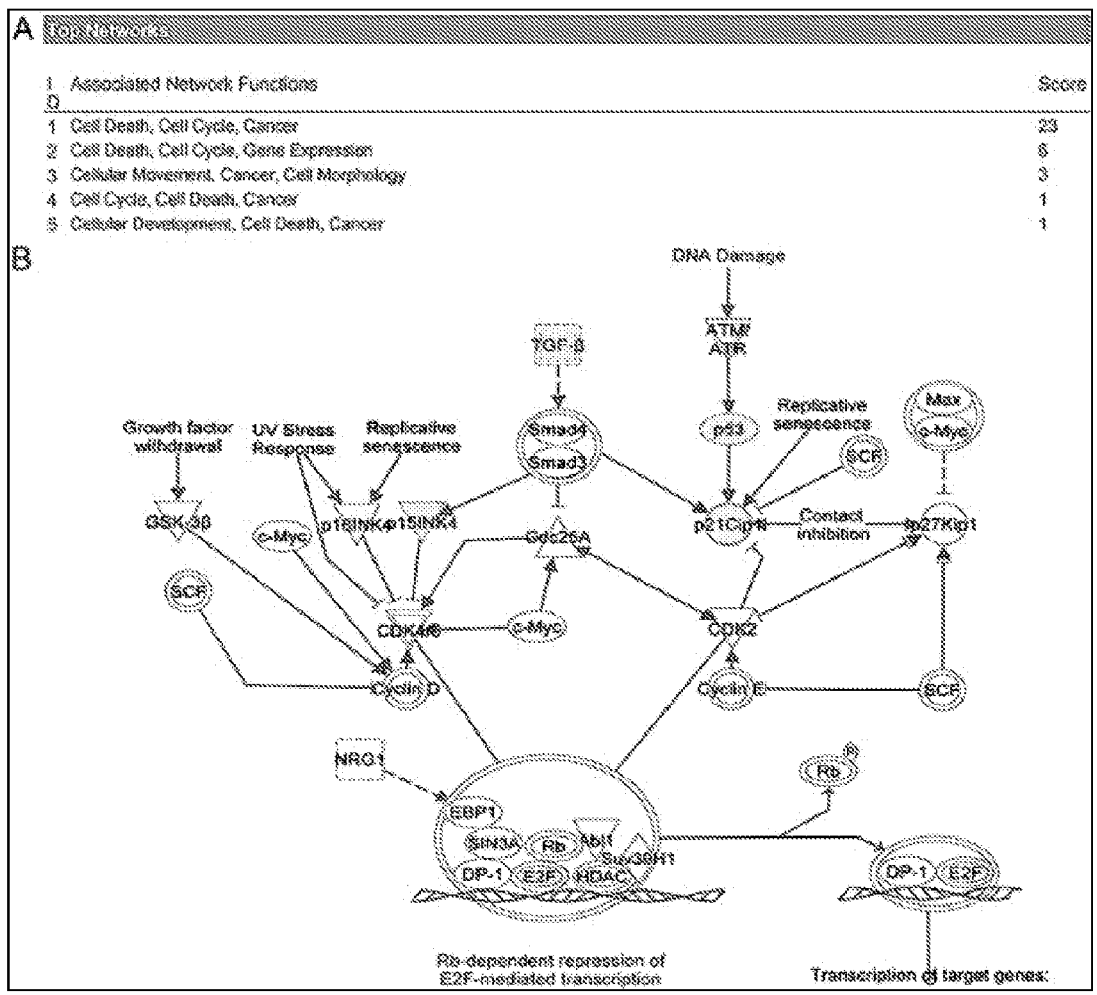
FIG. 35. A, Genes with altered expression on miR-224 stimulation are involved in the cell cycle control. The list of genes identified to be downregulated on miR-224 stimulation was filtered and input into IPA with the purpose of identifying general mechanisms of miR function. Top associated network functions are displayed. B, In silico analysis identifies p21 as a putative direct target of miR-224. The list of dysregulated genes identified by cDNA arrays (downregulated and upregulated genes are highlighted in green and red, respectively) was overlayed on the list of TargetScan predicted miR-224 targets.
Figure 36:
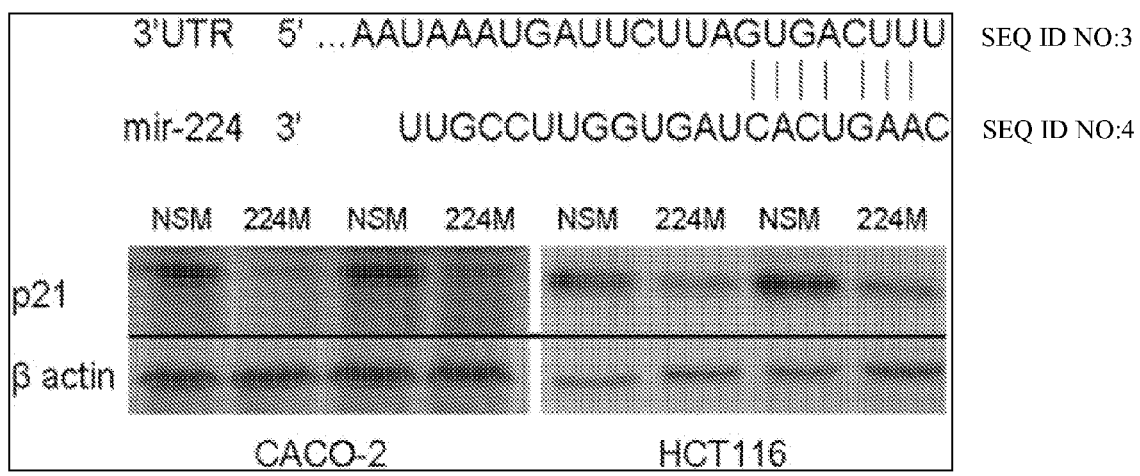
FIG. 36. Protein expression of p21 decreases on miR-2244 stimulation. Representative Western blots of p21 protein in CACO-2 and HCT-116 cell lines are shown. Equal protein loading was performed, as shown by [beta]-actin. Predicted miR-224 binding site within p21 3'-UTR is shown.
Figure 40:
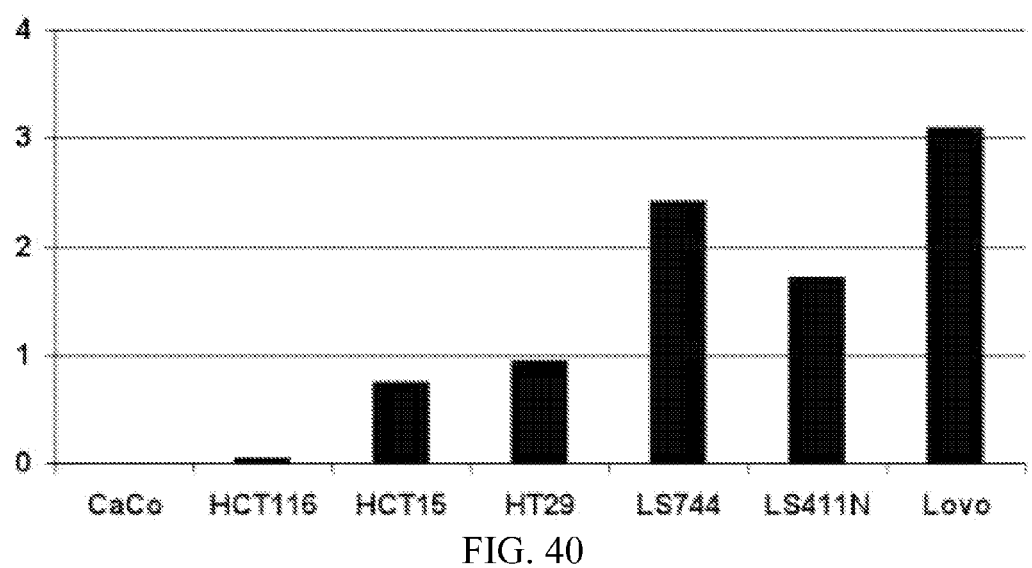
FIG. 40. miR-224 expression level in colon cancer cell lines. x-axis=colon cancer cell lines; y-axis=miR-224 level.

Interestingly, this cell cycle effect was abolished in the absence of doxorubicin, in agreement with results observed by Wang et al. We also performed cell cycle analyses in a second colon cancer cell line, CaCO-2. We chose this cell line because it exhibited the lowest miR-224 expression levels among 7 colon cancer cell lines tested (see FIG. 40). Forced overexpression of miR-224 in CaCo-2 cells, even in the absence of genotoxic stress (doxorubicin), led to a marked decrease in the G0/G1 cell population (Table 12).

p21 Is a Direct Target of miR-224. To investigate the possible mechanisms conferring oncogenic properties on miR-224, we performed in silico analyses using search engines to predict biologic targets of this miR. Using IPA software, we overlayed the target genes predicted by TargetScan onto miR-224-dysregulated genes involved in the G1-S checkpoint (from IPA analysis of our mRNA array data). This approach identified p21 as the sole G1-S checkpoint candidate for direct miR-224 regulation (FIG. 35B). Transfection of CaCO-2 and HCT-116 colon cancer cells with miR-224 mimics produced dramatic p21 downregulation versus cells transfected with a synthetic nonspecific mimic (FIG. 36).

Figure 37:
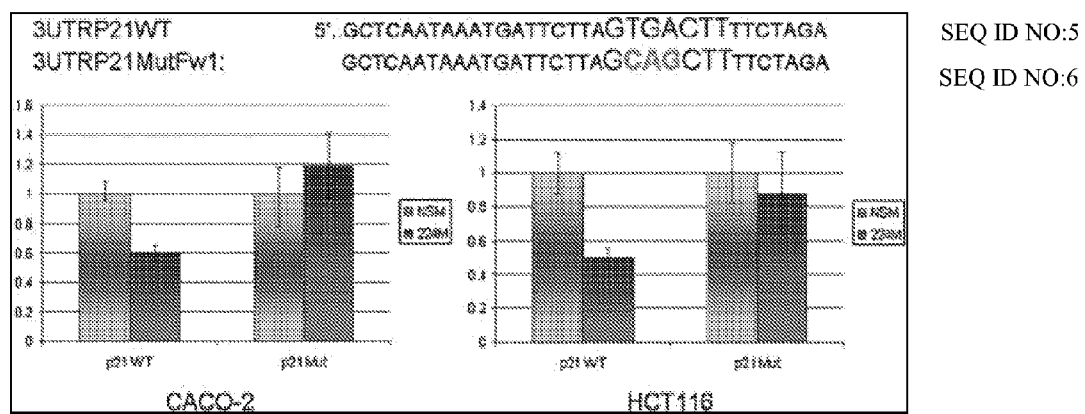
FIG. 37. MiR-224 directly interacts with the binding site in the 3'-UTR of p21. y axis=relative luminescence normalized to the luminescence level in NSM treatment. x axis=treatment conditions. NSM, nonspecific mimic; 224M, miR-224 mimic; p21WT, p21 wild-type 3'-UTR containing miR-224 binding site; p21 Mut, p21 3'-UTR containing a mutated miR-224 binding site. Standard error of the mean is shown. MiR-224 induces a statistically significant decrease in luminescence (P value t test) of the forward p21 3'-UTR fragment versus NSM.

To investigate whether miR-224 directly interacts with p21, we measured the luciferase activity of plasmids containing the p21-3'-UTR in cells transfected with either a miR-224 mimic or an NSM (FIG. 37). Cells transfected with the miR-224 mimic demonstrated 50% and 40% decreased luciferase activity in HCT-116 and CaCO-2 cells, respectively (P=0.001., Student t test) versus NSM-transfected cells. Site-directed mutagenesis of 3 nucleotides within the predicted miR-224 binding site within the p21-3'-UTR eliminated this effect of miR-224 overexpression on luciferase activity. These results indicate that p21 is directly targeted and inhibited by miR-224.

Discussion

Post-transcriptional control of gene expression by miRs has emerged as an important mechanism in the maintenance of cellular homeostasis. A growing body of evidence supports an important role of miRs in tumor initiation, progression, and metastasis. In gastrointestinal cancers, numerous reports have highlighted frequent dysregulation of mills that are tumor suppressive (e.g., miR-34 or miR-143/145) as well as oncogenic (e.g., miR-21 or the miR-17-92 cluster). However, despite numerous studies describing miR. expression profiles in sporadic colon cancer, to date, no published studies have emerged to describe global miR expression alterations in IBD-associated frank colon cancers, and only one study delineated altered miR profiles in tumors from a chronically inflamed murine colon cancer model. Here, we report global miR dysregulation in human IBD-associated colon cancers.

Several authors have reported that IBD-related colorectal cancer is frequently diagnosed at an advanced stage. MiRs have been studied for their potential as biomarkers in the detection of a range of diseases, including inflammatory diseases and cancers. One feature that makes miRs useful as biomarkers is their apparent ability to discriminate diseases arising in different organs or anatomical locations. For example, in MD, miR expression patterns differ between ileal Crohn disease (CD), proximal and distal colonic CD, and UC. In addition to their presence in tissues, miRs may also occur in peripheral blood or fecal samples, increasing their ultimate potential utility as noninvasive biomarkers. In peripheral blood, miRs can distinguish between healthy controls and patients with UC or CD. Perhaps, more clinically relevant miRs can also discriminate patients with colorectal cancer from those with IBD. Thus, our novel panel of altered miRs in IBD-associated colon cancer establishes a potential foundation for the future development of noninvasive cancer screening strategies in IBD. Further studies are needed to confirm the feasibility of such an approach in the management of patients with IBD.

In a previous study, we reported altered miR profiles associated with colonic IBD-associated dysplasias. It should be emphasized that dysplasia represents an earlier step in the IBD progression continuum. Although dysplasia found during colonoscopy is a strong predictor of concomitant or future carcinoma, this stage may not remain stable and may even regress, in contrast to frank carcinoma. Many biologic features of dysplasia are not shared by frank carcinoma and vice versa. In the current study, we report miR species manifesting altered expression in IBD cancers versus nonneoplastic IBD mucosae. Although the miR profile of IBD-associated cancers shares many similarities with that of IBD-associated dysplasia, dysregulation of new miR species was also observed. One possible explanation for our new findings is that dysregulation of one subset of miRs may occur early in the colitis-associated dysplasia-carcinoma timeline, whereas alteration of a different subset represents a later event. Alternatively, some miRs may display modest but steady increases at each subsequent stage of neoplastic progression. Indeed, miR-224 levels gradually increased during progression from noninflamed to chronically inflamed nonneoplastic to dysplastic and finally to frankly cancerous mucosae. However, this increase in miR-224 levels was relatively minimal at the earlier dysplastic stage, reaching statistical significance only at the transition to frank cancer.

The dominant paradigm of cancer development is embodied in the multihit model of tumorigenesis, which invokes successive events ("hits"), leading to the inactivation of tumor-suppressive genes and the activation of oncogenes. In addition to genetic changes, protein levels of tumor suppressor genes can be influenced by other mechanisms, including miR-mediated dysregulation. These additional molecular events may prove critical in triggering malignant transformation or conferring a survival advantage on cancerous or precancerous cells. This concept underscores the importance of understanding the mechanisms regulating gene expression by miRs. MiRs interact with their mRNA targets through base-pairing with, and subsequently inhibiting expression of, their target genes. Because prediction engines can yield hundreds of potential candidates, identifying these mRNA targets still remains a challenge. Using mRNA microarrays, coupled with pathway analyses, we determined that miR-224 appears to coordinate a network of genes involved in cell cycle control, cancer, and cellular development. Subsequently, our cell cycle analyses confirmed that miR-224 overexpression indeed induces release from the G1-S checkpoint, thereby circumventing a key cellular defense mechanism against uncontrolled proliferation. The ability of miR-224 to increase proliferation of HCT-116 colon cancer cells was previously reported by Wang et al, although a specific mechanism or mRNA target for this miR was not identified in their study. Our own in silico analyses identified p21 as the sole mRNA candidate that simultaneously is downregulated by miR-224, controls the cell cycle, and possesses a miR-224 binding site within its 3'-UTR. p21 is a tumor suppressor gene that acts as a major regulator of cell cycle progression from G1 to S by inhibiting cyclin-dependent kinases 2 and 4. This is an important defense mechanism by which cells exposed to damaging agents are prevented from further dividing. Indeed, our luciferase assays confirmed p21 mRNA as a bona fide direct miR-224 target, suggesting one possible mechanism by which miR-224 could contribute to tumorigenesis.

To our knowledge, this study represents the first systematic analysis of miR expression alterations associated with the progression of chronic inflammation to frank colorectal carcinoma in patients with IBD. Moreover, it provides direct evidence that miR-224, the most significantly overexpressed miR in IBD-associated cancers, dysregulates cell cycle control by targeting p21. Thus, these results uncover a new miR signaling pathway and substantiate the etiologic role of miRs in the development of IBD-related carcinoma.

TABLE 13

Summary of clinical data for neoplastic specimens.

| Pathology | Colon Segment | Grade | Stage | Age | Sex | Type |
|---|---|---|---|---|---|---|
| IBD-Ca | Ascending | MD-PD | T3N0 | 33 | F | UC |
| IBD-Ca | Rectum | MD | T3N0Mx | 51 | M | UC |
| IBD-Ca | Cecum | WD | T1N0Mx | 38 | M | UC |
| IBD-Ca | Sigmoid | MD-PD | T3N0Mx | 58 | F | UC |
| IBD-Ca | Rectum | PD | T3NX | 57 | M | UC |
| IBD-Ca | Rectum | MD | T3bN1 | 49 | m | UC |
| IBD-Ca | Rectosigmoid | PD | T1N0 | 46 | m | UC |
| IBD-Ca | Sigmoid | PD | T3N1 | 63 | m | UC |
| IBD-Ca | Ileocecal valve | WDtoMD | T3N0 | 69 | f | CR |
| IBD-Ca | Rectum | MDtoPD | T2N0 | 57 | f | UC |
| IBD-Ca | Rectum | MPD | T3N2 | 43 | M | CD |
| IBD-Ca | Splenic Flexure | PD | T3N2 | 72 | F | CD |
| IBD-Ca | ileocecal valve | MD-PD | T2N0 | 39 | M | CD |
| IBD-Ca | Rectosigmoid | MPD | T3N0 | 38 | M | UC |
| IBD-Ca | Rectum | PD | T2N0 | 51 | M | UC |
| IBD-Ca | Transverse | MD-PD | T3N2 | 58 | F | UC |
| IBD-Ca | Sigmoid | MD-PD | T3N0 | 57 | F | UC |
| IBD-Ca | Rectum | MD | T3aN0 | 51 | F | UC |
| IBD-Ca | Rectum | WD | T2N1 | 59 | M | IC |
| IBD-Ca | Rectosigmoid | WD-MD | T4N2 | 37 | M | UC |
| IBD-Ca | Hepatic Flexure | PD | T3N0 | 44 | M | UC |
| IBD-Ca | Rectum | WD-PD | T3N2 | 53 | F | UC |
| IBD-Ca | Ascending | MD-PD | T3N2 | 28 | M | UC |
| IBD-Ca | Hepatic Flexure | WD-PD | T3aN2 | 27 | M | UC |
| IBD-Ca | Rectosigmoid | MD | T4N2 | 59 | F | UC |
| IBD-Ca | Sigmoid | MD-PD | T3N0 | 56 | M | UC |
| IBD-Ca | Sigmoid | MD | T3N0 | 58 | M | UC |
| IBD-Ca | Cecum | MD | T4N1 | 50 | M | UC |
| IBD-Ca | Descending | MD | T2N0 | 30 | F | CD |
| IBD-Ca | Rectosigmoid | MD | T3N0 | 51 | M | UC |
| IBD-Ca | Transverse | WD | T3N0 | 30 | M | UC |
| IBD-Ca | Ascending | MD | T3N2 | 44 | F | IC |
| IBD-Ca | Cecum | PD | T4N0 | 23 | M | UC |
| IBD-Ca | Rectum | NA | T4Nx | 43 | F | UC |
| IBD-Ca | Rectum | MD | T4N1 | 41 | F | UC |
| IBD-Ca | Sigmoid | WD | T1N0 | 83 | F | UC |
| IBD-Ca | Rectum | MD | T1N0 | 82 | F | UC |
| IBD-Ca | Descending | WD | NA | NA | NA | UC |

IBD-Dys = dysplastic specimens from IBD patients;
IBD-Ca = cancer specimens from IBD patients;
WD = well differentiated;
MD = moderate differentiated;
PD = poorly differentiated.

TABLE 14

Summary of clinical data for individual disease groups

|  | IBD-Ca | IBD-Dys | IBD | N-IBD | N |
|---|---|---|---|---|---|
| Age average (range) | 49.4 (23.83) | 57.4 (47-74) | 46.2 (15.82) | 48.8 (15-82) | 60.6 (41-81) |
| Sex male;female; NA | 21;16 | 6;4;1 | 23;12 | 16;6;1 | 12;2 |
| IBD type UC;CD;IC | 3;5;2 | 7;2;2 | 22;12;1 | 16;7 | N/A |
| Location Right;Left:NA | 12;26 | 4;5;2 | 05;30 | 18;4;1 | 26;29 |

N = normal from patients without IBD or colorectal cancer history;
N-IBD = normal "unaffected" specimens from IBD patients;
IBD = "affected" chronically inflamed specimens from IBD patients;
IBD-Dys = dysplastic specimens from IBD patients;
IBD-Ca = cancer specimens from IBD patients.
NA = not available

TABLE 15 miR species dysregulated in both IBD-Dysplasia vs. IBD and IBD-Cancer vs. IBD

| Systematic Name | Fold dif IBD-Dys vs IBD | p-value IBD-Dys vs IBD | Fold dd. IBD-Ca vs IBD | p-value IBD-Ca v IBD | Dysregulation |
|---|---|---|---|---|---|
| hsa-miR-31 | 5.85 | 0.0001 | 7.22 | 0.0037 | up in IBD-neoplasia |
| hsa-miR-31* | 5.94 | <0.0001 | 6.40 | 0.0028 | up in IBD-neoplasia |
| hsa-miR-552 | 6.31 | 0.0085 | 6.26 | 0.0036 | up in IBD-neoplasia |
| hsa-miR-135b | 2.88 | 0.0254 | 6.05 | 0.0002 | up in IBD-neoplasia |
| hsa-miR-200a | 5.03 | 0.0102 | 4.06 | 0.0196 | up in IBD-neoplasia |
| hsa-miR-96 | 2.93 | 0.0125 | 3.52 | 0.0135 | up in IBD-neoplasia |
| hsa-miR-200b* | 4.60 | 0.0074 | 2.90 | 0.0453 | up in IBD-neoplasia |
| hsa-miR-424* | 2.09 | 0.0407 | 2.02 | 0.0080 | up in IBD-neoplasia |
| hsa-miR-892b | 3.63 | 0.0002 | 6.09 | <0.0001 | down in IBD-neoplasia |
| hsa-miR-139-5p | 3.09 | 0.0033 | 3.50 | 0.0096 | down in IBD-neoplasia |
| hsa-miR-501-5p | 2.25 | 0.0014 | 2.81 | 0.0001 | down in IBD-neoplasia |
| hsa-miR-146b-5p | 2.48 | 0.0016 | 2.18 | 0.0139 | down in IBD-neoplasia |

We claim:

1. A method comprising measuring the levels of a panel of microRNAs comprising miR-21, miR-192, miR-200b, miR-224, miR-7, miR-95, miR-124, miR-138, miR-214, miR-452 and miR-1305 from a biological sample obtained from a patient, wherein the patient has inflammatory bowel disease (IBD) or IBD-dysplasia.

2. The method of claim 1, wherein the measuring step is accomplished using quantitative real-time polymerase chain reaction (qRT-PCR) or a microarray.

3. The method of claim 1, wherein the sample is blood, plasma or serum.

4. The method of claim 3, wherein the sample is blood.

5. The method of claim 3, wherein the sample is plasma.

6. The method of claim 3, wherein the sample is serum.

* * * * *

```
                            SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Primer for luciferase assay.

<400> SEQUENCE: 1
acagctagcc tgccaggggt caa                                           23

<210> SEQ ID NO 2
<211> LENGTH: 23
<212> TYPE: DNA
<213> ORGANISM: Artificial Sequence
<220> FEATURE:
<223> OTHER INFORMATION: Primer for luciferase assay.

<400> SEQUENCE: 2
tgccatctag aactacagct tca                                           23

<210> SEQ ID NO 3
<211> LENGTH: 23
<212> TYPE: RNA
<213> ORGANISM: Homo sapiens
```

```
<400> SEQUENCE: 3
aauaaaugau ucuuagugac uuu                                          23

<210> SEQ ID NO 4
<211> LENGTH: 21
<212> TYPE: RNA
<213> ORGANISM: Homo sapiens

<400> SEQUENCE: 4
uugccuuggu gaucacugaa c                                            21

<210> SEQ ID NO 5
<211> LENGTH: 33
<212> TYPE: DNA
<213> ORGANISM: Homo sapiens

<400> SEQUENCE: 5
gctcaataaa tgattcttag tgacttttct aga                               33

<210> SEQ ID NO 6
<211> LENGTH: 33
<212> TYPE: DNA
<213> ORGANISM: Homo sapiens

<400> SEQUENCE: 6
gctcaataaa tgattcttag cagcttttct aga                               33
```